US00RE43274E

(19) United States
(12) Reissued Patent
Pandey et al.

(10) Patent Number: US RE43,274 E
(45) Date of Reissued Patent: Mar. 27, 2012

(54) FLUORINATED PHOTOSENSITIZERS RELATED TO CHLORINS AND BACTERIOCHLORINS FOR PHOTODYNAMIC THERAPY

(75) Inventors: Ravindra K. Pandey, Williamsville, NY (US); William R. Potter, East Amherst, NY (US); Thomas J. Dougherty, Grand Island, NY (US)

(73) Assignee: Health Research, Inc., Buffalo, NY (US)

(21) Appl. No.: 12/321,729

(22) Filed: Jan. 23, 2009

Related U.S. Patent Documents

Reissue of:
(64) Patent No.: 7,166,719
Issued: Jan. 23, 2007
Appl. No.: 10/607,922
Filed: Jun. 27, 2003

U.S. Applications:
(60) Provisional application No. 60/392,473, filed on Jun. 27, 2002.

(51) Int. Cl.
*C09B 47/04* (2006.01)

(52) U.S. Cl. ..... 424/9.362; 424/9.6; 534/14; 540/140; 540/145

(58) Field of Classification Search ..... 540/145
See application file for complete search history.

(56) References Cited

U.S. PATENT DOCUMENTS

| | | | | |
|---|---|---|---|---|
| 3,710,795 | A | 1/1973 | Higuchi et al. | 128/260 |
| 3,817,837 | A | 6/1974 | Rubenstein et al. | 195/103.5 R |
| 3,927,193 | A | 12/1975 | Hansen et al. | 424/1 |
| RE28,819 | E | 5/1976 | Thompson | 424/243 |
| 4,044,126 | A | 8/1977 | Cook et al. | 424/243 |
| 4,328,245 | A | 5/1982 | Yu et al. | 424/305 |
| 4,331,647 | A | 5/1982 | Goldenberg | 424/1 |
| 4,348,376 | A | 9/1982 | Goldenberg | 424/1 |
| 4,358,603 | A | 11/1982 | Yu | 560/2 |
| 4,361,544 | A | 11/1982 | Goldenberg | 424/1 |
| 4,364,923 | A | 12/1982 | Cook et al. | 424/46 |
| 4,374,925 | A | 2/1983 | Litman et al. | 435/7 |
| 4,409,239 | A | 10/1983 | Yu | 424/305 |
| 4,410,545 | A | 10/1983 | Yu et al. | 424/305 |
| 4,414,209 | A | 11/1983 | Cook et al. | 424/243 |
| 4,444,744 | A | 4/1984 | Goldenberg | 424/1.1 |
| 4,468,457 | A | 8/1984 | Goldenberg et al. | 435/69 |
| 4,474,893 | A | 10/1984 | Reading | 436/547 |
| 4,479,895 | A | 10/1984 | Auditore-Hargreaves | 260/112 B |
| 4,521,762 | A | 6/1985 | Kapral | 340/347 |
| 4,522,811 | A | 6/1985 | Eppstein et al. | 514/2 |
| 4,577,636 | A | 3/1986 | Spears | 128/654 |
| 4,624,846 | A | 11/1986 | Goldenberg | 424/1.1 |
| 4,649,151 | A | 3/1987 | Dougherty et al. | 514/410 |
| 4,656,186 | A | 4/1987 | Bommer et al. | 514/410 |
| 4,675,338 | A | 6/1987 | Bommer et al. | 514/410 |
| 4,693,885 | A | 9/1987 | Bommer et al. | 424/9.61 |
| 4,753,958 | A | 6/1988 | Weinstein et al. | 514/410 |
| 4,818,709 | A | 4/1989 | Primus et al. | 436/518 |
| 4,861,876 | A | 8/1989 | Kessel | 540/145 |
| 4,866,168 | A | 9/1989 | Dougherty et al. | 540/145 |
| 4,878,891 | A | 11/1989 | Judy et al. | 604/5 |
| 4,889,129 | A | 12/1989 | Dougherty et al. | 128/664 |
| 4,916,221 | A | 4/1990 | Kumadaki et al. | 540/145 |
| 4,925,736 | A | 5/1990 | Shikowitz | 424/449 |
| 4,932,934 | A | 6/1990 | Dougherty et al. | 604/21 |
| 4,935,498 | A | 6/1990 | Sessler et al. | 534/15 |
| 4,946,778 | A | 8/1990 | Ladner et al. | 435/69.6 |
| 4,957,481 | A | 9/1990 | Gatenby | 604/20 |
| 4,968,715 | A | 11/1990 | Dougherty et al. | 514/410 |
| 4,997,639 | A | 3/1991 | Aizawa et al. | 424/9 |
| 5,002,962 | A | 3/1991 | Pandey et al. | 514/410 |
| 5,004,811 | A | 4/1991 | Bommer et al. | 540/145 |
| 5,015,463 | A | 5/1991 | Dougherty et al. | 424/7.1 |
| 5,028,594 | A | 7/1991 | Carson | 514/23 |
| 5,028,621 | A | 7/1991 | Dougherty et al. | 514/410 |
| 5,033,252 | A | 7/1991 | Carter | 53/425 |
| 5,041,078 | A | 8/1991 | Matthes et al. | 604/4 |
| 5,051,415 | A | 9/1991 | Moran et al. | 514/185 |
| 5,052,558 | A | 10/1991 | Carter | 206/439 |
| 5,053,006 | A | 10/1991 | Watson | 604/52 |
| 5,059,415 | A | 10/1991 | Neuwelt | 424/9 |
| 5,062,431 | A | 11/1991 | Potter | 128/665 |
| 5,066,274 | A | 11/1991 | Bommer et al. | 604/20 |

(Continued)

FOREIGN PATENT DOCUMENTS

EP 0120054 B1 3/1984

(Continued)

OTHER PUBLICATIONS

Li et al., Application for Ruppert's Reagent in Preparing Novel Perfluorinated Porphyrins, Chlorins and Bacteriochlorins, J. Chem. Soc., Perkin Trans. 1, 1999, 1785-1787.*

Pandy et al., Chlorin-based Symmetrical and Unsymmetrical Dimer with Amide Linkages: Effect of the Substituents on Photodynamic and Photophysical Properties, J. Chem. Soc., Perkin Trans. 1, 2000, 3113-3121.*

Smith et al., Bacteriochlorophylls c from Chloropseudomonas Ethylicum, Composition and NMR Studies of the Pheophorbides and Derivatives, Journal of the American Chemical Society, 1980, 2437-2448.*

Li et al. Application for Ruppert's Reagent in Preparing Novel Perfluorinated Porphyrins, Chlorins and Bacteriochlorins, J. Chem. Soc., Perkin Trans. 1, 1999, 1785-1787.*

Anderson et al. "Photodynamic therapy for sarcoma pulmonary metastases: a preclinical toxicity study," *Anticancer Res.* 23:3713-3718 (2003).

(Continued)

*Primary Examiner* — James O Wilson
*Assistant Examiner* — Brian McDowell
(74) *Attorney, Agent, or Firm* — Michael L. Dunn

(57) ABSTRACT

Provided herein are compounds for detection, diagnosis and treatment of target tissues or target compositions, including hyperproliferative tissues such as tumors, using photodynamic methods. In particular, photosensitizer compounds that collect in hyperproliferative tissue are provided. In another embodiment, compounds that absorb light at a wavelength of from about 700 to about 850 nm are provided. In a further embodiment, compounds that are detectable by magnetic resonance imaging are provided.

15 Claims, 12 Drawing Sheets

U.S. PATENT DOCUMENTS

| | | | | |
|---|---|---|---|---|
| 5,066,291 | A | 11/1991 | Stewart | 606/3 |
| 5,074,632 | A | 12/1991 | Potter | 385/31 |
| 5,093,349 | A | 3/1992 | Pandey et al. | 514/410 |
| 5,095,030 | A | 3/1992 | Levy et al. | 514/410 |
| 5,111,821 | A | 5/1992 | Potter | 128/654 |
| 5,145,863 | A | 9/1992 | Dougherty et al. | 514/410 |
| 5,171,741 | A | 12/1992 | Dougherty | 514/185 |
| 5,173,504 | A | 12/1992 | Dougherty | 514/410 |
| 5,190,536 | A | 3/1993 | Wood et al. | 606/16 |
| 5,190,966 | A | 3/1993 | Dougherty et al. | 514/410 |
| 5,198,460 | A | 3/1993 | Pandey et al. | 514/410 |
| 5,205,291 | A | 4/1993 | Potter | 128/654 |
| 5,216,012 | A | 6/1993 | Morgan et al. | 514/410 |
| 5,219,345 | A | 6/1993 | Potter | 606/15 |
| 5,222,795 | A | 6/1993 | Hed | 362/32 |
| 5,225,433 | A | 7/1993 | Dougherty et al. | 514/410 |
| 5,257,970 | A | 11/1993 | Dougherty | 604/20 |
| 5,263,925 | A | 11/1993 | Gilmore, Jr. et al. | 604/4 |
| 5,298,018 | A | 3/1994 | Narciso, Jr. | 604/21 |
| 5,308,861 | A | 5/1994 | Aizawa et al. | 514/410 |
| 5,314,905 | A | 5/1994 | Pandey et al. | 514/410 |
| 5,323,907 | A | 6/1994 | Kalvelage | 206/531 |
| 5,330,741 | A | 7/1994 | Smith et al. | 424/9 |
| 5,344,928 | A | 9/1994 | Masuya et al. | 544/37 |
| 5,368,841 | A | 11/1994 | Trauner et al. | 424/9 |
| 5,403,308 | A | 4/1995 | Wood et al. | 606/17 |
| 5,418,130 | A | 5/1995 | Platz et al. | 435/2 |
| 5,430,051 | A | 7/1995 | Aizawa et al. | 514/410 |
| 5,441,531 | A | 8/1995 | Zarate et al. | 607/90 |
| 5,459,159 | A | 10/1995 | Pandey et al. | 514/410 |
| 5,482,698 | A | 1/1996 | Griffiths | 424/141 |
| 5,484,803 | A | 1/1996 | Richter | 514/410 |
| 5,496,308 | A | 3/1996 | Brown et al. | 606/15 |
| 5,498,710 | A | 3/1996 | Pandey et al. | 540/145 |
| 5,500,009 | A | 3/1996 | Mendes et al. | 607/88 |
| 5,503,637 | A | 4/1996 | Kyricos et al. | 607/88 |
| 5,506,255 | A | 4/1996 | Smith et al. | 514/410 |
| 5,514,669 | A | 5/1996 | Selman | 514/63 |
| 5,525,338 | A | 6/1996 | Goldenberg | 424/178.1 |
| 5,532,171 | A | 7/1996 | Motsenbocker | 436/533 |
| 5,534,506 | A | 7/1996 | Morgan et al. | 514/185 |
| 5,549,660 | A | 8/1996 | Mendes et al. | 607/88 |
| 5,556,612 | A | 9/1996 | Anderson et al. | 424/59 |
| 5,567,409 | A | 10/1996 | Aizawa et al. | 424/9.363 |
| 5,571,152 | A | 11/1996 | Chen et al. | 607/92 |
| 5,580,896 | A | 12/1996 | Horwell et al. | 514/419 |
| 5,591,847 | A | 1/1997 | Pandey et al. | 540/472 |
| 5,594,136 | A | 1/1997 | Sessler et al. | 540/472 |
| 5,599,923 | A | 2/1997 | Sessler et al. | 540/145 |
| 5,622,983 | A | 4/1997 | Horwell et al. | 514/419 |
| 5,624,798 | A | 4/1997 | Yamamoto et al. | 435/6 |
| 5,631,281 | A | 5/1997 | Horwell et al. | 514/419 |
| 5,648,485 | A | 7/1997 | Dolphin et al. | 540/474 |
| 5,665,328 | A | 9/1997 | Horan et al. | 424/1.17 |
| 5,671,317 | A | 9/1997 | Weishaupt et al. | 385/137 |
| 5,688,486 | A | 11/1997 | Watson et al. | 424/1.65 |
| 5,697,902 | A | 12/1997 | Goldenberg | 604/49 |
| 5,698,405 | A | 12/1997 | Goldenberg | 435/7.5 |
| 5,702,432 | A | 12/1997 | Chen et al. | 607/88 |
| 5,703,230 | A | 12/1997 | Boyle et al. | 540/145 |
| 5,705,518 | A | 1/1998 | Richter et al. | 514/410 |
| 5,709,874 | A | 1/1998 | Hanson et al. | 424/423 |
| 5,715,837 | A | 2/1998 | Chen | 128/899 |
| 5,716,595 | A | 2/1998 | Goldenberg | 414/1.49 |
| 5,736,563 | A | 4/1998 | Richter | 514/410 |
| 5,741,316 | A | 4/1998 | Chen et al. | 607/61 |
| 5,759,542 | A | 6/1998 | Gurewich | 424/94.64 |
| 5,766,234 | A | 6/1998 | Chen et al. | 607/92 |
| 5,770,619 | A | 6/1998 | Richter et al. | 514/410 |
| 5,770,730 | A * | 6/1998 | Pandey et al. | 23/302 T |
| 5,773,977 | A | 6/1998 | Dougherty | 324/429 |
| 5,776,093 | A | 7/1998 | Goldenberg | 604/20 |
| 5,776,094 | A | 7/1998 | Goldenberg | 604/20 |
| 5,776,095 | A | 7/1998 | Goldenberg | 604/20 |
| 5,782,896 | A | 7/1998 | Chen et al. | 607/88 |
| 5,800,478 | A | 9/1998 | Chen et al. | 607/88 |
| 5,814,008 | A | 9/1998 | Chen et al. | 604/21 |
| 5,824,080 | A | 10/1998 | Lamuraglia | 623/11 |
| 5,827,186 | A | 10/1998 | Chen et al. | 600/407 |
| 5,829,448 | A | 11/1998 | Fisher et al. | 128/898 |
| 5,831,088 | A | 11/1998 | Dolphin et al. | 540/474 |
| 5,832,931 | A | 11/1998 | Wachter et al. | 128/898 |
| 5,840,674 | A | 11/1998 | Yatvin et al. | 514/2 |
| 5,851,225 | A | 12/1998 | Lawandy | 607/88 |
| 5,860,957 | A | 1/1999 | Jacobsen et al. | 604/156 |
| 5,864,035 | A * | 1/1999 | Pandey et al. | 540/472 |
| 5,865,840 | A | 2/1999 | Chen | 607/92 |
| 5,876,427 | A | 3/1999 | Chen et al. | 607/88 |
| 5,885,557 | A | 3/1999 | Lentini | 424/59 |
| 5,886,173 | A | 3/1999 | Hemmi et al. | 540/472 |
| 5,900,252 | A | 5/1999 | Calanchi et al. | 424/459 |
| 5,913,884 | A | 6/1999 | Trauner et al. | 607/88 |
| 5,921,244 | A | 7/1999 | Chen et al. | 128/897 |
| 5,942,534 | A | 8/1999 | Trauner et al. | 514/410 |
| 5,944,748 | A | 8/1999 | Mager et al. | 607/88 |
| 5,945,762 | A | 8/1999 | Chen et al. | 310/171 |
| 5,948,433 | A | 9/1999 | Burton et al. | 424/448 |
| 5,952,366 | A * | 9/1999 | Pandey et al. | 514/410 |
| 5,957,960 | A | 9/1999 | Chen et al. | 607/92 |
| 5,972,366 | A | 10/1999 | Haynes et al. | 424/422 |
| 5,976,535 | A | 11/1999 | Fritzberg et al. | 424/182.1 |
| 5,983,134 | A | 11/1999 | Ostrow | 604/20 |
| 5,985,307 | A | 11/1999 | Hanson et al. | 424/423 |
| 5,985,317 | A | 11/1999 | Venkateshwaran et al. | 424/449 |
| 5,997,569 | A | 12/1999 | Chen et al. | 607/88 |
| 5,997,842 | A | 12/1999 | Chen | 424/1.29 |
| 5,998,597 | A | 12/1999 | Fisher et al. | 536/23.1 |
| 6,004,534 | A | 12/1999 | Langer et al. | 424/9.321 |
| 6,010,715 | A | 1/2000 | Wick et al. | 424/448 |
| 6,015,897 | A | 1/2000 | Theodore et al. | 540/474 |
| 6,022,961 | A | 2/2000 | Yamamoto et al. | 536/24.3 |
| 6,024,975 | A | 2/2000 | D'Angelo et al. | 424/449 |
| 6,028,099 | A | 2/2000 | de Juan, Jr. | 514/434 |
| 6,036,941 | A | 3/2000 | Bottiroli et al. | 424/9.6 |
| 6,039,975 | A | 3/2000 | Shah et al. | 424/473 |
| 6,048,359 | A | 4/2000 | Biel | 607/92 |
| 6,048,736 | A | 4/2000 | Kosak | 436/536 |
| 6,051,207 | A | 4/2000 | Klaveness et al. | 424/9.1 |
| 6,051,702 | A | 4/2000 | Bird et al. | 540/122 |
| 6,060,082 | A | 5/2000 | Chen et al. | 424/450 |
| 6,063,108 | A | 5/2000 | Salansky et al. | 607/89 |
| 6,063,777 | A | 5/2000 | Hikida et al. | 514/183 |
| 6,071,495 | A | 6/2000 | Unger et al. | 424/9.51 |
| 6,080,160 | A | 6/2000 | Chen et al. | 606/72 |
| 6,084,717 | A | 7/2000 | Wood et al. | 359/629 |
| 6,090,788 | A | 7/2000 | Lurie | 514/23 |
| 6,092,531 | A | 7/2000 | Chen et al. | 128/899 |
| 6,096,066 | A | 8/2000 | Chen et al. | 607/88 |
| 6,096,289 | A | 8/2000 | Goldenberg | 424/1.49 |
| 6,100,893 | A | 8/2000 | Ensz et al. | 345/420 |
| 6,103,751 | A * | 8/2000 | Pandey et al. | 514/410 |
| 6,107,466 | A | 8/2000 | Hasan et al. | 530/351 |
| 6,117,862 | A | 9/2000 | Margaron et al. | 514/185 |
| 6,120,751 | A | 9/2000 | Unger | 424/9.51 |
| 6,123,923 | A | 9/2000 | Unger et al. | 424/9.52 |
| 6,124,342 | A | 9/2000 | Okamoto et al. | 514/432 |
| 6,131,570 | A | 10/2000 | Schuster et al. | 128/203.26 |
| 6,138,681 | A | 10/2000 | Chen et al. | 128/899 |
| 6,139,865 | A | 10/2000 | Friend et al. | 424/441 |
| 6,152,951 | A | 11/2000 | Hashimoto et al. | 607/92 |
| 6,156,506 | A | 12/2000 | Yamamoto et al. | 435/6 |
| 6,162,213 | A | 12/2000 | Stewart | 606/10 |
| 6,162,242 | A | 12/2000 | Peyman | 607/88 |
| 6,167,301 | A | 12/2000 | Flower et al. | 604/20 |
| 6,176,842 | B1 | 1/2001 | Tachibana et al. | 604/22 |
| 6,187,030 | B1 | 2/2001 | Gart et al. | 607/93 |
| 6,210,425 | B1 | 4/2001 | Chen | 607/88 |
| 6,217,869 | B1 | 4/2001 | Meyer et al. | 424/178.1 |
| RE37,180 | E | 5/2001 | Mori et al. | 514/410 |
| 6,232,295 | B1 | 5/2001 | Kayyem et al. | 514/44 |
| 6,238,426 | B1 | 5/2001 | Chen | 607/88 |
| 6,242,477 | B1 | 6/2001 | Okamoto et al. | 514/432 |
| 6,253,872 | B1 | 7/2001 | Neumann | 181/210 |
| 6,256,533 | B1 | 7/2001 | Yuzhakov et al. | 604/21 |
| 6,261,595 | B1 | 7/2001 | Stanley et al. | 424/449 |
| 6,264,914 | B1 | 7/2001 | Klaveness et al. | 424/1.65 |
| 6,267,983 | B1 | 7/2001 | Fujii et al. | 424/448 |

| | | | | |
|---|---|---|---|---|
| 6,268,120 | B1 | 7/2001 | Platz et al. | 435/2 |
| 6,271,359 | B1 | 8/2001 | Norris et al. | 536/23.1 |
| 6,273,904 | B1 | 8/2001 | Chen et al. | 607/88 |
| 6,274,552 | B1 | 8/2001 | Tamarkin et al. | 514/12 |
| 6,281,611 | B1 | 8/2001 | Chen et al. | 310/171 |
| 6,307,147 | B1 | 10/2001 | Bird et al. | 136/263 |
| 6,316,652 | B1 | 11/2001 | Steliou | 556/42 |
| 6,319,273 | B1 | 11/2001 | Chen et al. | 607/88 |
| 6,319,488 | B1 | 11/2001 | Licha et al. | 424/9.6 |
| 6,331,175 | B1 | 12/2001 | Goldenberg | 604/522 |
| 6,331,744 | B1 | 12/2001 | Chen et al. | 310/171 |
| 6,344,050 | B1 | 2/2002 | Chen | 607/88 |
| 6,350,431 | B1 | 2/2002 | Snow et al. | 424/9.6 |
| 6,387,350 | B2 | 5/2002 | Goldenberg | 424/1.57 |
| 6,406,297 | B1 | 6/2002 | Raymond et al. | 434/15 |
| 6,416,531 | B2 | 7/2002 | Chen | 607/89 |
| 6,454,789 | B1 | 9/2002 | Chen et al. | 607/88 |
| 6,482,517 | B1 | 11/2002 | Anderson | 428/402.24 |
| 6,489,314 | B1 | 12/2002 | Ashley et al. | 514/183 |
| 6,495,585 | B2 | 12/2002 | Bellnier et al. | 514/410 |
| 6,498,945 | B1 | 12/2002 | Alfheim et al. | 600/407 |
| 6,500,816 | B1 | 12/2002 | Ekimoto et al. | 514/185 |
| 6,511,971 | B1 | 1/2003 | Gorun | 514/183 |
| 6,514,995 | B1 | 2/2003 | Zaleski et al. | 514/332 |
| 6,515,113 | B2 | 2/2003 | Raymond et al. | 534/15 |
| 6,520,669 | B1 | 2/2003 | Chen et al. | 362/545 |
| 6,524,552 | B2 | 2/2003 | Klaveness et al. | 424/1.85 |
| 6,525,088 | B1 | 2/2003 | Nagano et al. | 514/452 |
| 6,527,759 | B1 | 3/2003 | Tachibana et al. | 604/500 |
| 6,534,040 | B2 | 3/2003 | Pandey et al. | 424/362 |
| 6,540,980 | B1 | 4/2003 | Blumenthal et al. | 424/9.34 |
| 6,554,853 | B2 | 4/2003 | Chen | 607/88 |
| 6,559,374 | B2 | 5/2003 | Lindsey et al. | 136/263 |
| 6,566,517 | B2 | 5/2003 | Miura et al. | 540/145 |
| 6,569,846 | B1 | 5/2003 | Scherz et al. | 514/185 |
| 6,572,839 | B2 | 6/2003 | Sugita et al. | 424/9.5 |
| 6,580,228 | B1 | 6/2003 | Chen et al. | 315/185 R |
| 6,602,274 | B1 | 8/2003 | Chen | 607/88 |
| 6,624,187 | B1 | 9/2003 | Pandey et al. | 514/410 |
| 6,657,351 | B2 | 12/2003 | Chen et al. | 310/171 |
| 2001/0022970 | A1 | 9/2001 | Dees et al. | 424/178.1 |
| 2002/0033192 | A1 | 3/2002 | Lindsey et al. | 136/263 |
| 2002/0049247 | A1 | 4/2002 | Chen | 514/410 |
| 2002/0087205 | A1 | 7/2002 | Chen | 607/88 |
| 2002/0127224 | A1 | 9/2002 | Chen | 424/130.1 |
| 2002/0127230 | A1 | 9/2002 | Chen | 424/178.1 |
| 2002/0128303 | A1 | 9/2002 | Bellnier et al. | 514/410 |
| 2002/0198576 | A1 | 12/2002 | Chen et al. | 607/88 |
| 2003/0018371 | A1 | 1/2003 | Chen | 607/88 |
| 2003/0030342 | A1 | 2/2003 | Chen et al. | 310/102 |
| 2003/0109813 | A1 | 6/2003 | Chen | 601/2 |
| 2003/0114434 | A1 | 6/2003 | Chen et al. | 514/185 |
| 2003/0167033 | A1 | 9/2003 | Chen et al. | 604/20 |
| 2003/0208249 | A1 | 11/2003 | Chen | 607/88 |
| 2004/0044197 | A1 | 3/2004 | Pandey et al. | 540/140 |
| 2004/0044198 | A1 | 3/2004 | Pandey et al. | 540/145 |

FOREIGN PATENT DOCUMENTS

| | | | |
|---|---|---|---|
| EP | 0161606 | B1 | 11/1985 |
| EP | 0243929 | B1 | 11/1987 |
| EP | 0423195 | B1 | 4/1991 |
| EP | 0425566 | B1 | 5/1991 |
| EP | 0450149 | B1 | 10/1991 |
| EP | 0468997 | B1 | 2/1992 |
| EP | 0510007 | B1 | 10/1992 |
| EP | 0682956 | B1 | 11/1995 |
| EP | 1110963 | A2 | 6/2001 |
| EP | 1131100 | B1 | 9/2001 |
| EP | 1146046 | A2 | 10/2001 |
| EP | 1164136 | A1 | 12/2001 |
| EP | 1238666 | A2 | 9/2002 |
| EP | 1256586 | A1 | 11/2002 |
| EP | 1334748 | A1 | 8/2003 |
| JP | 4218002 | | 7/1992 |
| JP | 6105921 | | 4/1994 |
| JP | 2001335578 | | 4/2001 |
| JP | 2002020389 | | 1/2002 |
| JP | 2002325853 | | 11/2002 |
| JP | 2003146989 | | 5/2003 |
| WO | 8401382 | A1 | 4/1984 |
| WO | 9000392 | A1 | 1/1990 |
| WO | 9000895 | A1 | 2/1990 |
| WO | 9012573 | A1 | 11/1990 |
| WO | 9110474 | A1 | 7/1991 |
| WO | 9313769 | A1 | 7/1993 |
| WO | 9409851 | A1 | 5/1994 |
| WO | 9505214 | A1 | 2/1995 |
| WO | 9532206 | A1 | 11/1995 |
| WO | 9637255 | A1 | 11/1996 |
| WO | 9732520 | A1 | 9/1997 |
| WO | 9732885 | A1 | 9/1997 |
| WO | 9804317 | A1 | 2/1998 |
| WO | 9806456 | A1 | 2/1998 |
| WO | 9808565 | A1 | 3/1998 |
| WO | 9814243 | A1 | 4/1998 |
| WO | 9824371 | A1 | 6/1998 |
| WO | 9824510 | A1 | 6/1998 |
| WO | 9832491 | A1 | 7/1998 |
| WO | 9832492 | A1 | 7/1998 |
| WO | 9832493 | A1 | 7/1998 |
| WO | 9846130 | A1 | 10/1998 |
| WO | 9850034 | A1 | 11/1998 |
| WO | 9856302 | A1 | 12/1998 |
| WO | 9918879 | A1 | 4/1999 |
| WO | 9920346 | A1 | 4/1999 |
| WO | 9939769 | A1 | 8/1999 |
| WO | 9952565 | A1 | 10/1999 |
| WO | 9958149 | A1 | 11/1999 |
| WO | 9966988 | A1 | 12/1999 |
| WO | 9967248 | A1 | 12/1999 |
| WO | 9967249 | A1 | 12/1999 |
| WO | WO 99/67248 | * | 12/1999 |
| WO | WO 99/67249 | * | 12/1999 |
| WO | 0015296 | A1 | 3/2000 |
| WO | 0036983 | A1 | 6/2000 |
| WO | 0041725 | A2 | 7/2000 |
| WO | 0041726 | A3 | 7/2000 |
| WO | 0041727 | A1 | 7/2000 |
| WO | 0041768 | A1 | 7/2000 |
| WO | 00/61584 | A1 | 10/2000 |
| WO | 0103770 | A1 | 1/2001 |
| WO | 0105316 | A1 | 1/2001 |
| WO | 0115694 | A1 | 3/2001 |
| WO | 0143825 | A1 | 6/2001 |
| WO | 0151087 | A2 | 7/2001 |
| WO | 01/74398 | A1 | 10/2001 |
| WO | 0178216 | A1 | 10/2001 |
| WO | 0178458 | A1 | 10/2001 |
| WO | 0198708 | A1 | 12/2001 |
| WO | 0217690 | A1 | 2/2002 |
| WO | 02/098882 | A1 | 12/2002 |
| WO | 03029494 | A1 | 4/2003 |
| WO | 03/050082 | A2 | 6/2003 |
| WO | 03052793 | A2 | 6/2003 |
| WO | 03056407 | A2 | 7/2003 |
| WO | 03061696 | A2 | 7/2003 |
| WO | 2004/002476 | A2 | 1/2004 |
| WO | 2004/005289 | A2 | 1/2004 |

OTHER PUBLICATIONS

Certified English Translation of: Fischer, H. et al., "[On the Bromination of the Esters of Mesoisochlorin e4 and Mesochlorin e6]," *Berichte der Deutschen Chemischen* 75:1778-1795 (1942).

Chen et al., "New directions in photodynamic therapy, " *ICCP-2. 2nd International Conference on Porphyrins and Phthalocyanines,* Jun. 30-Jul. 5, 2002; Kyoto, Japan: 78 [abstract S-26].

Chen et al., "New technology for deep light distribution in tissue for phototherapy," *Cancer J* 8(2):154-163. (2002).

Chen et al., "Next-generation light delivery system for multitreatment extended-duration photodynamic therapy (MED-PDT)," *Proc SPIE* 2972:161-166 (1997).

Database Crossfire Beilstein, Database Acession No. 4286587 (Reaction ID), for Levinson, E.G. et al., Russ. J. Bioorg. Chem (Engl. Transl.) 21(3):199-203 (1995) in Russian in the :Bioorg. Khim. 21(3):230-234 (1995).

Derwent English Abstract, Accession No. 1996-475153, citing Russian Patent RU 2054944 C, published Feb. 27, 1996, "Production of purpurin-18 for treatment of tumours—comprises extracting vegetable waste with ethanol, oxidative splitting, degreasing and purifying".
Fischer, H. et al., "[On the Bromination of the Esters of Mesoisochlorin $e_4$ and Mesochlorin $e_6$]," *Berischte der Deutschen Chemischen* 75:1778-1795 (1942).
Haslam et al., "Recent Developments in Methods for the Esterification and Protection of the Carboxyl Group," *Tetrahedron* 36: 2409-2433 (1980).
Jones et al. "Photodynamic therapy for patients with advanced non-small-cell carcinoma of the lung," *Clin Lung Cancer.* 3(1):37-41 (2001).
Li et al., "Application of Ruppert's reagent in preparing novel perfluorinated porphyrins, chlorins and bacteriochlorins", *J. Chem. Soc. Perkin Trans* 1, 1785-1787 (1999).
Li et al., "Synthesis, comparative photosensitizing efficacy, human serum albumin (site II) binding ability, and intracellular localization characteristics of novel benzobacteriochlorins derived from vic-dihydroxybacteriochlorins,". *J Med Chem.* 46(25):5349-5359 (2003).
Lustig et al., "A multicenter Phase I safety study of intratumoral photoactivation of talaporfin sodium in patients with refractory solid tumors," *Cancer* 98(8):1767-71 (2003).
Patent Abstract of Japan citing Japanese Patent Application JP 09124652, published May 13, 1997, "Porphyrin Derivative and Use Thereof".
Schmidt-Erfurth et al., "Photodynamic therapy of subfoveal choroidal neovascularization: clinical and angiographic examples," *Graefe's Arch Clin Exp Opthalmol.* 236:365-374 (1998).
Schmidt-Erfurth et al., "Vascular Targeting in Photodyamic Occlusion of Subretinal Vessels," *Opthalmology* 101:1953-1961 (1994).
Smith et al., "Bacteriochlorophylls c from *Chloropseudomonas ethylicum.* Composition and NMR Studies of the Pheophorbides and Derivatives", Am. Chem. Soc., 102(7):2437-2448 (1980).
Zheng et al., "Chlorin-based symmetrical and unsymmetrical dimers with amide linkages: effect of the substituents on photodynamic and photophysical properties," *J. Chem. Soc. Perkins 1,* pp. 3113-3121 (2000).
Zheng et al., "PDT using a novel LED light source and LSI 1 in a rat liver model," *30th Annual Meeting of the American Society for Photobiology;* Jul. 13-17, 2002; Quebec City, Canada. American Society for Photobiology: 33 [abstract 95].
Bellnier et al., "Population pharmacokinetics of the photodynamic therapy agent 2-[1-hexyloxyethyl]-2-devinyl pyropheophorbide-a in cancer patients", *Cancer Res.,* 63(8):1806-1813 (2003).
Bellnier et al., "Design and construction of a light-delivery system for photodynamic therapy", *Med. Phys.,* 26(8):1552-1558 (1999).
Bellnier et al., "The time course of cutaneous porphyrin photosensitization in the murine ear", *Photochemistry and Photobiology,* 49(3):369-372 (1989).
Bellnier et al., "Murine pharmacokinetics and antitumor efficacy of the photodynamic sensitizer 2-[1-hexyloxyethyl]-2-devinyl pyropheophorbide-a", *J Photochem Photobiol B.* 20(1):55-61 (1993).
Bellnier et al., "The validation of a new vascular damage assay for photodynamic therapy agents", *Photochem Photobiol.,* 62(5):896-905 (1995).
Bellnier et al. "Protection of murine foot tissue and transplantable tumor against Photofrin-II-mediated photodynamic sensitization with WR-2721", *Journal of Photochemistry and Photobiology B. Biology* 4:219-225 (1989).
Bellnier et al. "An assay for the quantitation of Photofrin in tissues and fluids", *Photochem Photobiol.* 66(2):237-244 (1997).
Bellnier et al., "Distribution and elimination of Photofrin II in mice", *Photochemistry and Photobiology* 50(2):221-228 (1989).
Bellnier et al., "Membrane lysis in Chinese hamster ovary cells treated with hemtoporphyrin derivative plus light", *Photochem Photobiol.* 36(1):43-47 (1982).
Bellnier et al., "A preliminary pharmacokinetic study of intravenous Photofrin in patients", *J Clin Laser Med Surg.,* 14(5):311-4 (1996).
Bellnier et al., "Haematoporphyrin derivative photosensitization and gamma-radiation damage interaction in Chinese hamster ovary fibroblasts", *Int J Radiat Biol Relat Stud Phys Chem Med.* 50(4):659-664 (1986).
Bernstein et al., "Photofrin photodynamic therapy for treatment of AIDS-related cutaneous Kaposi's sarcoma", *AIDS,* 13(13):1697-1704 (1999).
Box et al., "Radical ion saturation in some sulfur compounds x-irradiated at 4.2 degrees" *K. Radiat Res.* 51(1):10-14 (1972).
Boyle et al., "Photobleaching of photofrin II as a means of eliminating skin photosensitivity", *Photochemistry and Photobiology,* 46(6):997-1001 (1987).
Brasseur et al., "Photodynamic activities and skin photosensitivity of the *bis*(dimethylthexylsiloxy)silicon 2,3-naphthalocyanine in mice", *Photochemistry and Photobiology* 62(6):1058-1065 (1995).
Brennan et al., "Preparation of Bispecific Antibodies by Chemical Recombination of Monoclonal Immunoglobulin $G_1$ Fragments-",*Science,* 229: 81-83 (1985).
Bugelski et al., "Autoradiographic distribution of hematoporphyrin derivative in normal and tumor tissue of the mouse", *Cancer Res.,* 41(11 Pt 1):4606-4612 (1981).
Chen et al., "Effect of meso-substituents on the osmium tetraoxide reaction and pinacol-pinacolone rearrangement of the corresponding vic-dihydroxyporphyrins", *J Org Chem.* 66(11):3930-3939 (2001).
Chen et al., "Bacteriopurpurinimides: highly stable and potent photosensitizers for photodynamic therapy", *J. Med. Chem.* 45:255-258 (2002).
Derwent Abstract Accession No. 9432597, for Japanese Patent Application JP 2003146989 published May 21, 2003, entitled "Pyropheophorbides and their use in photodynamic therapy".
Dimitroff et al., "Anti-angiogenic activity of selected receptor tyrosine kinase inhibitors, PD166285 and PD173074: implications for combination treatment with photodynamic therapy", *Investigational New Drugs,* 17:121-135 (1999).
Dissous et al. ,*Schistosoma Mansoni* Surface Antigen Defined by a Rat Monoclonal IgG2a,*J. Immunol.* 129: 2232-2234 (1982).
Doiron et al., "Fluorescence bronchoscopy for detection of lung cancer", *Chest,* 76(1):27-32 (1979).
Dougherty TJ, "Transannular peroxides as radiation sensitizers", *Radiat Res.,* 55(1):101-108 (1973).
Dougherty TJ, "A brief history of clinical photodynamic therapy development at Roswell Park Cancer Institute", *J Clin Laser Med Surg.* 14(5):219-221 (1996).
Dougherty TJ, "Use of hematoporphyrin in photodynamic therapy", *J Photochem Photobiol B.* 8(4):439 (1991).
Dougherty TJ, "Photosensitizers: therapy and detection of malignant tumors", *Photochemistry and Photobiology* 45(6):879-889 (1987).
Dougherty TJ, "Activated dyes as antitumor agents", *J Natl Cancer Inst.* 52(4):1333-1336 (1974).
Dougherty TJ, "Photodynamic therapy", *Photochem Photobiol,* 58(6):895-900 (1993).
Dougherty TJ, "Photodynamic Therapy: Part II", *Seminars in Surgical Oncology,* 11:333-334 (1995).
Dougherty TJ, "Photodynamic therapy: status and potential", *Oncology* (*Huntingt*). 3(7):67-73; Discussion 74, 77-78 (1989).
Dougherty TJ, "Photoradiation therapy for cutaneous and subcutaneous malignancies", *J Invest Dermatol.* 77(1):122-124 (1981).
Dougherty TJ, "Photodynamic therapy (PDT) of malignant tumors", *CRC Critical Reviews in Oncology/Hematology* 2(2):83-116 (1984).
Dougherty TJ, "Photoradiation therapy", *Urology,* 23(3 *Suppl*):61-64 (1984).
Dougherty TJ, "Photosensitization of malignant tumors", *Seminars in Surgical Oncology* 2:24-37 (1986).
Dougherty TJ, "Variability in hematoporphyrin derivative preparations", *Cancer Res.* 42(3):1188 (1982).
Dougherty TJ, "Photoradiation therapy for bronchogenic cancer", *Chest,* 81(3):265-266 (1982).
Dougherty TJ, "Photodynamic therapy—new approaches", *Seminars in Surgical Oncology* 5:6-16 (1989).
Dougherty TJ, "Hematoporphyrin as a photosensitizer of tumors", *Photochem Photobiol.* 38(3):377-379 (1983).
Dougherty TJ, "Photodynamic therapy", *Adv Exp Med Biol.,* 193:313-328 (1985).

Dougherty TJ, "Photodynamic therapy", *Clinics in Chest Medicine,* 6(2):219-236 (1985).
Dougherty TJ, "An update on photodynamic therapy applications", *J Clin Laser Med Surg.* 20(1):3-7 (2002).
Dougherty TJ, "Studies on the structure of porphyrins contained in Photofrin II" *Photochem Photobiol.,* 46(5):569-573 (1987).
Dougherty et al., "Energetics and efficiency of photoinactivation of murine tumor cells containing hematoporphyrin", *Cancer Research* 36:2330-2333 (1976).
Dougherty et al., "Photoradiation therapy. II. Cure of animal tumors with hematoporphyrin and light", *Journal of the National Cancer Institute,* 55(1):115-121 (1975).
Dougherty et al., "Photoradiation therapy for the treatment of malignant tumors", *Cancer Res.* 38(8):2628-2635 (1978).
Dougherty et al., "Photodynamic Therapy," *Journal of the National Cancer Institute,* 90(12):889-905 (1998).
Dougherty TJ, "Hematoporphyrin derivative for detection and treatment of cancer", *J Surg Oncol.* 15(3):209-210 (1980).
Dougherty et al., "Photoradiation therapy—clinical and drug advances", *Adv Exp Med Biol.* 160:3-13 (1983).
Dougherty et al., "Photoradiation in the treatment of recurrent breast carcinoma", *J Natl Cancer Inst.,* 62(2):231-237 (1979).
Dougherty et al., "Cutaneous phototoxic occurrences in patients receiving Photofrin", *Lasers Surg Med.* 10(5):485-488 (1990).
Dougherty et al., "Interstitial photoradiation therapy for primary solid tumors in pet cats and dogs", *Cancer Res.* 41(2):401-404 (1981).
Dougherty, "Photodynamic therapy in gastrointestinal cancer", *Lasers in Surgery and Medicine* 12:114 (1992).
Dougherty et al., "Characterization of intra-tumoral porphyrin following injection of hematoporphyrin derivative or its purified component", *Photochemistry and Photobiology,* 46(1):67-70 (1987).
Dougherty et al., "The role of the peripheral benzodiazepine receptor in photodynamic activity of certain pyropheophorbide ether photosensitizers: albumin site II as a surrogate marker for activity", *Photochem Photobiol.,* 76(1):91-97 (2002).
Dougherty TJ, "An overview of the status of photoradiation therapy", *Prog Clin Biol Res.* 170:75-87 (1984).
Dougherty et al., "Photodynamic therapy", *Eur J Cancer.* 28A(10):1734-1742 (1992).
Dougherty et al., "The structure of the active component of hematoporphyrin derivative", *Prog Clin Biol Res.,* 170:301-314 (1984).
Dougherty et al., "Of what value is a highly absorbing photosensitizer in PDT?" *J Photochem Photobiol B.,* 8(2):223-225 (1991).
Douglass et al., "Intra-abdominal applications of hematoporphyrin photoradiation therapy", *Adv Exp Med Biol.,* 160:15-21 (1983).
Farrell et al., "A diffusion theory model of spatially resolved, steady-state diffuse reflectance for the noninvasive determination of tissue optical properties in vivo", *Med. Phys.,* 19(4):879-888 (1992).
Fingar et al., "Drug and light dose dependence of photodynamic therapy: a study of tumor cell clonogenicity and histologic changes", *Photochem Photobiol.,* 45(5):643-650 (1987).
Flock et al., "Monte Carlo Modeling of Light Propagation in Highly Scattering Tissues—I: Model Predictions and Comparison with Diffusion Theory," *IEEE Transactions on Biomedical Engineering,* 36(12):1162-1168 (1989).
Flock et al., "Monte Carlo Modeling of Light Propagation in Highly Scattering Tissues—II: Comparison with Measurements in Phantoms," *IEEE Transactions on Biomedical Engineering,* 36(12):1169-1173 (1989).
Fukuzumi et al., "Photochemical and electrochemical properties of zinc chlorin-C60 dyad as compared to corresponding free-base chlorin-C60, free-base porphyrin-C60, and zinc porphyrin-C60 dyads", *J Am Chem Soc.,* 123(43):10676-10683 (2001).
Glennie et al., "Preparation and Performance of Bispecific $F(ab'y)_2$ Antibody Containing Thioether-Linked Fab'y Fragments",*J. Immunol.,* 139:2367-2375 (1987).
Gomer CJ et al., "Determination of [3H]- and [14C]hematoporphyrin derivative distribution in malignant and normal tissue", *Cancer Res.* 39(1):146-151 (1979).
Graham et al., "Structure-activity relationship of new octaethylporphyrin-based benzochlorins as photosensitizers for photodynamic therapy", *Photochem Photobiol.* 77(5):561-566 (2003).
Gryshuk et al., "A first comparative study of purpurinimide-based fluorinated vs. nonfluorinated photosensitizers for photodynamic therapy", *Photochem Photobiol.,* 76(5):555-559 (2002).
Gryzch et al., "In Vitro and In Vivo Effector Function of Rat IgG2a Monoclonal Anti-S. *Masoni* Antibodies",*J. Immunol.* 129: 2739-2743 (1982).
Henderson et al., "Tumor destruction and kinetics of tumor cell death in two experimental mouse tumors following photodynamic therapy", *Cancer Res.,* 45(2):572-576 (1985).
Henderson et al., "Interaction of photodynamic therapy and hyperthermia: tumor response and cell survival studies after treatment of mice in vivo", *Cancer Res.,* 45(12 Pt 1):6071-6077 (1985).
Henderson et al., "Bacteriochlorophyll-a as photosensitizer for photodynamic treatment of transplantable murine tumors", *J. Photochem. Photobiol. B: Biol.* 10:303-313 (1991).
Henderson et al., "An in vivo quantitative structure-activity relationship for a congeneric series of pyropheophorbide derivatives as photosensitizers for photodynamic therapy", *Cancer Res.* 57(18):4000-4007 (1997).
Henderson et al., "How does photodynamic therapy work?" *Photochem Photobiol.* 55(1):145-157 (1992).
Henderson et al., "Aspects of the cellular uptake and retention of hematoporphyrin derivative and their correlation with the biological response to PRT in vitro", *Adv Exp Med Biol.,* 160:129-38 (1983).
Henderson et al., "Studies on the mechanism of tumor destruction by photoradiation therapy", *Prog Clin Biol Res.* 170:601-612 (1984).
Herrera-Ornelas et al., "Photodynamic therapy in patients with colorectal cancer", *Cancer,* 57(3):677-684 (1986).
Ho et al., "Some components of the tumor-localizing fraction of hematoporphyrin derivative", *Photochemistry and Photobiology,* 52(6):1085-1088 (1990).
Ho et al., "Carbon-14 labeling and biological activity of the tumor-localizing derivative of hematoporphyrin", *Photochem Photobiol.* 48(4):445-449 (1988).
Ho et al., "Activity and physicochemical properties of Photofrin", *Photochem Photobiol.* 54(1):83-87 (1991).
IUPAC-IUB Commission on Biochemical Nomenclature (see, Biochem. 11: 942-944 (1972).
Karpovsky et al., "Production of Target-Specific Effector Cells Using Hetero-Cross-Linked Aggregates Containing Anti-Target Cell and Anti-Fcy", *J. Exp. Med.* 160:1686 (1984).
Kasper et al., "Isolation and Characterization of A Monoclonal Antibody-Resistant Antigenic Mutant of *Toxoplasma Gondii", J. Immunol.* 129: 1694-1699 (1982).
Kessel et al., "Photosensitization with bacteriochlorins", *Photochem Photobiol.,* 58(2):200-203 (1993).
Kessel et al., "Photosensitization by diporphyrins joined via methylene bridges", *Photochemistry and Photobiology* 48(6):741-744 (1988).
Kessel et al., "Photosensitization by synthetic diporphyrins and dichlorins in vivo and in vitro", *Photochemistry and Photobiology* 53(4):475-479 (1991).
Khan et al., "An evaluation of photodynamic therapy in the management of cutaneous metastases of breast cancer", *Eur. J Cancer.* 29A(12):1686-1690 (1993).
Kher et al., "Mechano and thermoluminescence of gamma-irradiated CaSO4:Dy phosphor.", *Radiat Prot Dosimetry.* 100(1-4):281-284 (2002).
Kozyrev et al., "Thermolysis of vic-dihydroxybacteriochlorins: a new approach for the synthesis of chlorin-chlorin and chlorin-porphyrin dimers", *Org Lett.* 1(8):1193-1196 (1999).
Lele et al., "Photodynamic therapy in gynecologic malignancies", *Gynecol Oncol.* 34(3):350-352 (1989).
Li et al., "A novel synthetic route to fused propenochlorin and benzochlorin photodynamic therapy probes", *Chem Commun (Camb).* (11):1172-1173 (2002).

Li et al., "Thermolysis of vic-dihydroxybacteriochlorins: effect of the nature of substrates in directing the formation of chlorin-chlorin dimers with fixed and flexible orientations and their preliminary in vitro photosensitizing efficacy", *J Org Chem.* 68(10):3762-3772 (2003).
Li et al., "A simple and efficient approach for the synthesis of fluorinated and nonfluorinated octaethylporphyrin-based benzochlorins with variable lipophilicity, their in vivo tumor uptake, and the preliminary in vitro photosensitizing efficacy", *J Org Chem.* 66(4):1316-1325 (2001).
Liu, Ma et al., "Heteroantibody duplexes target cells for lysis by cytotoxic T lymphocytes",*Proc. Natl. Acad. Sci. USA* 82:8648-8652 (1985).
Lobel et al., "2-[1-hexyloxyethyl]-2-devinyl pyropheophorbide-a (HPPH) in a nude rat glioma model: implications for photodynamic therapy", *Lasers Surg Med.* 29(5):397-405 (2001).
MacDonald et al., "Subcellular localization patterns and their relationship to photodynamic activity of pyropheophorbide-a derivatives", *Photochem Photobiol.* 70(5):789-797 (1999).
Mang et al., "Photobleaching of porphyrins used in photodynamic therapy and implications for therapy", *Photochemistry and Photobiology,* 45(4):501-506 (1987).
Mang et al., "Time and sequence dependent influence of in vitro photodynamic therapy (PDT) survival by hyperthermia", *Photochem Photobiol.,* 42(5):533-540 (1985).
Mang et al., "Fluorescence detection of tumors. Early diagnosis of microscopic lesions in preclinical studies", *Cancer* 71(1):269-276 (1993).
Merrifield et al., "Design and synthesis of antimicrobial peptides", *Ciba Foundation Symposium,* 186:5-20 (1994).
Mettath et al., "DNA interaction and photocleavage properties of porphyrins containing cationic substituents at the peripheral position" *Bioconjugate Chem.,* 10:94-102 (1999).
Mettath et al., "Effect of substituents in directing the formation of benzochlorins and isobacteriochlorins in porphyrin and chlorin systems", *Organic Letters* 1(12):1961-1964 (1999).
Milstein et al., "Hybrid hybridomas and the production of bi-specific monoclonal antibodies",*Immunol. Today* 5:299-305 (1984).
Moesta et al., "Protoporphyrin IX occurs naturally in colorectal cancers and their metastases" *Cancer Research,* 61:991-999 (2001).
Morgan et al., "Comparison of photodynamic targets in a carcinoma cell line and its mitochondrial DNA-deficient derivative", *Photochemistry and Photobiology,* 71(6):747-757 (2000).
Morrison and Boyd, *Organic Chemistry,* (5th Ed., 1987), Chapter 13, entitled "Aromaticity," pp. 477-497.
Moskal et al., "Operation and photodynamic therapy for pleural mesothelioma: 6-year follow-up", *Ann Thorac Surg.,* 66:1128-1133 (1998).
Nambisan et al., "Intraoperative photodynamic therapy for retroperitoneal sarcomas", *Cancer,* 61(6):1248-1252 (1988).
Niedre et al., "Direct Near-infrared Luminescence Detection of Singlet Oxygen Generated by Photodynamic Therapy in Cell in Vitro and Tissues in Vivo", *Photochemistry and Photobiology,* 75(4):382-391 (2002).
Nogrady, Medicinal Chemistry A Biochemical Approach, Oxford University Press, New York, pp. 388-392 (1985).
North et al. "Viral Inactivation in Blood and Red Cell Concentrates with Benzoporphyrin Derivative", *Blood Cells* 18:129-40 (1992).
Nseyo et al., "Study of factors mediating effect of photodynamic therapy on bladder in canine bladder model", *Urology,* 32(1):41-45 (1988).
Nseyo et al., "Whole bladder photodynamic therapy for transitional cell carcinoma of bladder", *Urology,* 26(3):274-280 (1985).
Nseyo et al., "Photodynamic therapy in the management of resistant lower urinary tract carcinoma", *Cancer* 60:3113-3119 (1987).
Nseyo et al., "Photodynamic therapy (PDT) in the treatment of patients with resistant superficial bladder cancer: a long-term experience", *Journal of Clinical Laser Medicine Surgery,* 16(1):61-68 (1998).
Nseyo et al., "Dihematoporphyrin ether clearance in primate bladders", *The Journal of Urology,* 136:1363-1366 (1986).
Nseyo et al., "Experimental photodynamic treatment of canine bladder", *J Urol.,* 133(2):311-315 (1985).
Paajanen et al., "Proton Relaxation Enhancement of Albumin, Immunoglobulin G, and Fibrinogen Labeled with Gd-DTPA",*Magn. Reson. Med* 13: 38-43 (1990).
Pandey et al., "Synthesis and photosensitizing activity of a di-porphyrin ether", *Chemical Abstracts* 109:320 (1988).
Pandey et al., "Synthesis, photophysical properties, in vivo photosensitizing efficacy, and human serum albumin binding properties of some novel bacteriochlorins", *J. Med. Chem.* 40(17):2770-2779 (1997).
Pandey et al., "Chlorin and porphyrin derivatives as potential photosensitizers in photodynamic therapy", *Photochemistry and Photobiology* 53(1):65-72 (1991).
Pandey et al. (1999).
Pandey et al., "Syntheses and photosensitizing activity of porphyrins joined with ester linkages", *Cancer Research* 49:2042-2047 (1989).
Pandey et al., "Evaluation of new benzoporphyrin derivatives with enhanced PDT efficacy", *Photochemistry and Photobiology* 62(4):764-768 (1995).
Pandey et al., "Alkyl ether analogs of chlorophyll-a derivatives: Part 1. Synthesis, photophysical properties and photodynamic efficacy", *Photochemistry and Photobiology* 64(1):194-204 (1996).
Pandey et al., "Porphyrin dimers as photosensitizers in photodynamic therapy", *J. Med. Chem.* 33:2032-2038 (1990).
Pandey et al., "Fast atom bombardment mass spectral analyses of Photofrin II and its synthetic analogs", *Biomedical and Environmental Mass Spectrometry* 19:405-414 (1990).
Pandey et al., "Comparative in vivo sensitizing efficacy of porphyrin and chlorin dimers joined with ester, ether, carbon-carbon or amide bonds" *Journal of Molecular Recognition* 9:118-122 (1996).
Pierce Chemical Co. catalog, pp. O-90 to O-110 (1995, Pierce Chemical Co., 3747 N. Meridian Rd., Rockford III., 61105, U.S.A.).
Polin, R.A. "Monoclonal Antibodies Against Microorganisms", *Eur. J. Clin. Microbiol.,* 3(5): 387-398 (1984).
Potter et al., "The theory of photodynamic therapy dosimetry: consequences of photo-destruction of sensitizer", *Photochemistry and Photobiology* 46(1):97-101 (1987).
Potter et al., "Photofrin II levels by in vivo fluorescence photometry", *Prog Clin Biol Res.* 170:177-186 (1984).
Potter et al., "Parabolic quantitative structure-activity relationships and photodynamic therapy: application of a three-compartment model with clearance to the in vivo quantitative structure-activity relationships of a congeneric series of pyropheophorbide derivatives used as photosensitizers for photodynamic therapy", *Photochemistry and Photobiology* 70(5):781-788 (1999).
Prakash, G.K.S. and A.K. Yudin, "Perfluoralkylation with Organosilicon Reagents", *Chem Rev.,* 97:757-786 (1997).
Pykett, "NMR Imaging in Medicine", *Scientific American* 246: 78 (1982).
Rakestraw, et al., "Antibody-targeted photolysis: In vitro studies with Sn(IV) chlorin e6 covalently bound to monoclonal antibodies using a modified dextran carrier", *Proc. Nad. Acad. Sci. USA* 87: 4217-4221 (1990).
Ris et al., "Absence of rhodamine 123-photochemotoxicity in human tumor xenografts", *Lasers Surg Med.* 13(1):40-44 (1993).
Roy et al., "Ceramic-Based Nanoparticles Entrapping Water-Insoluble Photosensitizing Anticancer Drugs: A Novel Drug-Carrier System for Photodynamic Therapy", *J Am Chem Soc.* 125(26):7860-7865 (2003).
Runfola et al., "Photodynamic therapy for residual neoplasms of the perianal skin", *Dis Colon Rectum.* 43(4):499-502 (2000).
Runge et al., "Paramagnetic Agents for Contrast-Enhanced NMR Imaging: A Review", *Am. J. Radiol.* 141: 1209 (1983).
Rungta et al., "Purpurinimides as photosensitizers: effect of the presence and position of the substituents in the in vivo photodynamic efficacy", *Bioorg Med Chem Lett.* 10(13):1463-1466 (2000).
Schuh et al., "Photodynamic therapy for palliation of locally recurrent breast carcinoma", *Journal of Clinical Oncology* 5(11):1766-1770 (1987).
Senge et al., "Comparative Analysis of the Conformations of Symmetrically and Asymmetrically Deca- and Undecasubstituted Porphyrins Bearing Meso-Alkyl or -Aryl Groups", *Inorg. Chem.,* 36:1149-1163 (1997).

Sery et al., "Photoradiation of rabbit ocular malignant melanoma sensitized with hematoporphyrin derivative", *Curr Eye Res.* 3(4):519-528 (1984).
Sharman et al., "Photodynamic therapeutics: basic principles and clinical applications", *Curr. Trends Drug Discovery Today* 4, 507 (1999).
Siegel et al., "Comparative mass spectrometric analyses of Photofrin oligomers by fast atom bombardment mass spectrometry, UV and IR matrix-assisted laser desorption/ionization mass spectrometry, electrospray ionization mass spectrometry and laser desorption/jet-cooling photoionization mass spectrometry", *J Mass Spectrom.* 34(6):661-669 (1999).
Simpson et al., Isolation and partial characterization of the tegumental outer membrane of adult *Schistosoma mansoni,Parasitology* 83: 163-177 (1981).
Singh et al., "Thiocarbamate linkage as internucleoside bond", *Indian J Biochem Biophys.* 33(5):425-427 (1996).
Smith et al., "Passive immunization of mice against *Schistosoma mansoni* with an IgM monoclonal antibody",*Parasitology* 84: 83-91 (1982).
Smith, et al., "Meso Substitution of Chlorophyll Derivatives: Direct Route for Transformation of Bacteriopheophorbides *d* into Bacteriopheophorbides *c", J. Am. Chem. Soc.* 107: 4946-4954 (1985).
Svaasand et al., "Temperature rise during photoradiation therapy of malignant tumors", *Med Phys.* 10(1):10-17 (1983).
Takita et al., "Intracavitary photodynamic therapy for malignant pleural mesothelioma", *Semin Surg Oncol.* 11:368-371 (1995).
Takita et al., "Operation and intracavitary photodynamic therapy for malignant pleural mesothelioma: a phase II study", *Ann Thorac Surg.* 58(4):995-998 (1994).
Tsuchida et al., "Correlation between site II—specific human serum albumin (HSA) binding affinity and murine in vivo photosensitizing efficacy of some Photofrin components", *Photochemistry and Photobiology* 66(2):224-228 (1997).
Umemura et al., *Ultrasonics Sonochemistry* 3: S187-S191 (1996).
Van Lier, J.E. "Photosensitization: Reaction Pathways", *Photobiological Techniques* 216: 85-98 (1991).
Vincent et al., "Photoradiation therapy in advanced carcinoma of the trachea and bronchus", *Chest,* 85(1):29-33 (1984).
Vincent et al., "Hematoporphyrin derivative in the diagnosis and treatment of lung cancer", *Adv Exp Med Biol.* 160:41-46 (1983).
Waldow et al., "Interaction of hyperthermia and photoradiation therapy" *Radiat Res.* 97(2):380-385 (1984).
Waldow et al., "Potentiation of photodynamic therapy by heat: effect of sequence and time interval between treatments in vivo", *Lasers Surg Med.* 5(2):83-94 (1985).
Waldow et al., "Enhanced tumor control following sequential treatments of photodynamic therapy(PDT) and localized microwave hyperthermia in vivo", *Lasers Surg Med.* 4(1):79-85 (1984).
Waldow et al., "Hyperthermic potentiation of photodynamic therapy employing Photofrin I and II: comparison of results using three animal tumor models", *Lasers Surg Med.* 7(1):12-22 (1987).
Weishaupt et al., "Identification of singlet oxygen as the cytotoxic agent in photoinactivation of a murine tumor", *Cancer Res.,* 36(7 PT 1):2326-2329 (1976).
Wilson et al., "The physics of photodynamic therapy," *Phys. Med. Biol.,* 31(4):327-360 (1986).
Wilson et al., "Photodynamic therapy for the treatment of basal cell carcinoma", *Arch Dermatol.* 128:1597-1601 (1992).
Wood et al., "A beam-splitting device for use with fiber-coupled laser light sources for photodynamic therapy", *Photochem Photobiol.,* 76(6):683-685 (2002).
Yoshida et al., "Hybridoma Produces Protective Antibodies Directed Against the Sporozoite Stage of Malaria Parasite", *Science* 207:71-73 (1980).
Yumita et al., Sonodynamically induced antitumor effect of gallium-porphyrin complex by focused ultrsound on experimental kidney tumor *Cancer Letters* 1,2: 79-86 (1997).
Yumita et al., "The Comination Treatment of Ultrasound and Anti-tumor Drugs on Yoshida Sarcoma", *Japan J. Hyperthermic Oncology* 3(2):175-182 (1987).
Zheng et al., "A Simple and Short Synthesis of Divinyl Chlorophyll Derivatives", *J Org Chem.* 64:3751-3754 (1999).
Zheng et al., "Synthesis of beta-galactose-conjugated chlorins derived by enyne metathesis as galectin-specific photosensitizers for photodynamic therapy", *J Org Chem.* 66(26):8709-8716 (2001).
Zheng et al., "Synthesis, photophysical properties, tumor uptake, and preliminary in vivo photosensitizing efficacy of a homologous series of 3-(1'-alkyloxy)ethyl-3-devinylpurpurin-18-N-alkylimides with variable lipophilicity", *J Med Chem.* 44:1540-1559 (2001).
Zheng et al., "Photosensitizers related to purpurin-18-*N*-alkylimides: a comparative in vivo tumoricidal ability of ester versus amide functionalities", *Bioorganic & Medicinal Chemistry Letters,* 10:123-127 (2000).
Zheng et al., "Wittig reactions on photoprotoporphyrin IX: new synthetic models for the special pair of the photosynthetic reaction center", *J Org Chem.* 65(2):543-557 (2000).
Zodda et al., Monoclonal Antibody-Mediated Protection against *Schistosoma mansoni* Infection in Mice, *J. Immunol.* 129: 2326-2328 (1982).
Valenzo et al. eds. (1991).

* cited by examiner

FIGURE 5A
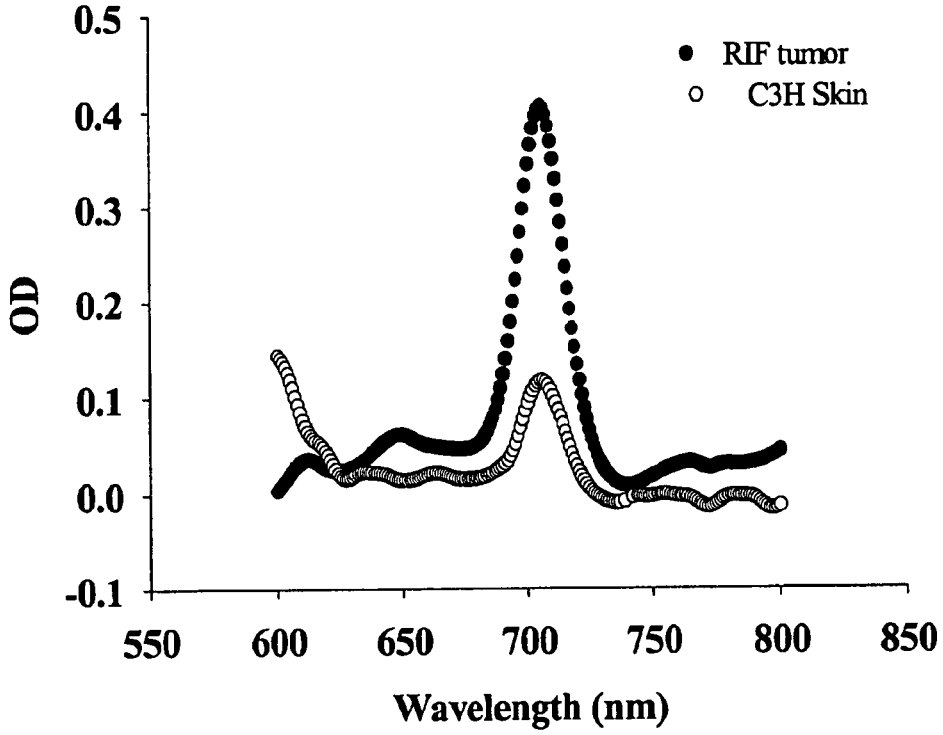
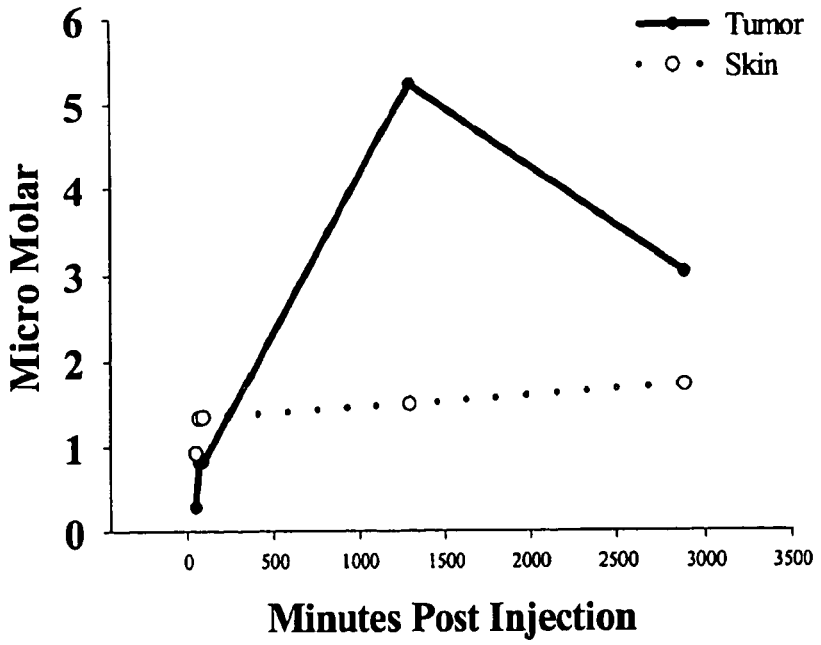
FIGURE 5B

FIGURE 6A
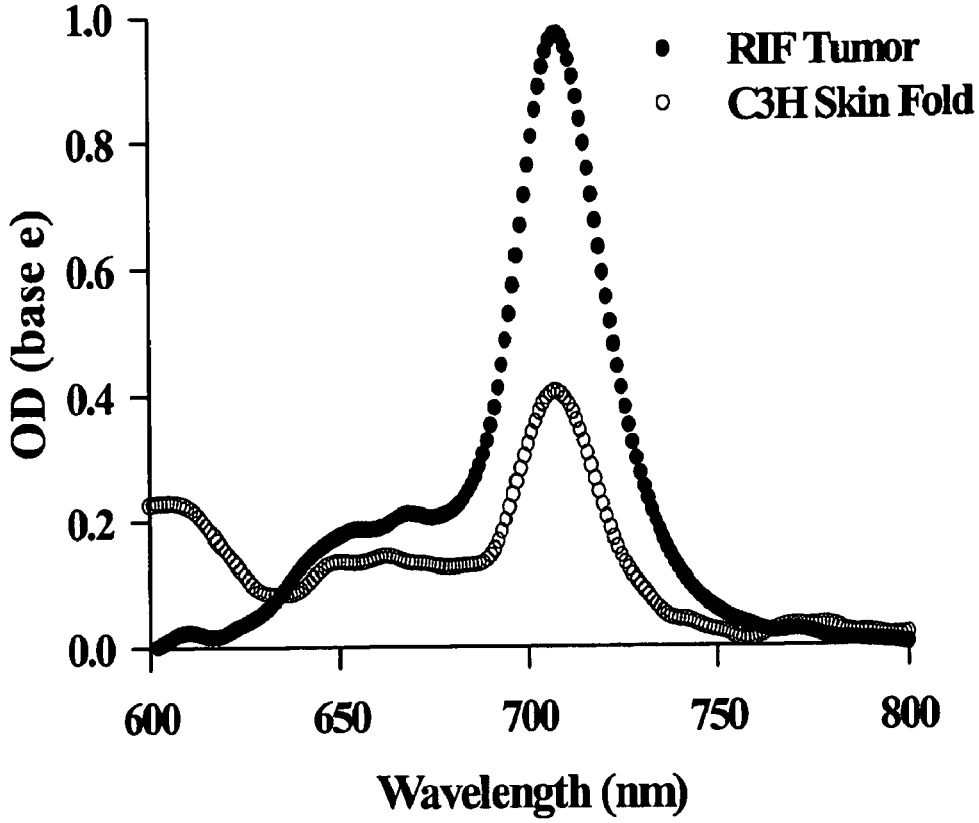
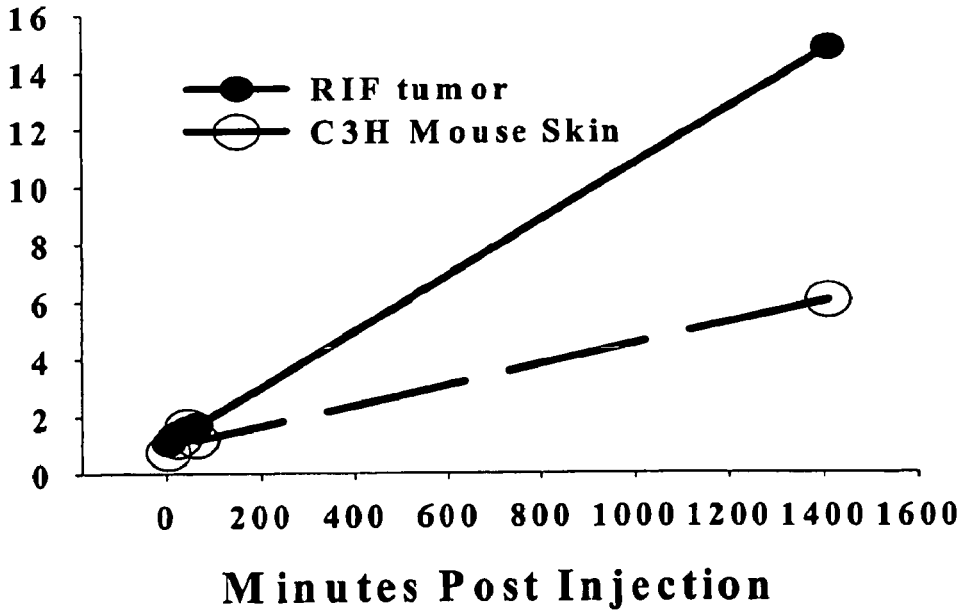
FIGURE 6B

FIGURE 7A
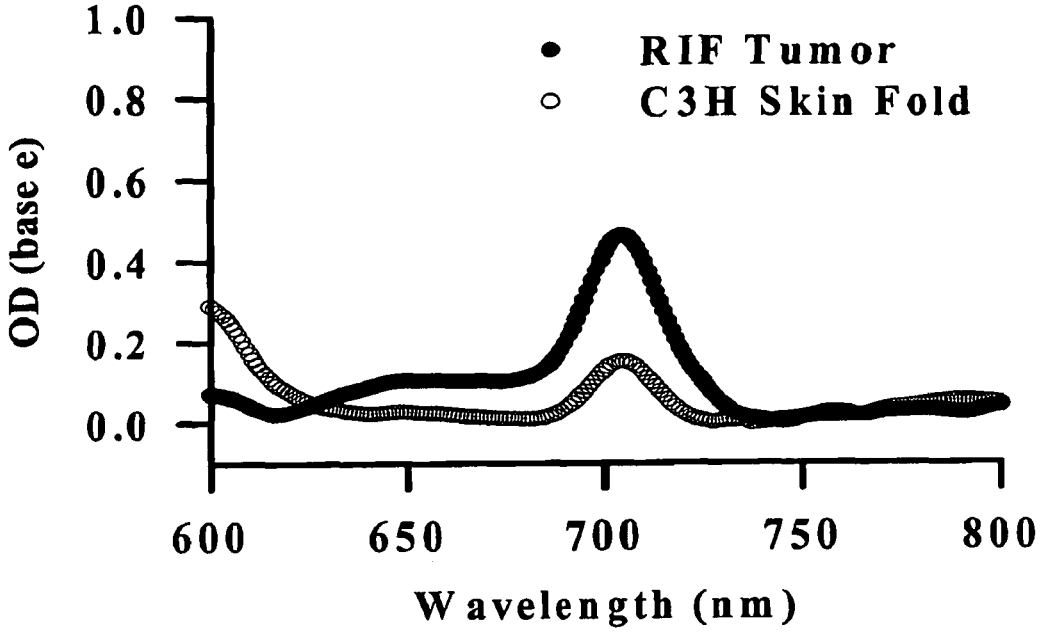
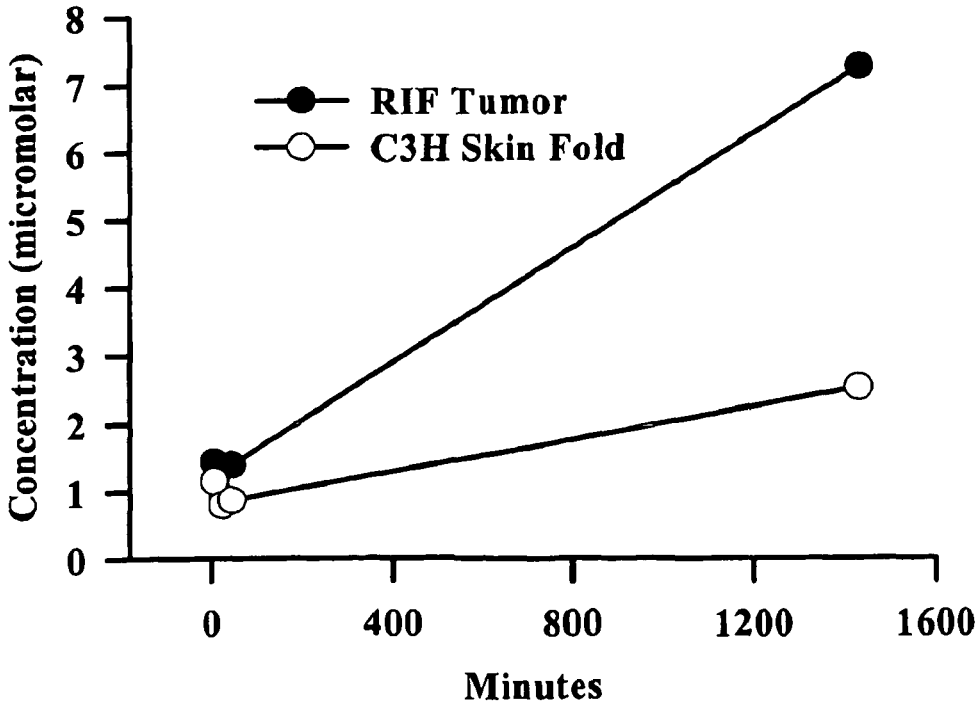
FIGURE 7B

FIGURE 8A
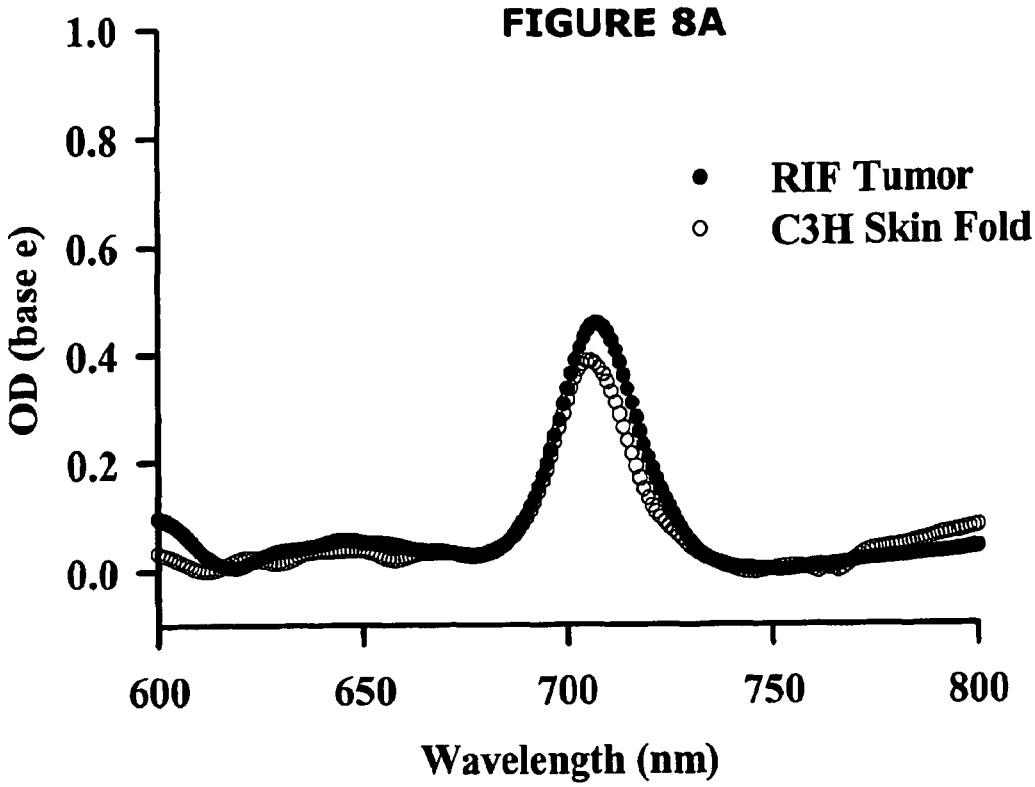
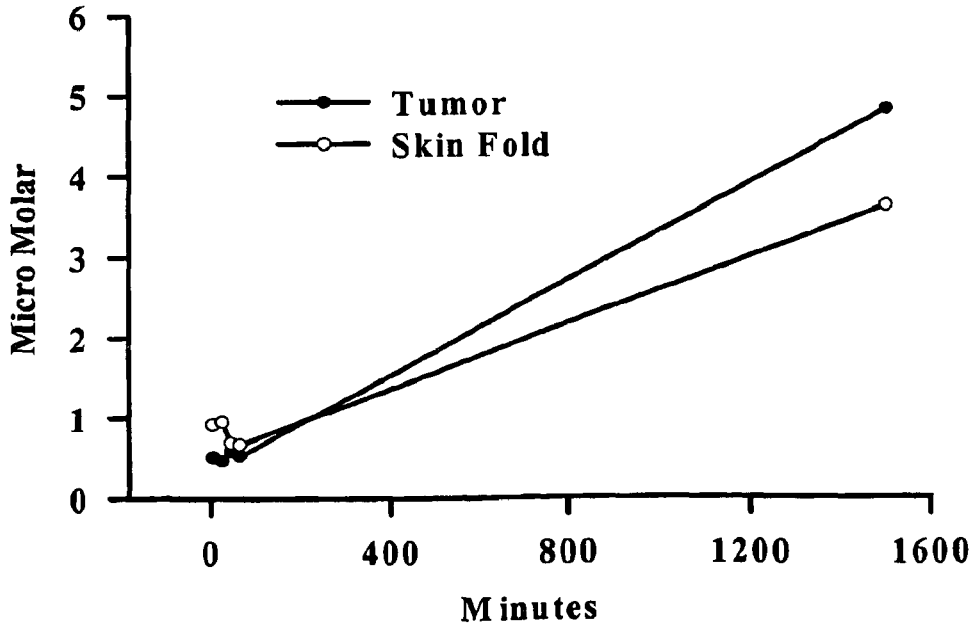
FIGURE 8B

FIGURE 11A
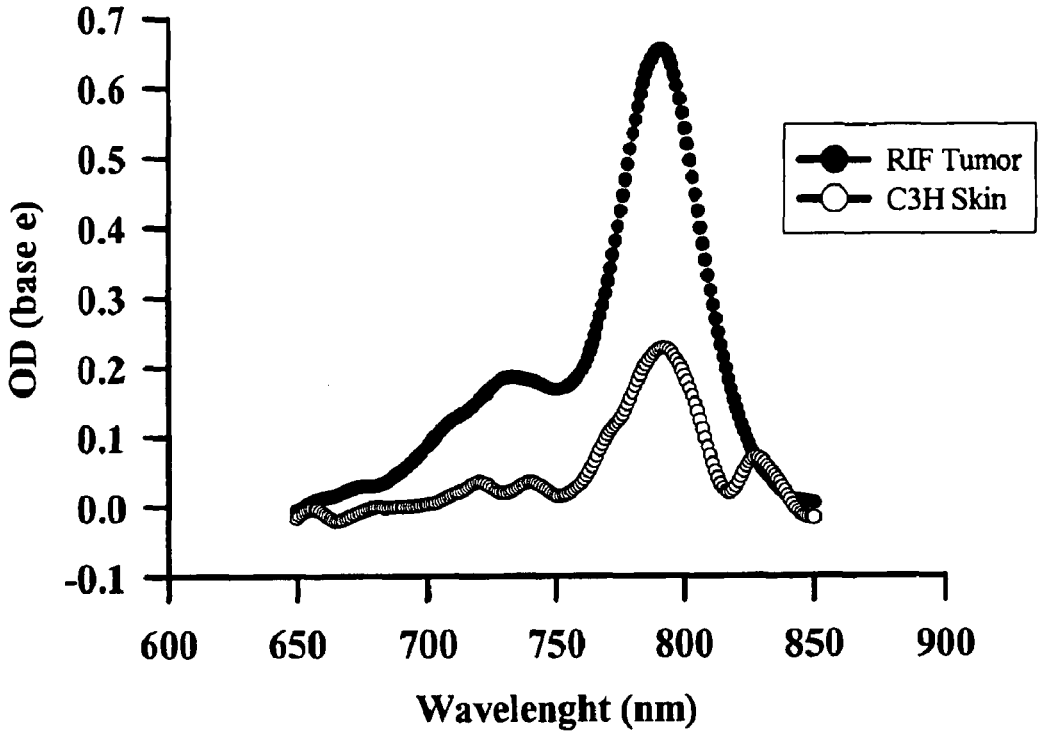
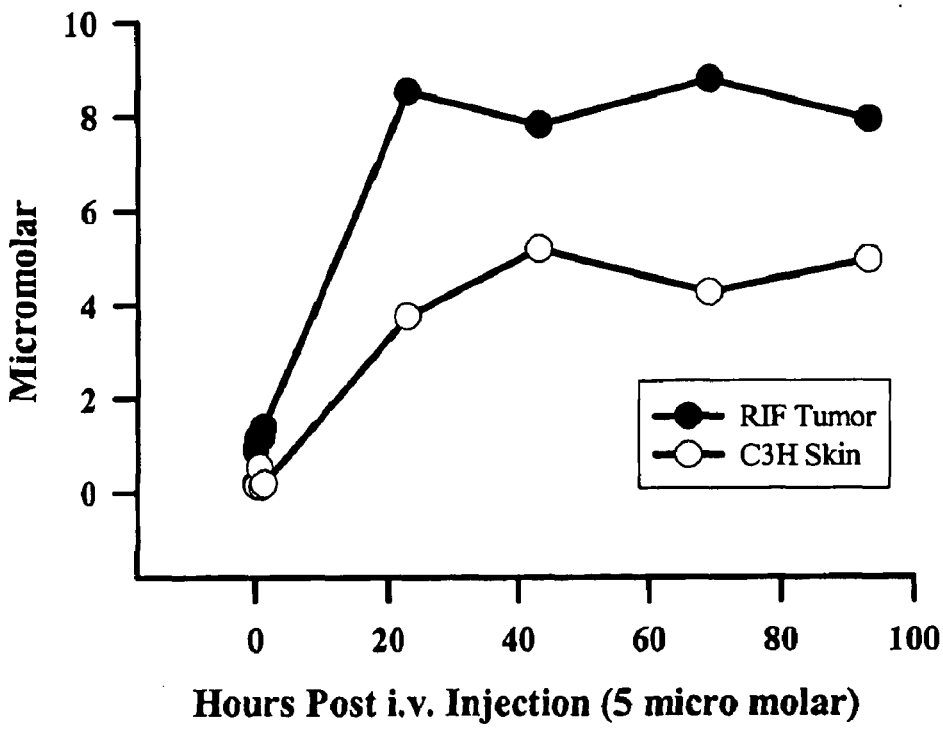
FIGURE 11B

FIGURE 12A
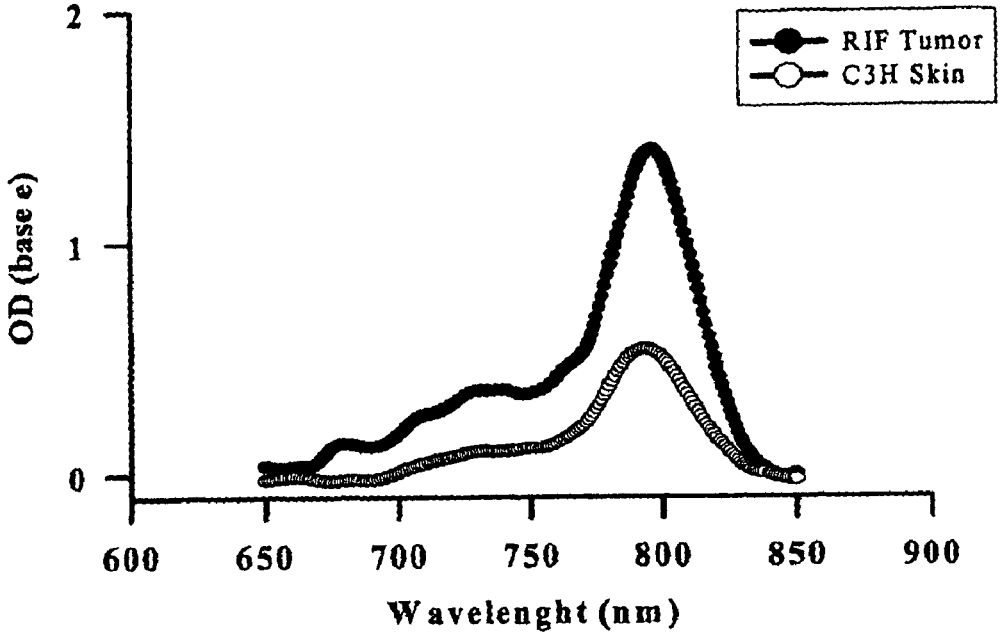
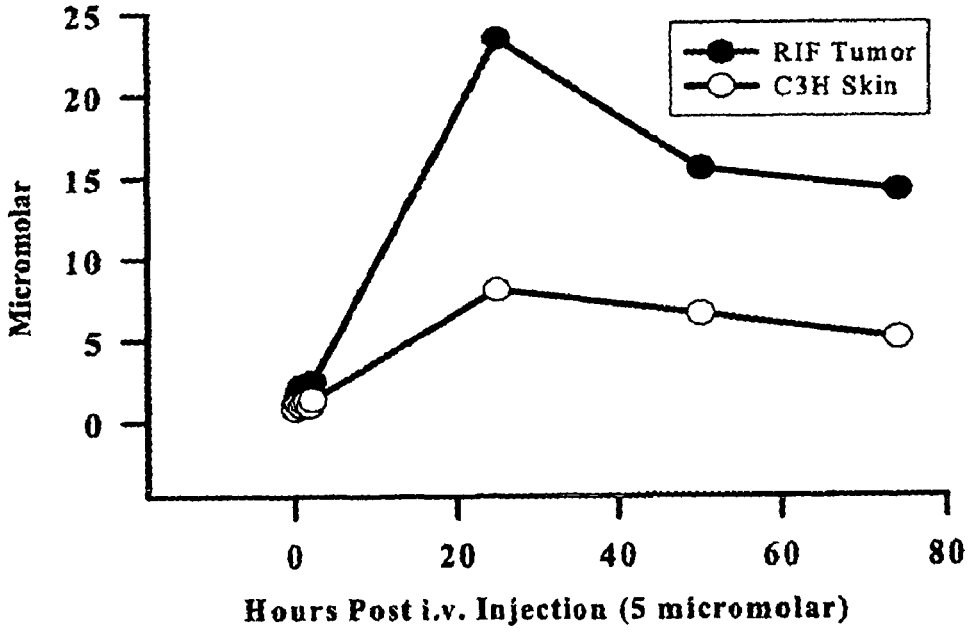
FIGURE 12B

FLUORINATED PHOTOSENSITIZERS RELATED TO CHLORINS AND BACTERIOCHLORINS FOR PHOTODYNAMIC THERAPY

Matter enclosed in heavy brackets [ ] appears in the original patent but forms no part of this reissue specification; matter printed in italics indicates the additions made by reissue.

RELATED APPLICATIONS

Benefit of priority under 35 U.S.C. § 119(e) to the following provisional application is claimed herein: U.S. provisional application 60/392,473 to Pandey et al., filed Jun. 27, 2002, entitled "FLUORINATED PHOTOSENSITIZERS RELATED TO CHLORINS AND BACTERIOCHLORINS FOR PHOTODYNAMIC THERAPY."

The above-noted provisional application is incorporated by reference herein in its entirety.

STATEMENT REGARDING FEDERALLY SPONSORED RESEARCH

This invention was made with funding from the National Institute of Health Grant Number NIH CA55791. The United States Government may have certain rights in this invention.

FIELD

Provided herein are compounds for detection, diagnosis and treatment of target tissues or target compositions, including hyperproliferative tissues such as tumors, using photodynamic methods. In particular, photosensitizer compounds that collect in hyperproliferative tissue are provided. In another embodiment, compounds that absorb light at a wavelength of from about 700 to about 850 nm are provided. In a further embodiment, compounds that are detectable by magnetic resonance imaging are provided.

BACKGROUND

Photodynamic therapy ("PDT") is a process whereby light of a specific wavelength is directed to tissues undergoing treatment or investigation that have been rendered photosensitive through the administration of a photoreactive or photosensitizing agent. The objective of the intervention may be either diagnostic, where the wavelength of light is selected to cause the photoreactive agent to fluoresce, thus yielding information about the tissue without damaging the tissue, or therapeutic, where the wavelength of light delivered to the photosensitive tissue under treatment causes the photo-reactive agent to undergo a photochemical interaction with oxygen in the tissue under treatment that yields high energy species, such as singlet oxygen, causing local tissue lysing or destruction. The method of van Lier (Photobiological Techniques 216: 85-98 (Valenzo et al. eds. 1991)) can be used to confirm the ability of any given compound to generate singlet oxygen effectively, thus making it a good candidate for use in photodynamic therapy.

In photodynamic therapy, a photosensitizer compound that demonstrates the ability to selectively accumulate in target tissue, such as neoplastic or hyperproliferative tissue, is administered to a subject, and when the photosensitizer accumulates in or preferentially associates with the target tissue, the target tissue becomes sensitized to photoradiation. The photo-sensitizing agent can be activated either coherent (laser) or non-coherent (non-laser) light. It is currently accepted that following absorption of light, the photosensitizer is transformed from its ground singlet state (P) into an electronically excited triplet state ($^3P^*$; $\tau \sim 10^{-2}$ sec.) via a short-lived excited singlet state ($^1P^*$; $\tau \sim 10^{-6}$ sec.) The excited triplet can undergo non-radiative decay or participate in an electron transfer process with biological substrates to form radicals and radical ions, which can produce singlet oxygen and superoxide ($O_2^-$) after interaction with molecular oxygen ($O_2$). Singlet oxygen can be produced from molecular oxygen by the transfer of energy directly or indirectly from the activated photosensitizer Singlet oxygen is one of the agents responsible for cellular and tissue damage in PDT, causing oxidation of the target tissue; there also is evidence that the superoxide ion may be involved. The generation of these cytotoxic agents plays a role in tumor homeostasis and the observed tumor destruction.

Photodynamic therapy has proven to be very effective in destroying abnormal tissue such as cancer cells. In this therapy, a photoreactive agent having a characteristic light absorption wavelength or waveband is first administered to the patient, typically either orally or by injection. Abnormal tissue in the body is known to selectively absorb certain photoreactive agents to a much greater extent than normal tissue, e.g., tumors of the pancreas and colon may absorb two to three times the volume of these agents, compared to normal tissue. Certain porphyrins and related tetrapyrrolic compounds tend to localize in abnormal tissue, including malignant tumors and other hyperproliferative tissue, such as hyperproliferative blood vessels, at much higher concentrations than in normal tissues, so they are useful as a tool for the treatment of various type of cancers and other hyperproliferative tissue by photodynamic therapy (PDT) (T. J. Dougherty, C. J. Gomer, B. W. Henderson, G. Jori, D. Kessel, M. Kprbelik, J. Moan, Q. Peng, J. Natl. Cancer Inst. 90: 889 (1998), incorporated here by reference). However, most of the porphyrin-based photosensitizers including PHOTOFRIN® (a purified hematoporphyrin derivative (HpD) approved worldwide for the treatment of tumors) clear slowly from normal tissue, so patients must avoid exposure to sunlight for a significant time after treatment.

PDT with PHOTOFRIN® has been used to treat a multiplicity of tumors accessible to light, including skin, lung, bladder, head and neck, breast, gastric, cervical and esophageal cancers. PHOTOFRIN® has some desirable characteristics, including good efficacy, water solubility, good yield of singlet oxygen, and ease of manufacture. However, PHOTOFRIN® has some disadvantageous properties: (i) it is a complex mixture of porphyrin dimers and higher oligomers linked by ether, ester, and/or carbon-carbon bonds and, therefore is difficult to study; (ii) it shows skin phototoxicity in patients for four to six weeks after administration; and (iii) due to its relatively weak absorbance in the red region (630 nm), lack of penetration of light through tissue limits current clinical applications of PHOTOFRIN® in PDT to the destruction of cancerous tissue less than 4 mm from the source of light used in the therapy.

Thus, there is a need for additional photosensitizers for use in PDT, diagnostic and therapeutic applications.

SUMMARY

Provided herein are fluorinated compounds for use in PDT, diagnostic and therapeutic applications. In one embodiment, the compounds preferentially absorb into target tissue, including hyperproliferative tissue. In another embodiment, the compounds absorb light at a wavelength of between about 700 and about 850 nm.

In one embodiment, provided herein are tetrapyrrole compounds containing a fluorinated substituent where the compound is a chlorin or bacteriochlorin.

[Also provided herein are compounds of the formula:

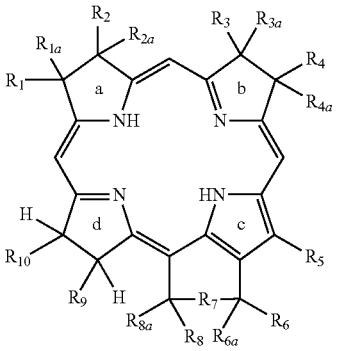

or a pharmaceutically acceptable derivative thereof, where $R_1$, $R_{1a}$, $R_2$, $R_{2a}$, $R_3$, $R_{3a}$, $R_4$, $R_{4a}$, $R_5$, $R_6$, $R_{6a}$, $R_8$, $R_{8a}$, $R_9$, and $R_{10}$ are independently hydrogen, lower alkyl of about 1 through 8 carbon atoms, lower alkenyl of about 1 through 8 carbon atoms, or lower alkyl of about 1 through 8 carbon atoms substituted with at least one halogen, hydroxy, carboxy, ester, aromatic, heterocyclic, ether, amide, or amine group; where two $R_1$, $R_{1a}$, $R_2$, $R_{2a}$, $R_4$, $R_{4a}$, $R_6$, $R_{6a}$, $R_8$, $R_{8a}$ $R_9$ and $R_{10}$ groups on adjacent carbon atoms may be taken together to form a covalent bond or two $R_1$, $R_{1a}$, $R_2$, $R_{2a}$, $R_3$, $R_{3a}$, $R_4$, $R_{4a}$, $R_6$, $R_{6a}$, $R_8$, and $R_{8a}$ groups on the same carbon atom may form a double bond to a divalent pendant group; $R_1$ or $R_2$ may additionally be —CH═$CH_2$, —CHO, —COOH, —$COOR_a$, or

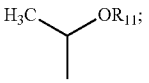

$R_7$ is —$CH_2$—, or ═$NR_{12}$, or a covalent bond, where $R_{11}$ and $R_{12}$ are independently hydrogen, lower alkyl of about 1 through 8 carbon atoms, lower alkenyl of about 1 through 8 carbon atoms, or lower alkyl of about 1 through 8 carbon atoms substituted with at least one halogen, hydroxy, carboxy, ester, aromatic, heterocyclic, ether, amino acid, amide, or amine group; provided that at least one of $R_1$, $R_{1a}$, $R_2$, $R_{2a}$ $R_3$, $R_{3a}$, $R_4$, $R_{4a}$, $R_5$, $R_5$, $R_6$, $R_{6a}$ $R_7$, $R_8$, $R_{8a}$, $R_9$ and $R_{10}$ contains at least one fluorinated pendant group selected from the group consisting of fluorinated alkyl groups, fluorinated phenyl groups and fluorinated heterocyclic moieties.]

*A compound of the formula:*

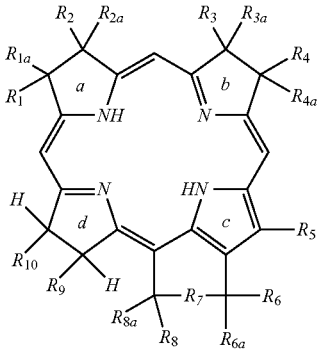

*wherein:*

*the compound is pharmaceutically acceptable;*

*$R_1$ and $R_2$ are each independently alkyl, alkenyl, —C(O)$R_a$ or —$COOR_a$ or —CH($CH_3$)($OR_a$) or —CH($CH_3$)(O($CH_2$)$_n$ $XR_a$) where $R_a$ is hydrogen, alkyl, alkenyl, alkynyl, or cycloalkyl; where $R_2$ may also be, —C(═$NR_{21}$)$CH_3$, or —CH($NHR_{21}$)$CH_3$;*

*where X is an aryl or heteroaryl group;*

*n is an integer of 0 to 6;*

*$R_{21}$ is 3,5-bis(trifluoromethyl)benzyl;*

*$R_{1a}$ and $R_{2a}$ are each independently hydrogen or substituted or unsubstituted alkyl, or together form a covalent bond;*

*$R_3$ and $R_4$ are each independently hydrogen or substituted or unsubstituted alkyl;*

*$R_{3a}$ and $R_{4a}$ are each independently hydrogen or substituted or unsubstituted alkyl, or together form a covalent bond;*

*$R_5$ is hydrogen or substituted or unsubstituted alkyl;*

*$R_6$ and $R_{6a}$ are each independently hydrogen or substituted or unsubstituted alkyl, or together form ═O;*

*$R_7$ is a covalent bond, alkylene, azaalkyl, or azaaraalkyl or*

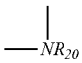

*where $R_{20}$ is 3,5-bis(trifluoromethyl)benzyl;*

*$R_8$ and $R_{8a}$ are each independently hydrogen or substituted or unsubstituted alkyl or together form ═O;*

*$R_9$ and $R_{10}$ are each independently hydrogen, or substituted or unsubstituted alkyl and $R_9$ may be —$CH_2CH_2COOR^2$ where $R^2$ is an alkyl group that may be optionally substituted with one or more fluorine atoms;*

*each of $R_3$-$R_6$, $R_8$-$R_{10}$, $R_{1a}$-$R_{4a}$, $R_{6a}$, and $R_{8a}$ when substituted, is substituted with one or more substituents each independently selected from Q, where Q is alkyl, haloalkyl, halo, pseudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, or aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl;*

*each Q is independently unsubstituted or is substituted with one or more substituents each independently selected from $Q_1$, where $Q_1$ is alkyl, haloalkyl, halo, pseudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, aryl or $CONR_d$ $R_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl;*

*with the proviso that the compound contains at least one 3,5-bis(trifluoromethyl)benzyl group.*

Also provided are compounds of the formula

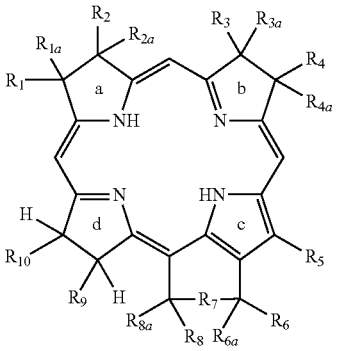

or a pharmaceutically acceptable derivative thereof, where $R_1$ and $R_2$ are each independently substituted or unsubstituted alkyl, substituted or unsubstituted alkenyl, —C(O)$R_a$ or —COO$R_a$, where $R_a$ is hydrogen, substituted or unsubstituted alkyl, substituted or unsubstituted alkenyl, substituted or unsubstituted alkynyl, or substituted or unsubstituted cycloalkyl; $R_{1a}$ and $R_{2a}$ are each independently hydrogen or substituted or unsubstituted alkyl, or together form a covalent bond; $R_3$ and $R_4$ are each independently hydrogen or substituted or unsubstituted alkyl; $R_{3a}$ and $R_{4a}$ are each independently hydrogen or substituted or unsubstituted alkyl, or together form a covalent bond; $R_5$ is hydrogen or substituted or unsubstituted alkyl; $R_6$ and $R_{6a}$ are each independently hydrogen or substituted or unsubstituted alkyl, or together form =O; $R_7$ is a covalent bond, alkylene, azaalkyl, or azaaralkyl; $R_8$ and $R_{8a}$ are each independently hydrogen or substituted or unsubstituted alkyl, or together form =O; $R_9$ and $R_{10}$ are each independently hydrogen, or substituted or unsubstituted alkyl; each of $R_1$-$R_{10}$, when substituted, is substituted with one or more substituents, in one embodiment one to five substituents, in another embodiment one, two or three substituents, each independently selected from Q, where Q is alkyl, haloalkyl, halo, pseudohalo, —COO$R_b$ where $R_b$ is hydrogen, alkyl, alkenyl, alkynyl, cycloalkyl or aryl, aryl, heteroaryl, cycloalkyl, heterocyclyl, O$R_c$ where $R_c$ is hydrogen, alkyl, alkenyl, alkynyl, cycloalkyl, aralkyl, or aryl, CON$R_d R_e$ where $R_d$ and $R_e$ are each independently hydrogen, alkyl, alkenyl, alkynyl, cycloalkyl or aryl, N$R_f R_g$ where $R_f$ and $R_g$ are each independently hydrogen, alkyl, alkenyl, alkynyl, cycloalkyl, aralkyl or aryl, =N$R_h$ where $R_h$ is alkyl, alkenyl, alkynyl, cycloalkyl, aralkyl or aryl, or is an amino acid residue; each Q is independently unsubstituted or is substituted with one or more substituents, in one embodiment one to five substituents, in another embodiment one, two or three substituents, each independently selected from $Q_1$, where $Q_1$ is alkyl, haloalkyl, halo, pseudohalo, —COO$R_b$ where $R_b$ is hydrogen, alkyl, alkenyl, alkynyl, cycloalkyl or aryl, aryl, heteroaryl, cycloalkyl, heterocyclyl, O$R_c$ where $R_c$ is hydrogen, alkyl, alkenyl, alkynyl, cycloalkyl or aryl, CON$R_d R_e$ where $R_d$ and $R_e$ are each independently hydrogen, alkyl, alkenyl, alkynyl, cycloalkyl or aryl, N$R_f R_g$ where $R_f$ and $R_g$ are each independently hydrogen, alkyl, alkenyl, alkynyl, cycloalkyl or aryl, or is an amino acid residue.

In another embodiment the compounds are selected with the proviso that the compound contains at least one fluorine atom.

Also provided are methods for detecting target tissue or target compositions. Further provided herein is a method for photodynamic therapy using the compounds provided herein.

Also provided herein is a method for detecting hyperproliferative tissue using the compounds provided herein.

Also provided is the use of the compounds provided herein for the treatment of target compositions or target tissue, including hyperproliferative tissue and neovascular tissue. Provided herein is also a method for detecting the presence of hyperproliferative tissue in a subject. Also provided is a method of diagnosing hyperproliferative disorders in a patient. Further provided is a method of diagnosing an infecting agent in a patient.

Provided herein is also a method of generating an image of a target tissue in a subject. Also provided herein is a method of labeling a target tissue for diagnostic radiology. Further provided is a kit to treat hyperproliferative disorders. Also provided is a kit to label specific tissues for diagnostic radiology. Further provided is a combination, including a compound provided herein and a light source. Further provided is a combination including a photosensitizer compound provided herein and a magnetic resonance imaging device.

BRIEF DESCRIPTION OF THE DRAWINGS

FIGS. 5A and 5B through 8A and 8B illustrate the selective tissue distribution of newly synthesized purpurinimide analogs 8, 9, 11 and 12, respectively, as addressed above in FIGS. 3 and 4.

FIGS. 11A and 11B and FIGS. 12A and 12B illustrate the selective tissue distribution of newly synthesized bacteriochlorins 16 and 18, respectively, addressed above in FIGS. 9 and 10.

DETAILED DESCRIPTION

A. Definitions

Figure 1:
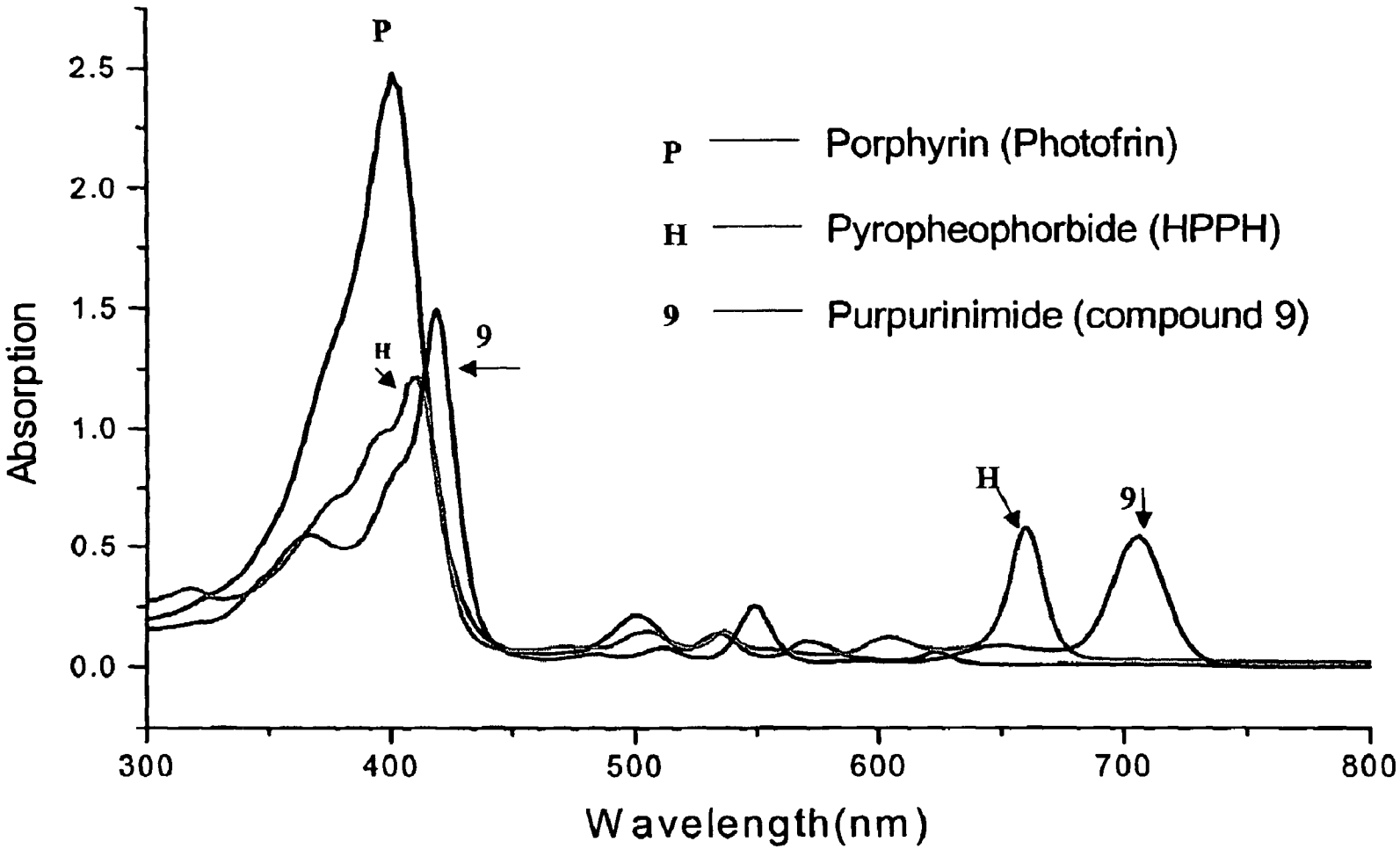
FIG. 1 illustrates the electronic absorption spectra of two chlorin based photosensitizers, with that of an existing product (PHOTOFRIN®) shown for comparison.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, the term "tetrapyrrole compound" denotes a macrocyclic compound containing four pyrrole rings, having the general structure:

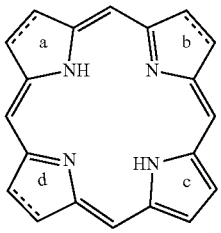

where the dashed line indicates that the indicated bond may be saturated or unsaturated, and where any atom of the ring may be substituted or unsubstituted.

As used herein, the term "porphyrin" refers to a cyclic structure typically composed of four pyrrole rings, and refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g phthalocyanines, porphyrazines, naphthalocyanines, subphthalocyanines, and porphyrin isomers).

As used herein, "chlorin" refers to a class of porphyrin derivatives having a cyclic structure typically composed of four pyrrole rings having one partially saturated pyrrole ring, such as the basic chromophore of chlorophyll.

As used herein, "bacteriochlorin" refers to a class of porphyrin derivatives having a cyclic structure typically composed of four pyrrole rings having two partially saturated non-adjacent (i.e., trans) pyrrole rings, and "isobacteriochlorin" includes those porphyrin derivatives having a cyclic structure typically composed of four pyrrole rings having two partially saturated adjacent (i.e., cis) pyrrole rings.

The principal oxidation states of various tetrapyrroles including porphyrin, chlorin, bacteriochlorin, pyropheophorbide, purpurpin and purpurinimide are illustrated below.

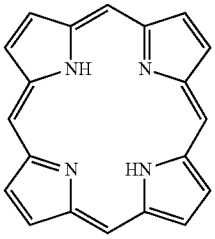

Porphyrin

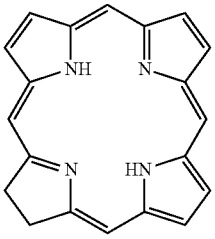

Chlorin

-continued

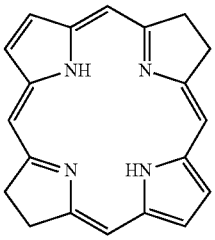

Bacteriochlorin

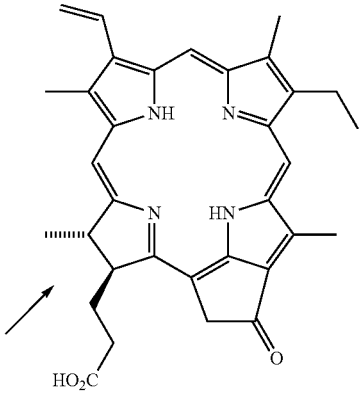

Chlorin(pyropheophorbide)

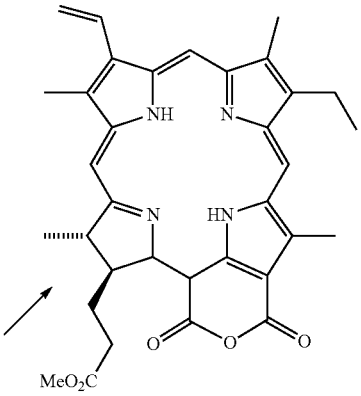

Chlorin(purpurin)

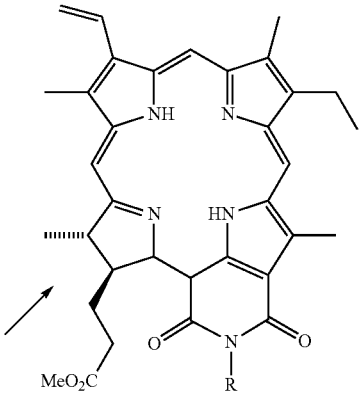

Chlorin (purpurinimide)

Various chlorins (structures A and B) and bacteriochlorins (structures C, D and E), are shown below, and exemplify the types of chlorins and bacteriochlorins provided herein.

Chlorins:

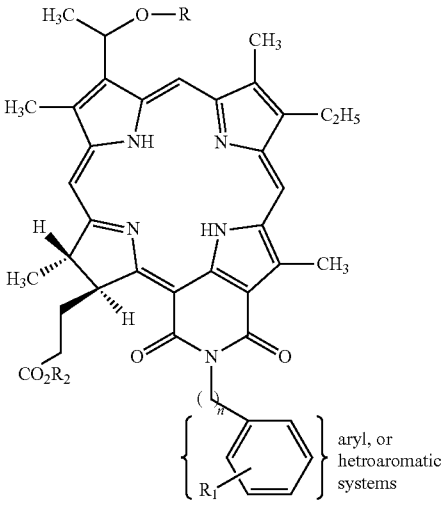

A

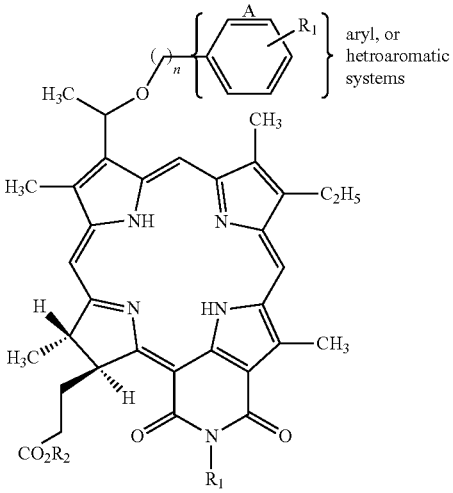

B

Bacteriochorins

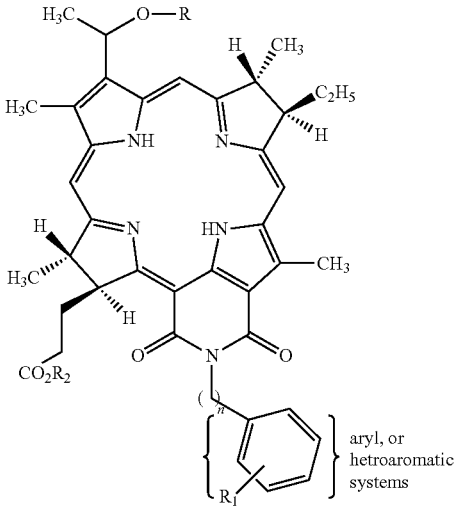

C

-continued

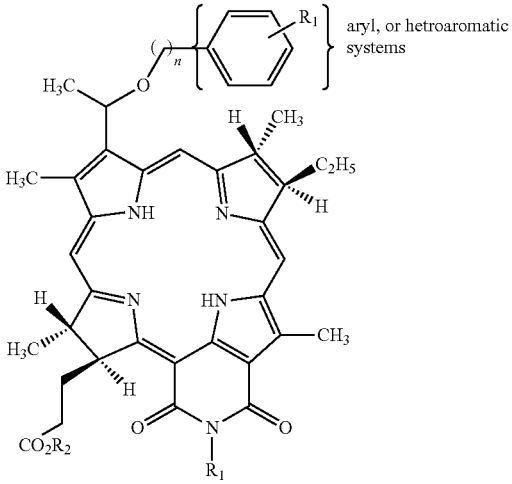

D

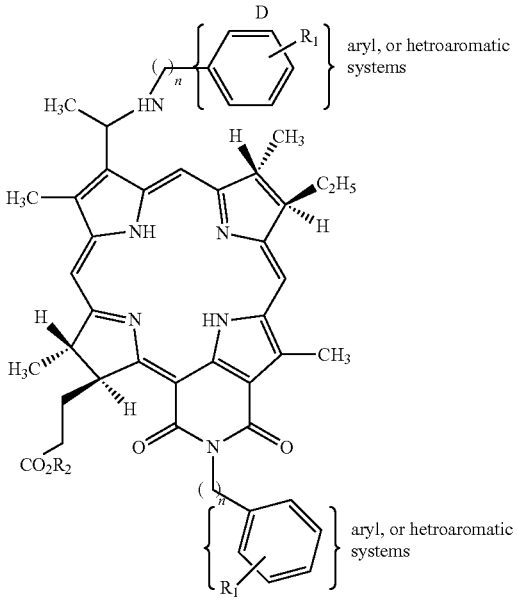

E

Where R and $R_1$ = Various alkyl with variable no. of carbon chains their fluorinated analogs, aromatic side chain with fluorinated or non-fluorinated substituents.

$R_2$ = Fluorinated or non-fluorinated ester groups with variable no. of carbon units, Fluorinated and non-fluorinated amide substituents.

As used herein, the recitation "fluorinated" and "fluorinated substituent" denotes replacing at least one atom of a molecule, a group or a substituent with at least one fluorine atom.

As used herein, the term "fluorine atom" denotes all naturally occurring isotopes of fluorine, including, for example, $^{19}F$.

As used herein, the term "heterocyclic group" generally refers to a monocyclic or multicyclic saturated, unsaturated, or aromatic carbocyclic group, in one embodiment of from 3 to 20 atoms, including at least one, and preferably a plurality of hetero atoms within the ring, wherein a hetero atom is an element other than carbon, (for example, including but not limited to N, O, S, Se, Te), which hetero atoms may be the same or different. The group may include five- or six-membered heterocyclic rings, polycyclic ring systems, optionally substituted aromatic ring systems having one or more heteroatoms and polyheteroaromatic ring systems where the ring system has from two to four, more preferably two to three, and most preferably two, rings having one or more hetero atom. The ring systems of the heterocyclic groups may be composed of one ring or two or more rings which may be joined together in a fused, bridged or spiro-connected fashion. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above. The heteroatom within the ring can optionally be unsubstituted or substituted with, e.g. halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 8 carbons.

As used herein, halogen refers to one of the electronegative elements of group VIIA of the periodic table (fluorine, chlorine, bromine, iodine, astatine).

As used herein, "hydroxy group" generally refers to a hydroxyl group having the formula —OH.

As used herein, "carboxy" generally refers to a divalent radical, —C(O)O—.

As used herein, "ester group" generally refers to a substituent of the general formula —C—O—O—$R^1$ where $R^1$ may be either aliphatic or aromatic.

As used herein, "aromatic group" generally refers to a ring structure having cyclic clouds of delocalized π electrons above and below the plane of the molecule, where the π clouds contain (4n+2)π electrons. A further discussion of aromaticity is found in Morrison and Boyd, Organic Chemistry, (5th Ed., 1987), Chapter 13, entitled "Aromaticity," pages 477-497, incorporated herein by reference.

As used herein, "ether group" generally refers to a compound in which an oxygen atom is bonded to two alkyl or two aryl groups, or one alkyl and one aryl group.

As used herein, "amide group" generally refers to the group —C(O)NRR where each R is independently aliphatic or aromatic.

As used herein, "amine group" has the general formula —NRR, where each R is independently any alkyl or aryl group.

As used herein, a fluorinated pendant group generally refers to any substituent that includes at least one fluorine atom.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, "cycloalkyl" refers to a saturated mono- or multi-cyclic ring system, in certain embodiments of 3 to 20 carbon atoms, in other embodiments of 3 to 10 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" and "heteroaromatic group" refers to a monocyclic or multicyclic aromatic ring system, in certain embodiments, of about 5 to about 20 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 20 members, in another embodiment of 4 to 10 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "carboxy" refers to a divalent radical, —C(O)O—.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(═O) and $S(═O)_2$ groups, or substituted or unsubstituted nitrogen atoms, including —NR— and —$N^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—$CH_2$—), ethylene (—$CH_2CH_2$—), propylene (—$(CH_2)_3$—), methylenedioxy (—O—$CH_2$—O—) and ethylenedioxy (—O—$(CH_2)_2$—O—). The term "lower alkylene" refers to alkylene groups having 1 to 6 carbons. In certain embodiments, alkylene groups are lower alkylene, including alkylene of 1 to 3 carbon atoms.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from $Q^1$.

Where the number of any given substituent is not specified (e.g., haloalkyl), there may be one or more substituents present. For example, "haloalkyl" may include one or more of the same or different halogens. As another example, "$C_{1-3}$ alkoxyphenyl" may include one or more of the same or different alkoxy groups containing one, two or three carbons.

As used herein, "amino acid residue" generally refers to an organic acid carrying an amino group, and are of a general formula $^+H_3N$—CHR—$COO^-$. As used herein, "amino acid" refers to natural or unnatural amino acids. The amino acids include but are not limited to 4-aminobutyric acid, 6-aminohexanoic acid, alanine, asparagine, aspartic acid, arginine, 3-cyclohexyl-alanine, citrulline, cysteine, 2,4-diaminobutyric acid, glutamine, glutamic acid, glycine, histidine, isoleucine, leucine, lysine, methionine, 3-(2-naphthyl)-alanine, norleucine, omithine, phenylalanine, 4-halogeno-phenylalanine, phenylglycine, proline, 3-(2-pyridyl)-alanine, serine, 3-(2-thienyl)-alanine, threonine, tryptophan, tyrosine and valine.

If the amino acids mentioned above can occur in several enantiomeric forms, such as the L- or D-form, then all of these forms and also their mixtures (e.g., the DL-forms) are included as constituents of the compounds disclosed herein. The configuration for naturally occurring amino acid residues is generally L. When not specified the residue is the L form. The amino acids, e.g., as constituents of compounds disclosed herein, may furthermore be provided with appropriate protective groups known to those skilled in the art. Preferred protecting groups are, for example, BOC (tert-butoxycarbonyl) and FMOC (9-fluorenylmethoxy-carbonyl) for the N-terminus and OMe (methyl ester) and OEt (ethyl ester) for the C-terminus of the amino acid radicals. As used herein, any abbreviations used for any protective groups, amino acids and other compounds, are, unless indicated otherwise, in accord with their common usage, recognized abbreviations, or the IUPAC-IUB Commission on Biochemical Nomenclature (see, Biochem. 11: 942-944 (1972)).

As used herein, treatment means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "antibodies and antibody fragments" refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

As used herein, an "infecting agent" denotes invading microbes or parasites. As used herein, "microbe" denotes virus, bacteria, rickettsia, mycoplasma, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like.

As used herein, "tumor" denotes a neoplasm, and includes both benign and malignant tumors. This term particularly includes malignant tumors which can be either solid (such as a breast, liver, or prostate carcinoma) or non-solid (such as a leukemia). Tumors can also be further divided into subtypes, such as adenocarcinomas (e.g. of the breast, prostate or lung).

As used herein, "a target" denotes the object that is intended to be detected, diagnosed, impaired or destroyed by the methods provided herein, and includes target cells, target tissues, and target compositions. "Target tissues" and "target cells" as used herein are those tissues that are intended to be impaired or destroyed by this treatment method. Photosensitizing compounds bind to these target tissues or target cells; then when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non-target cells.

"Non-target tissues" as used herein are all the tissues of the subject which are not intended to be impaired or destroyed by the treatment method. These non-target tissues include but are not limited to healthy blood cells, and other normal tissue, not otherwise identified to be targeted.

"Target compositions" as used herein are those compositions that are intended to be impaired or destroyed by this treatment method, and may include one or more pathogenic agents, including but not limited to bacteria, viruses, fungi, protozoa, and toxins as well as cells and tissues infected or infiltrated therewith. The term "target compositions" also includes, but is not limited to, infectious organic particles such as prions, toxins, peptides, polymers, and other compounds that may be selectively and specifically identified as an organic target that is intended to be impaired or destroyed by this treatment method.

"Hyperproliferative tissue" as used herein means tissue that grows out of control and includes neoplastic tissue, tumors and unbridled vessel growth such as blood vessel growth found in age-related macular degeneration and often occurring after glaucoma surgeries.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders includes, but are not limited to, cancers or carcinomas, acute and membrano-proliferative glomerulonephritis, myelomas, psoriasis, atherosclerosis, psoriatic arthritis, rheumatoid arthritis, diabetic retinopathies, macular degeneration, corneal neovascularization, choroidal hemangioma, recurrence of pterygii, and scarring from excimer laser surgery and glaucoma filtering surgery.

A "therapeutically effective dose" as used herein is a dose sufficient to prevent advancement, or to cause regression of the disease, or which is capable of relieving symptoms caused by the disease.

A "pharmaceutical agent" or "drug" refers to a chemical compound or composition capable of inducing a desired therapeutic or prophylactic effect when properly administered to a subject.

All chemical compounds include both the (+) and (−) stereoisomers, as well as either the (+) or (−) stereoisomer.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

While one preferred embodiment of the present invention is drawn to the use of light energy for administering PDT to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: galliumporphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

As used herein, destroy means to kill the desired target tissue or target composition, including infecting agents. "Impair" means to change the target tissue or target composition in such a way as to interfere with its function or reduce its growth. For example, in North et al., it is observed that after virus-infected T cells treated with benzoporphyrin derivatives were exposed to light, holes developed in the T cell membrane and increased in size until the membrane completely decomposed (Blood Cells 18:129-40 (1992)). The target tissue or target composition is understood to be impaired or destroyed even if the target tissue or target composition is ultimately disposed of by macrophages.

The present invention provides a method for providing a medical therapy to an animal, and the term "animal" includes, but is not limited to, humans and other mammals. The term "mammals" or "mammalian subject" includes farm animals, such as cows, hogs and sheep, as well as pet or sport animals such as horses, dogs, and cats.

The term "coupling agent" as used herein, refers to a reagent capable of coupling a photosensitizer to a targeting agent As used herein, "targeting agent" refers to a compound that homes in on or preferentially associates or binds to a particular tissue, receptor, infecting agent or other area of the body of the subject to be treated, such as a target tissue or target composition. Examples of a targeting agent include but are not limited to a ligand, one member of a ligand-receptor binding pair, and liposomal suspensions, including tissue-targeted liposomes.

As used herein, "specific binding pair" and "ligand-receptor binding pair" refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (anti-ligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-α and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and there receptors, such as granulocyte-macrophage colony stimulating factor (GMCSF) and GMCSF receptor and macrophage colony stimulating factor (MCSF) and MCSF receptor.

As used herein, the term "bind" or "binding" is used to refer to the binding between a targeting agent and its target, such as a ligand and its receptor, with a $K_d$ in the range of $10^{-2}$ to $10^{-15}$ mole/l, generally, $10^{-6}$ to $10^{-15}$, $10^{-7}$ to $10^{-15}$ and typically $10^{-8}$ to $10^{-15}$ (and/or a $K_a$ (binding affinity) of $10^5$-$10^{12}$, $10^7$-$10^{12}$, $10^8$-$10^{12}$ l/mole).

As used herein, specific binding or selective binding means that the binding of a targeting agent with its target, such as a particular ligand and its receptor is at least 2-fold, generally, 5, 10, 50, 100 or more-fold, greater than for non-target, such as another receptor. A statement that a particular compound is targeted to a target cell or target tissue means that its affinity for such cell or tissue in a host or in vitro or in vivo is at least about 2-fold, generally, 5, 10, 50, 100 or more-fold, greater than for other cells and tissues in the host or under the in vitro conditions.

As used herein, sample refers to anything that contains an target for which a target assay is desired. The sample can be a biological sample, such as a biological fluid or a biological tissue. Examples of biological fluids include urine, blood, plasma, serum, saliva, semen, stool, sputum, cerebral spinal fluid, tears, mucus, sperm, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, combination refers to any association between 2 or more items.

B. Compounds

Provided herein are tetrapyrrole compounds containing a fluorinated substituent where the compound is a chlorin or bacteriochlorin.

Also provided are compounds of the formula:

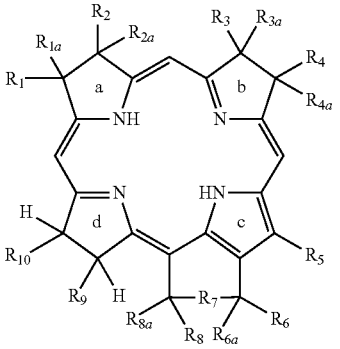

or a pharmaceutically acceptable derivative thereof, where $R_1$, $R_{1a}$, $R_2$, $R_{2a}$, $R_3$, $R_{3a}$, $R_4$, $R_{4a}$, $R_5$, $R_6$, $R_{6a}$, $R_8$, $R_{8a}$, $R_9$, and $R_{10}$ are independently hydrogen, lower alkyl of about 1 through 8 carbon atoms, lower alkenyl of about 1 through 8 carbon atoms, or lower alkyl of about 1 through 8 carbon atoms substituted with at least one halogen, hydroxy, carboxy, ester, aromatic, heterocyclic, ether, amide, or amine group; where two $R_1$, $R_{1a}$, $R_2$, $R_{2a}$, $R_4$, $R_{4a}$, $R_6$, $R_{6a}$, $R_8$, $R_{8a}$ $R_9$ and $R_{10}$ groups on adjacent carbon atoms may be taken together to form a covalent bond or two $R_1$, $R_{1a}$, $R_2$, $R_{2a}$, $R_3$, $R_{3a}$, $R_4$, $R_{4a}$, $R_6$, $R_{6a}$, $R_8$, and $R_{8a}$ groups on the same carbon atom may form a double bond to a divalent pendant group; $R_1$ or $R_2$ may additionally be —CH═$CH_2$, —CHO, —COOH, —$COOR_a$, or

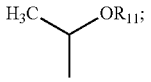

$R_7$ is —$CH_2$—, or ═$NR_{12}$, or a covalent bond, where $R_{11}$, and $R_{12}$ are independently hydrogen, lower alkyl of about 1 through 8 carbon atoms, lower alkenyl of about 1 through 8 carbon atoms, or lower alkyl of about 1 through 8 carbon atoms substituted with at least one halogen, hydroxy, carboxy, ester, aromatic, heterocyclic, ether, amide, or amine group; provided that at least one of $R_1$, $R_{1a}$, $R_2$, $R_{2a}$ $R_3$, $R_{3a}$, $R_4$, $R_{4a}$, $R_5$, $R_5$, $R_6$, $R_{6a}$ $R_7$, $R_8$, $R_{8a}$, $R_9$ and $R_{10}$ contains at least one fluorinated pendant group selected from the group consisting of fluorinated alkyl groups, fluorinated phenyl groups and fluorinated heterocyclic moieties.

Also provided are compounds where $R_9$ is —$CH_2CH_2CO_2R_a$, where $R_a$ is hydrogen or lower alkyl of 1-8 carbons.

Also provided are compound of the formula:

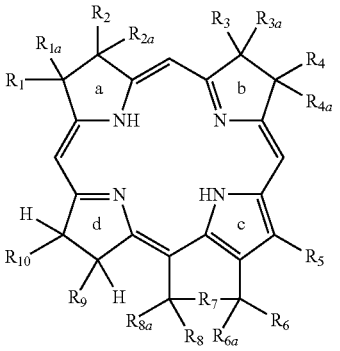

or a pharmaceutically acceptable derivative thereof, where $R_1$ and $R_2$ are each independently substituted or unsubstituted alkyl, substituted or unsubstituted alkenyl, —C(O)$R_a$ or —$COOR_a$, where $R_a$ is hydrogen, substituted or unsubstituted alkyl, substituted or unsubstituted alkenyl, substituted or unsubstituted alkynyl, or substituted or unsubstituted cycloalkyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form ═O;

$R_7$ is a covalent bond, alkylene, azaalkyl, or azaaralkyl;

$R_8$ and $R_{8a}$ are each independently hydrogen or substituted or unsubstituted alkyl, or together form ═O;

$R_9$ and $R_{10}$ are each independently hydrogen, or substituted or unsubstituted alkyl;

each of $R_1$-$R_{10}$, when substituted, is substituted with one or more substituents, in one embodiment one to five substituents, in another embodiment one, two or three substituents, each independently selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, ═$NR_h$ where $R_h$ is alkyl, alkenyl, alkynyl, cycloalkyl, aralkyl or aryl, or is an amino acid residue;

each Q is independently unsubstituted or is substituted with one or more substituents, in one embodiment one to five substituents, in another embodiment one, two or three substituents, each independently selected from $Q_1$, where $Q_1$, is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl or aryl, or is an amino acid residue;

with the proviso that the compound contains at least one fluorine atom.

Also provided are compounds where $R_1$ is substituted or unsubstituted alkyl;

$R_2$ is substituted or unsubstituted alkyl, substituted or unsubstituted alkenyl, or —C(O)$R_a$, where $R_a$ is substituted or unsubstituted alkyl;

$R_{1a}$ and $R_{2a}$ together form a covalent bond;

$R_3$ and $R_4$ are each independently substituted or unsubstituted alkyl;

$R_{3a}$ and $R_{4a}$ are each independently hydrogen, or together form a covalent bond;

$R_5$ is substituted or unsubstituted alkyl;

$R_6$ and $R_{6a}$ together form ═O;

$R_7$ is azaalkyl, or azaaralkyl;

$R_8$ and $R_{8a}$ together form ═O;

$R_9$ and $R_{10}$ are each independently substituted or unsubstituted alkyl;

each of $R_1$-$R_{10}$, when substituted, is substituted with one or more substituents each independently selected from Q, where Q is halo, pseudohalo, haloalkyl, $COOR_b$ where $R_b$ is hydrogen or alkyl, $OR_c$ where $R_c$ is alkyl or aralkyl, $NR_fR_g$ where $R_f$ and $R_g$ are each independently hydrogen, alkyl or aralkyl, or ═$NR_h$ where $R_h$ is aralkyl;

each Q is independently unsubstituted or is substituted with one or more substituents each independently selected from $Q_1$, where $Q_1$ is halo, pseudohalo, or haloalkyl.

Also provided are compounds where $R_1$ is unsubstituted alkyl;

$R_2$ is substituted or unsubstituted alkyl, unsubstituted alkenyl, or —$C(O)_a$, where $R_a$ is unsubstituted alkyl;

$R_{1a}$ and $R_{2a}$ together form a covalent bond;

$R_3$ and $R_4$ are each independently unsubstituted alkyl;

$R_{3a}$ and $R_{4a}$ are each independently hydrogen, or together form a covalent bond;

$R_5$ is unsubstituted alkyl;

$R_6$ and $R_{6a}$ together form =O;

$R_7$ is azaalkyl, or azaaralkyl;

$R_8$ and $R_{8a}$ together form =O;

$R_9$ is substituted alkyl;

$R_{10}$ is unsubstituted alkyl;

each of $R_1$-$R_{10}$, when substituted, is substituted with one or more substituents each independently selected from Q, where Q is halo, pseudohalo, haloalkyl, $COOR_b$ where $R_b$ is hydrogen or alkyl, $OR_c$ where $R_c$ is alkyl or aralkyl, $NR_fR_g$ where $R_f$ and $R_g$ are each independently hydrogen, alkyl or aralkyl, or $=NR_h$ where $R_h$ is aralkyl;

each Q is independently unsubstituted or is substituted with one or more substituents each independently selected from $Q_1$, where $Q_1$ is halo, pseudohalo, or haloalkyl.

Further provided are compounds where $R_1$ is methyl;

$R_{1a}$ and $R_{2a}$ together form a covalent bond;

$R_3$ is methyl; $R_4$ is ethyl;

$R_{3a}$ and $R_{4a}$ are each independently hydrogen, or together form a covalent bond;

$R_5$ is methyl;

$R_9$ is $CH_2CH_2COOH$ or $CH_2CH_2COOMe$;

$R_{10}$ is methyl.

Also provided are compounds where $R_2$ is $CH{=}CH_2$, $CH(OR_{20})CH_3$, C(O)Me, $C(=NR_{21})CH_3$ or $CH(NHR_{21})CH_3$;

where $R_{20}$ is methyl, butyl, heptyl, dodecyl or 3,5-bis(trifluoromethyl)-benzyl; and $R_{21}$ is 3,5-bis(trifluoromethyl)benzyl.

Also provided are compounds where $R_7$ is $=NR_{20}$, where $R_{20}$ is methyl, butyl, heptyl, dodecyl or 3,5-bis(tri-fluoromethyl)benzyl.

In another embodiment, $R_1$ is substituted or unsubstituted alkyl, substituted or unsubstituted alkenyl, substituted or unsubstituted alkynyl, or substituted or unsubstituted cycloalkyl; —$C(O)R_a$ or —$COOR_a$, where $R_a$ is hydrogen, substituted or unsubstituted alkyl, substituted or unsubstituted alkenyl.

In another embodiment, $R_2$ is substituted or unsubstituted alkyl, substituted or unsubstituted alkenyl, substituted or unsubstituted alkynyl, or substituted or unsubstituted cycloalkyl; —$C(O)R_a$ or —$COOR_a$, where $R_a$ is hydrogen, substituted or unsubstituted alkyl, or substituted or unsubstituted alkenyl.

In a further embodiment, $R_{1a}$ is hydrogen or substituted or unsubstituted alkyl.

In another embodiment, $R_{2a}$ is hydrogen or substituted or unsubstituted alkyl.

In a further embodiment, $R_{1a}$ and $R_{2a}$ together form a covalent bond.

In another embodiment, $R_3$ is hydrogen or substituted or unsubstituted alkyl;

In a further embodiment, $R_4$ is hydrogen or substituted or unsubstituted alkyl;

In another embodiment, $R_{3a}$ is hydrogen.

In another embodiment, $R_{4a}$ is hydrogen.

In a further embodiment, $R_{3a}$ and $R_{4a}$ together form a covalent bond.

In another embodiment, $R_5$ is substituted or unsubstituted alkyl.

In another embodiment, $R_6$ and $R_{6a}$ together form =O.

In a further embodiment, $R_7$ is azaalkyl or azaaralkyl.

In another embodiment, $R_8$ and $R_{8a}$ together form =O.

In another embodiment, $R_9$ is substituted alkyl.

In a further embodiment, $R_{10}$ is unsubstituted alkyl.

In another embodiment, each of $R_1$-$R_{10}$ is substituted with one to five substituents, each independently selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is unsubstituted.

In a further embodiment each of $R_1$-$R_{10}$ is substituted with one substituent selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is unsubstituted.

In another embodiment, each of $R_1$-$R_{10}$ is substituted with two substituents, each independently selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is unsubstituted.

In a further embodiment each of $R_1$-$R_{10}$ is substituted with three substituents, each independently selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is unsubstituted.

In another embodiment, each of $R_1$-$R_{10}$ is substituted with one to five substituents, each independently selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is independently substituted with one to five substituents selected from $Q_1$, where $Q_1$ is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl or aryl, or is an amino acid residue.

In a further embodiment each of $R_1$-$R_{10}$ is substituted with one substituent selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is independently substituted with one substituent selected from $Q_1$, where $Q_1$ is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl or aryl, or is an amino acid residue.

In another embodiment, each of $R_1$-$R_{10}$ is substituted with two substituents, each independently selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is substituted with two substituents, each independently selected from $Q_1$, where $Q_1$ is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl or aryl, or is an amino acid residue.

In a further embodiment each of $R_1$-$R_{10}$ is substituted with three substituents, each independently selected from Q, where Q is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl, arallkyl, or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl, aralkyl or aryl, $=NR_h$ where $R_h$ is alkyl, alkenyl, alkynyl, cycloalkyl, aralkyl or aryl, or is an amino acid residue, where each Q is substituted with three substituents, each independently selected from $Q_1$, where $Q_1$ is alkyl, haloalkyl, halo, pseudohalo, —$COOR_b$ where $R_b$ is hydrogen, alkyl, alkenyl, alkynyl, cycloalkyl or aryl, aryl, heteroaryl, cycloalkyl, heterocyclyl, $OR_c$ where $R_c$ is hydrogen, alkyl, alkenyl, alkynyl, cycloalkyl or aryl, $CONR_dR_e$ where $R_d$ and $R_e$ are each independently hydrogen, alkyl, alkenyl, alkynyl, cycloalkyl or aryl, $NR_fR_g$ where $R_f$ and $R_g$ are each independently hydrogen, alkyl, alkenyl, alkynyl, cycloalkyl or aryl, or is an amino acid residue.

Also provided is a compound of the formula:

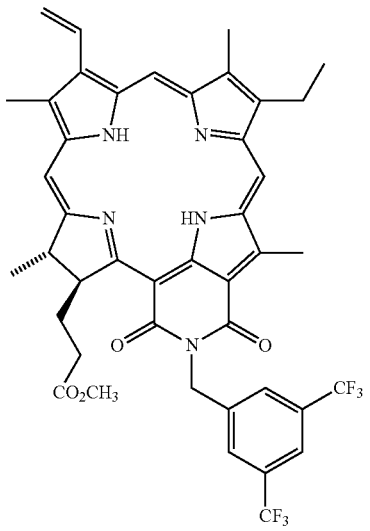

or a pharmaceutically acceptable derivative thereof.

Also provided is a compound of the formula:

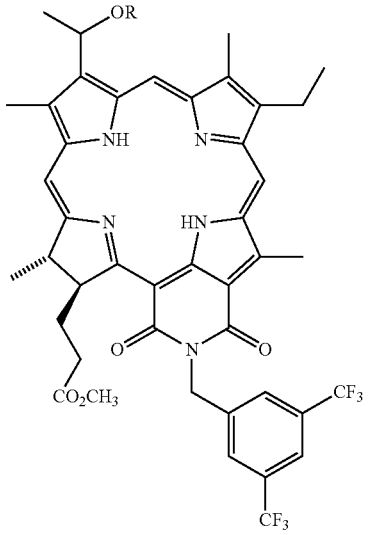

or a pharmaceutically acceptable derivative thereof, where R is methyl, butyl, heptyl or dodecyl.

Also provided is a compound of the formula:

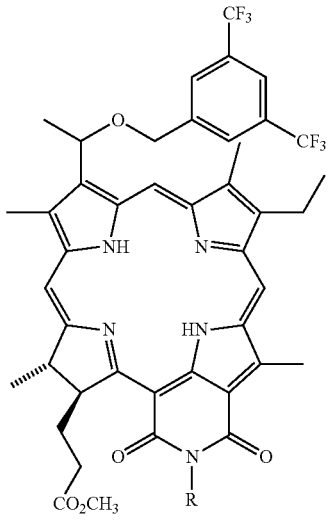

or a pharmaceutically acceptable derivative thereof, where R is methyl, butyl, heptyl or dodecyl.

Also provided is a compound of the formula:

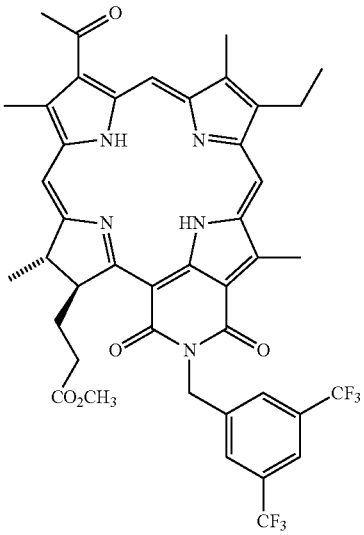

or a pharmaceutically acceptable derivative thereof.

Also provided is a compound of the formula:

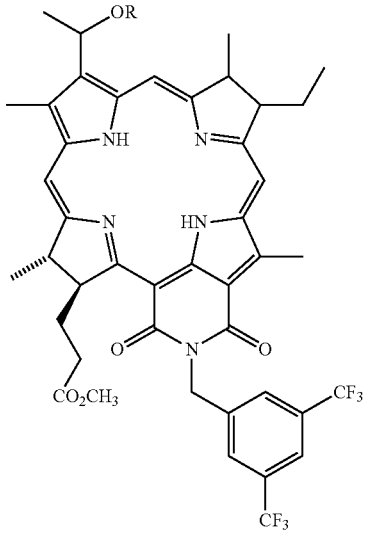

or a pharmaceutically acceptable derivative thereof, where R is methyl, butyl, heptyl or dodecyl.

Also provided is a compound of the formula:

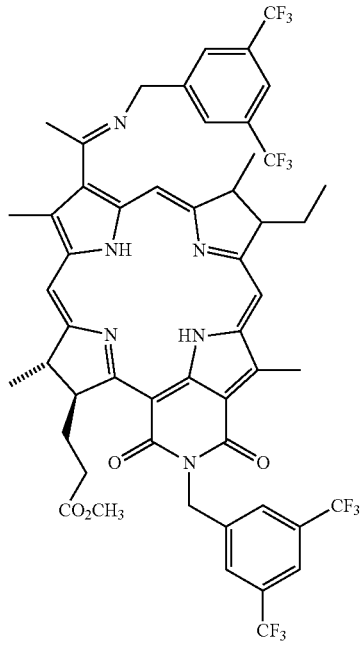

or a pharmaceutically acceptable derivative thereof.

Also provided is a compound of the formula:

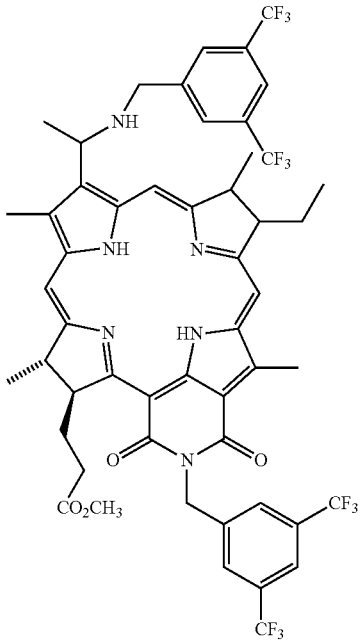

or a pharmaceutically acceptable derivative thereof.

Also provided is a compound of the formula

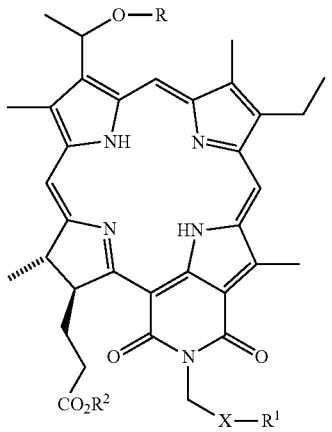

or a pharmaceutically acceptable derivative thereof, where X is an aryl or heteroaryl group; R and $R^1$ are each independently alkyl, aryl, or heteroaryl groups having 1-20 carbon atoms, wherein at least one of R and $R^1$ is substituted with at least one fluorine atom; and $R^2$ is an alkyl group, optionally substituted with one or more fluorine atoms.

Also provided is a compound of the formula

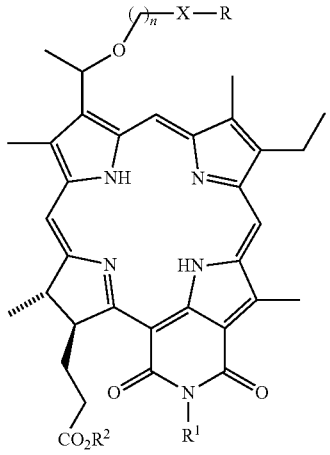

or a pharmaceutically acceptable derivative thereof, where X is an aryl or heteroaryl group; n is an integer from 0 to 6; R and $R^1$ are each independently alkyl, aryl, or heteroaryl groups having 1-20 carbon atoms, where at least one of R and $R^1$ is substituted with at least one fluorine atom; and $R^2$ is an alkyl group, optionally substituted with one or more fluorine atoms.

Also provided is a compound of the formula

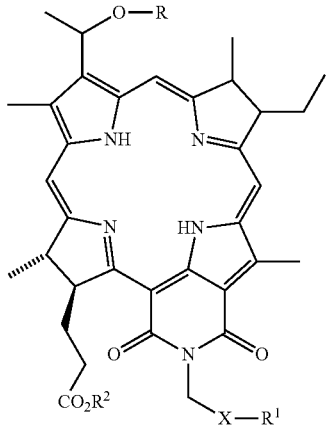

or a pharmaceutically acceptable derivative thereof, where X is an aryl or heteroaryl group; R and $R^1$ are each independently alkyl, aryl, or heteroaryl groups having 1-20 carbon atoms, where at least one of R and $R^1$ is substituted with at least one fluorine atom; and $R^2$ is an alkyl group, optionally substituted with one or more fluorine atoms.

Also provided is a compound of the formula

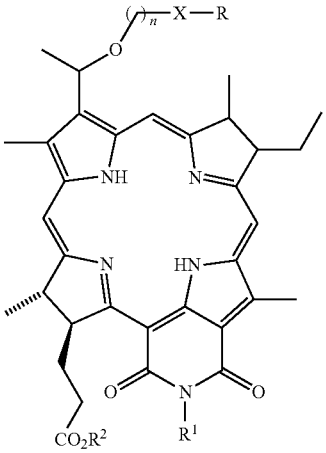

or a pharmaceutically acceptable derivative thereof, where X is an aryl or heteroaryl group; n is an integer from 0 to 6; R and $R^1$ are each independently alkyl, aryl, or heteroaryl groups having 1-20 carbon atoms, wherein at least one of R and $R^1$ is substituted with at least one fluorine atom; and $R^2$ is an alkyl group, optionally substituted with one or more fluorine atoms.

Also provided is a compound of the formula

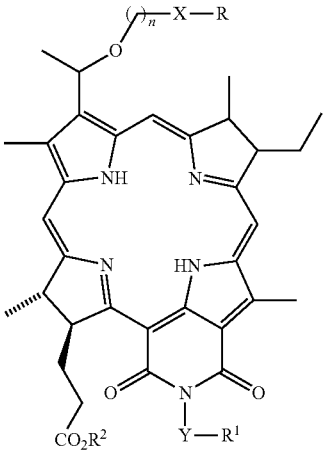

or a pharmaceutically acceptable derivative thereof, where X and Y are each independently an aryl or heteroaryl group; n is an integer from 0 to 6; R and $R^1$ are each independently alkyl, aryl, or heteroaryl groups having 1-20 carbon atoms, wherein at least one of R and $R^1$ is substituted with at least one fluorine atom; and $R^2$ is an alkyl group, optionally substituted with one or more fluorine atoms.

C. Preparation of the Compounds

The compounds provided herein may be prepared according to the methods provided below and exemplified herein (see, e.g., EXAMPLE 3). The starting materials for synthesis of the compounds are readily available from commercial sources (e.g., Aldrich Chemical Company, Milwaukee, Wis., USA). Other compounds within the scope of the instant disclosure may be prepared by routine modification of the procedures provided herein using appropriate starting materials, the selection of which will be evident to those of skill in the art.

In order to determine the effect of the presence and position of aromatic substituents (instead of N-alkyl and or O-alkyl) on biological activity, purpurinimides 8 and 11 containing N-3,5-dimethylbenzyl- or 3-[1'-(3,5-dimethyl benzyloxy) ethyl] substituents with similar log P value (11.83) were synthesized, as shown in Scheme 1. This approach was then extended for the preparation of the related N- and O-trifluoromethyl substituted analogs 9 and 12, respectively. In brief, methylpheophorbide-a 1 was extracted from Spirulina pacifica and converted into purpurin-18 methyl ester 2 by following well established methodology (Smith, K. M.; Goff, D. A. and Simpson, D., J. Am. Chem. Soc. 107: 4941 (1985); Smith, K. M., Porphyrins and Metalloporphyrins (Smith, K. M., Ed.), Elsevier Sci. Pub, Amsterdam, 1975). Reaction of 2 with 3,5-dimethyl-benzyl amine at room temperature produced the intermediate amide as a mixture of two isomers, which under base-catalyzed intramolecular cyclization produced purpurinimide 6 in 70% overall yield. Further reaction of 6 with HBr/HOAc and then with 1-butanol gave the corresponding n-butyl ether derivative 8 in 70% yield. By following similar reaction conditions, other related non-fluorinated and fluorinated photosensitizers 9, 11 and 12 were also prepared, as shown in Scheme 1.

Scheme 1

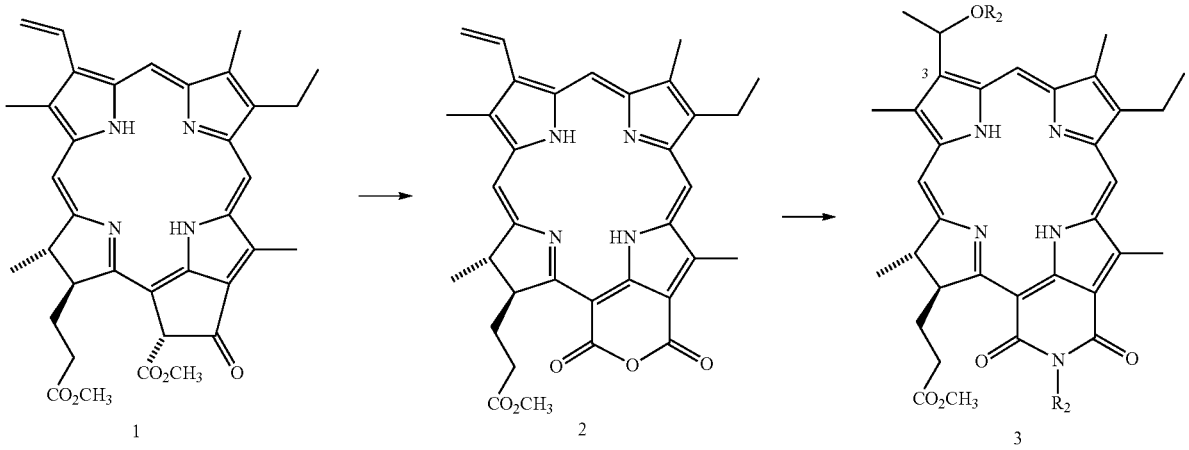

-continued

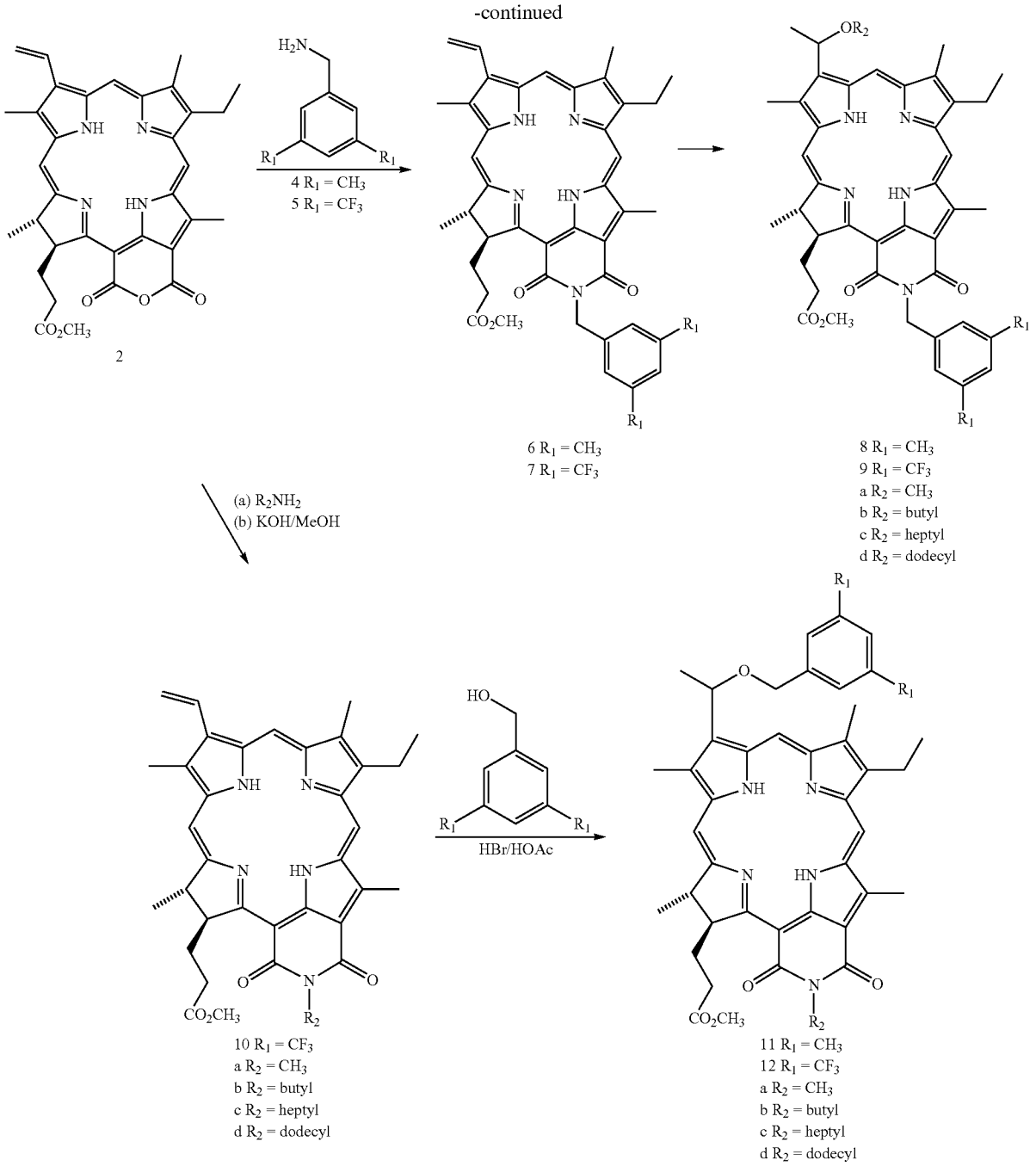

The structures of these compounds were confirmed by NMR and mass spectrometry analyses (Zheng, G.; Potter, W. R.; Camacho, S. H., Missert, J. R., Wang, G., Bellnier, D. A., Henderson, B. W., Rodgers, M. A. J., Dougherty, T. J., and Pandey, R. K., J. Med. Chem. 44: 1540-1559 (2001). The presence of trifluoromethyl substituents in purpurinimides 9 and 12 was confirmed by $^{19}$F NMR spectroscopy (the resonances for the symmetrical trifluoromethyl groups in 9 and 12 were observed at δ 13.145 and 12.598 ppm, respectively).

The electronic absorption spectra of PHOTOFRIN® (a porphyrin analog), HPPH (a chlorin bearing a five-membered isocyclic ring) and the purpurinimide 9 (a chlorin with an expanded, six-membered fused imide ring) were measured in dichloromethane at the same molar concentrations. As can be seen from FIG. 1, both HPPH ($\lambda_{max}$=660 nm) and purpurinimide ($\lambda_{max}$=700 nm) produce stronger long wavelength absorption (ϵ=45,000) than the porphyrin PHOTOFRIN® with considerable red-shifts of 30 nm and 70 nm, respectively.

Compounds Related to Bacteriochlorins

As discussed above, the studies with a series of purpurinimides indicate that among all the photosensitizers evaluated so far, the purpurinimide 9 containing N-[(3,5-bis(trifluoromethyl)benzyl] group produced the best in vivo efficacy. Therefore, to investigate the effect of such substituents in compounds with longer wavelength absorption near 800 nm, bacteriopurpurin-18 methyl ester 13 (a bacteriochlorin) obtained by following the methodology developed in our laboratory (see Scheme 2 below and U.S. Pat. No. 5,591,847) was treated with 3,5-bis(trifluoromethyl)benzyl amine.

The formation of the reaction products was found to be temperature dependent. For example, when the reaction was performed at elevated temperature, the N-fluorinated derivative 15 and the corresponding Schiff base 17 (obtained from the reaction of the 3-acetyl group with an amine) was isolated in almost equal ratio. However, at low temperature, 3-acetyl-N-substituted-bacteriopurpurinimide 15 was isolated as a major product. Bacteriochlorin 15 on reaction with sodium borohydride and then with HBr gas followed by a reaction with n-butyl alcohol produced the corresponding butyl ether derivative 16. The Schiff base 17 was found to be unstable in vivo and rapidly converted into the related acetyl analog 15 in quantitative yield (determined by in vivo reflectance spectroscopy). However, reduction of 17 with sodium borohydride at room temperature produced stable amine 18. See Scheme 2.

Scheme-2

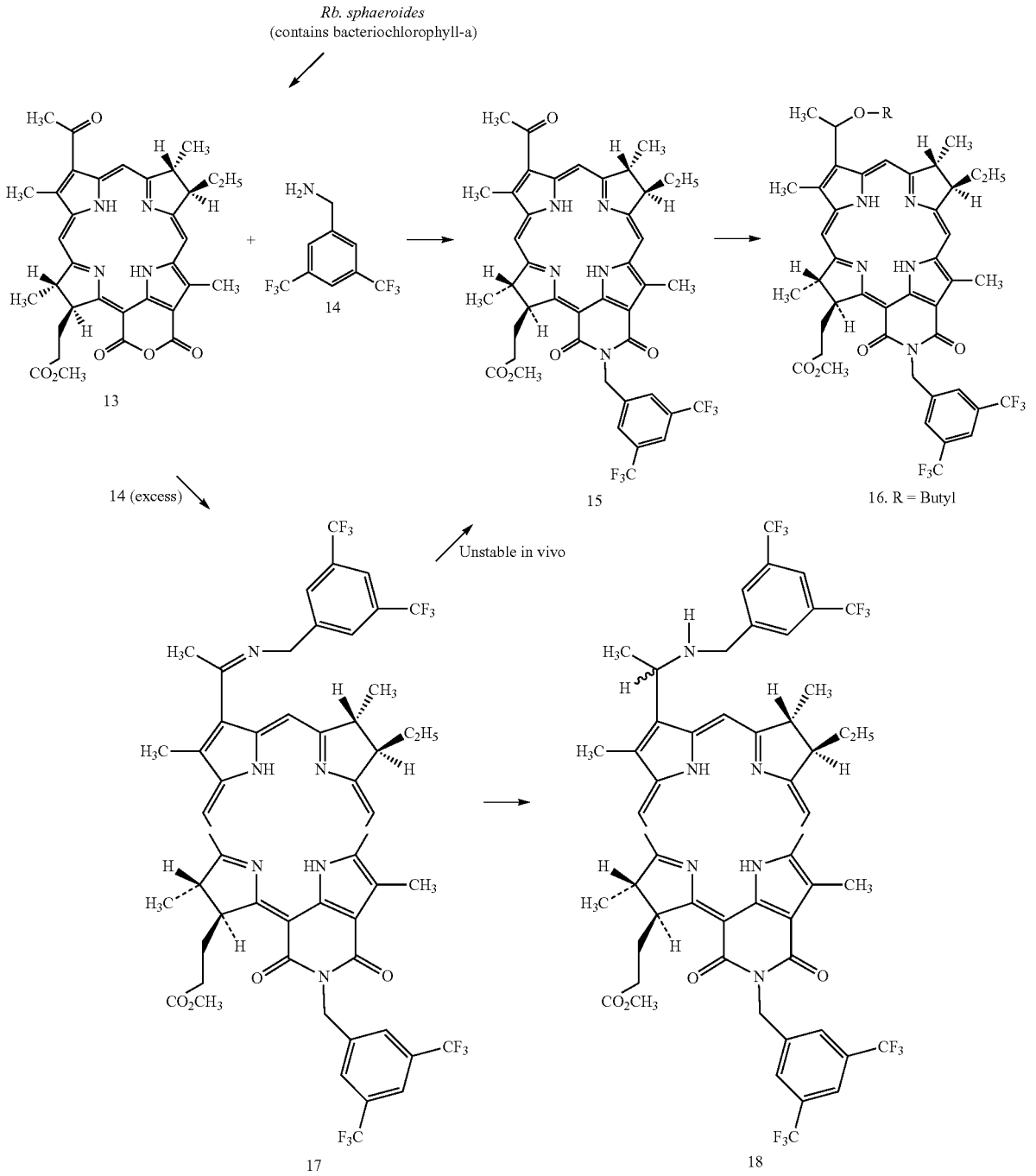

D. Pharmaceutical Compositions

1. Formulation of Pharmaceutical Compositions

The pharmaceutical compositions provided herein contain therapeutically effective amounts of one or more of the compounds provided herein that are useful in the prevention, treatment, or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in U.S. Pat. No. 5,952,366 to Pandey et al. (1999) (see, e.g., EXAMPLE 7) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of active ingredient of from about 0.1 μg/ml to about 50-100 μg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only is and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

2. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carver, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

3. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, xanthan gum, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

4. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

5. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

6. Compositions for other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983; 6,261,595; 6,256,533; 6,167,301; 6,024,975; 6,010,715; 5,985,317; 5,983,134; 5,948,433 and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

7. Targeted Formulations

The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

a. Liposomes

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

b. Ligands

In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following:

| Anti-bacterial Mabs |
|---|
| *Streptococcus agalactiae* |
| *Legionella pneumophilia* |
| *Streptococcus pyogenes* |
| *Esherichia coli* |
| *Neisseria gonorrhosae* |
| *Neisseria meningitidis* |
| Pneumococcus |
| *Hemophilis influenzae* B |
| *Treponema pallidum* |
| Lyme disease spirochetes |
| *Pseudomonas aeruginosa* |
| *Mycobacterium leprae* |
| *Brucella abortus* |
| *Mycobacterium tuberculosis* |
| Tetanus toxin |
| Anti-protozoan Mabs |
| *Plasmodium falciparum* |
| *Plasmodium vivax* |
| *Toxoplasma gondii* |
| *Trypanosoma rangeli* |
| *Trypanosoma cruzi* |
| *Trypanosoma rhodesiensei* |
| *Trypanosoma brucei* |
| *Schistosoma mansoni* |
| *Schistosoma japanicum* |
| *Mesocestoides corti* |
| *Elmeria tenella* |
| *Onchocerca volvulus* |
| *Leishmania tropica* |
| *Trichinella spiralis* |
| *theileria parva* |
| *Taenia hydatigena* |
| *Taenia avis* |
| *Taenia saginata* |
| Anti-viral MAbs |
| HIV-1, -2, -3 |
| Hepatitis A, B, C, D |
| Rabies virus |
| Influenza virus |
| Cytomegalovirus |
| Herpes simplex I and II |
| Human serum parvo-like virus |
| Respiratory syncytial virus |
| Varicella-Zoster virus |
| Hepatitis B virus |
| Measles virus |
| Adenovirus |
| Human T-cell leukemia viruses |
| Epstein-Barr virus |
| Mumps virus |
| Sindbis virus |
| Mouse mammary tumor virus* |
| Feline leukemia virus* |
| Lymphocytic choriomeningitis virus |
| Wart virus |
| Blue tongue virus |
| Sendai virus |
| Reo virus |
| Polio virus |
| Dengue virus |
| Rubella virus |
| Murine leukemia virus* |
| Antimycoplasmal MAbs |
| *Acholeplasma laidlawii* |
| *Mycoplasma anhtitidis* |
| *M. hyorhinis* |
| *M. orale* |
| *M. arginini* |
| *M. pneumonia* |

*animal virus

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to T. gondii, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include $F(ab')_2$, $F(ab)_2$, Fab', Fab, Fv and the like including hybrid fragments. Preferred fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

c. Conjugation to Ligands

Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-S-acetyl-thioacetate (SATA), N-succinimidyl-3-(2-pyridyldithio)propionate (SPDP), ortho-phenylene-dimaleimide (o-PDM), and sulfo-succinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin e6 in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizes; which contain carboxyl groups can be joined to lysine ϵ-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B. et al., Ciba Found Symp. 186: 5-20 (1994).

8. Articles of Manufacture

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

E. Methods of Use of the Compounds and Compositions

1. Methods of PDT, Diagnostic and Therapeutic Applications

Briefly, the photosensitizing compound is generally administered to the subject before the target tissue, target composition or subject is subjected to illumination. The photosensitizing compound is administered as described elsewhere herein.

The dose of photosensitizing compound can be determined clinically. Depending on the photosensitizing compound used, an equivalent optimal therapeutic level will have to be established. A certain length of time is allowed to pass for the circulating or locally delivered photosensitizer to be taken up by the target tissue. The unbound photosensitizer is cleared from the circulation during this waiting period, or additional time can optionally be provided for clearing of the unbound compound from non-target tissue. The waiting period will be determined clinically and may vary form compound to compound.

At the conclusion of this waiting period, a laser light source or a non-laser light source is used to activate the bound drug. The area of illumination is determined by the location and dimension of the pathologic region to be detected, diagnosed or treated. The duration of illumination period will depend on whether detection or treatment is being performed, and can be determined empirically. A total or cumulative period of time anywhere from between about 4 minutes and 72 hours can be used. In one embodiment, the illumination period is between about 60 minutes and 148 hours. In another embodiment, the illumination period is between about 2 hours and 24 hours.

Preferably, the total fluence or energy of the light used for irradiating, as measured in Joules, is between about 10 Joules and about 25,000 Joules; more preferably, between about 100 Joules and about 20,000 Joules; and most preferably, between about 500 Joules and about 10,000 Joules. Light of a wavelength and fluence sufficient to produce the desired effect is selected, whether for detection by fluorescence or for therapeutic treatment to destroy or impair a target tissue or target composition. Light having a wavelength corresponding at least in part with the characteristic light absorption wavelength of the photosensitizing agent is preferably used for irradiating the target issue.

The intensity or power of the light used is measured in watts, with each Joule equal to one watt-sec. Therefore, the intensity of the light used for irradiating in the present invention may be substantially less than 500 $mW/cm^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

While not wishing to be limited by a theory, the inventor proposes that the disclosed photosensitizing compounds can be substantially and selectively photoactivated in target tissue or target compositions within a therapeutically reasonable period of time and without excess toxicity or collateral damage to non-target tissues.

In one embodiment of using compounds disclosed herein for photodynamic therapy, the compounds are injected into the mammal, e.g. human, to be diagnosed or treated. The level of injection is usually between about 0.1 and about 0.5 μmol/kg of body weight. In the case of treatment, the area to be treated is exposed to light at the desired wavelength and energy, e.g. from about 10 to 200 $J/cm^2$. In the case of detection, fluorescence is determined upon exposure to light at a wavelength sufficient to cause the compound to fluoresce at a wavelength different than that used to illuminate the compound. The energy used in detection is sufficient to cause fluorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A_person may be instructed in how to use the kit using any of the instructions above or by receiving instructions in a classroom or in the course of treating a patient using any of the methods disclosed herein, for example.

2. Imaging Enhancing Agents

In addition to PDT, the compositions provided herein can be used as imaging enhancing agents in diagnostic imaging techniques, or for the labeling of target tissues or target compositions for diagnostic radiology. In the modern medical field, there area variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolusion yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., Am. J. Radiol. 141: 1209 (1983). When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^{1}H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds can be used as image enhancing agents and will provide labeling of specific target tissues or target compositions for diagnostic radiology, including MRI.

3. Detecting Target Tissue or Target Compositions

In addition to PDT, the compositions provided herein can be used to detect target cells, target tissue, or target compositions in a subject. When the compounds provided herein are to be used for detection of target tissue or target composition, the compounds are introduced into the subject and sufficient time us allowed for the compounds to accumulate in the target tissue or to become associated with the target composition. The area of treatment is then irradiated, generally using light of an energy sufficient to cause fluorescence of the compound, and the energy used is usually significantly lower than is required for photodynamic therapy treatment. Fluorescence is determined upon exposure to light at the desired wavelength, and the amount of fluorescence can be correlated to the presence of the compound, qualitatively or quantitatively, by methods known in the art.

4. Diagnosing an Infecting Agent

The compositions provided herein can be used to diagnose the presence of an infecting agent, or the identity of an infecting agent in a subject. The compounds provided herein can be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound can be visualized, such as by exposing to light of an energy sufficient to cause fluorescence of the compound, or by imaging using diagnostic radiology, including MRI. By way of example, any one of the compounds provided herein can be conjugated to an antibody that is targeted against a suitable Helicobacter pylori antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject can be examined to determine whether any Helicobacter pylori is present. This can be done by MRI to detect accumulated compound because of the presence of $^{19}F$ substituents, for example, or by irradiating the suspect target area with light of an energy sufficient to cause fluorescence of the compound, such as by using fiberoptics, and detecting any fluorescence of the targeted compound.

F. Assay Methods Used for Testing the Compounds

The compounds provided herein have been evaluated in in vivo studies in a mouse tumor model system (RIF tumor). The compounds were tested at variable concentrations by incubating with RIF cells, and after a 3 hour incubation in the dark at 37° C., the cells were washed with PBS, then irradiated with a 1000 W Quartz Halogen Lamp with IR and bandpass dichroic filters to allow light between 400 nm-700 nm, at a dose rate of 16 mW/cm$^2$ at 700 nm. The percent cell kill rate was then determined for each condition.

The following examples are included for illustrative purposes only and are not intended to limit the scope of the subject matter claimed herein.

EXAMPLES

Melting points are uncorrected and were measured on a Fisher Johns melting point apparatus. Electronic absorption spectra were measured on a Genesis 5 spectrophotometer. Analytical thin layer chromatography was used to monitor the reactions and to check the purity of the desired compounds on cut strips of Merck or Whatman silica gel 60F264 precoated (0.25 mm thickness) plastic backed sheets. For column chromatography Silica gel (70-230 mesh) was used for normal gravity column.

NMR spectra were recorded in $CDCl_3$ or TFA solutions at 400 or 600 MHz Bruker instruments. Chemical shifts are expressed in ppm with residual $CHCl_3$ in $CDCl_3$ as internal standard (for $^1H$, 7.26 ppm). UV-vis spectra were recorded on a Varian (Cary-50 Bio) spectrophotometer. Separations on column chromatography were performed on silica gel 60 (70-230 mesh) or neutral alumina (Brockmann grade III, 150 mesh). Preparative TLC was performed on silica 20×20 cm TLC plates (Aldrich).

Before in vitro and in vivo testing of the compounds, the purity of the material was confirmed by HPLC and it was performed using a Spectra-Physics system connected to a SP8 700 solvent delivery system, Kratos 757 absorption detector with a fixed wavelength ant 405 or 786 nm. Two solvent systems were used in the HPLC analysis: solvent A was prepared by dissolving anhydrous dibasic sodium phosphate (1.0 g) in 400 ml water. To this was added HPLC grade methanol (60 ml). The pH of the solution was adjusted to 7.5 with phosphoric acid; and (ii) solvent B was prepared by dissolving anhydrous dibasic sodium phosphate (0.3 g) in 100 ml water, and_to this was added methanol (900 ml) and the pH was adjusted to 7.5 with phosphoric acid. Solvents A and B were used as gradient mode (0-10 min A, 10-40 min A-B, 40-50 min B, 50-60 min back to A). In some cases solvent B was used as isocratic mode (column reverse phase C-8, flow rate 1.5 ml/min).

Example 1

Preparation of 3-acetyl-bacteriopurpurin-18-methyl ester

Bacteriopurpurin-18 methyl-ester 13 was obtained from bacteriochlorophyll-a, which can be isolated from R. spheroides or R. capsulata (see U.S. Pat. No. 5,591,847). R. spheroides (350 gram) was dissolved in ether (200 mL) and pyridine (10 mL). Sodium hydroxide (12 g) dissolved in methanol (100 mL) was added and a stream of air was bubbled through the solution with constant stirring for 2 hours. The ether layer was removed, and the pH of the aqueous phase was adjusted by adding $H_2SO_4$ to 2.5. The solvent was removed under vacuum. The residue so obtained was redissolved in THF and evaporated. This process was repeated several times until the peak at 765 nm disappeared and a new peak appeared at 804 nm. After removing the solvent, the residue was found to be a mixture of two compounds and separated by column chromatography. The faster moving band was identified as the title product, whereas the slowing moving band was characterized as the related carboxylic acid analog, which on treating with 5% sulfuric acid/methanol or diazomethane produced the corresponding methyl ester. Yield: 250 mg. M. P. 272° C. (Y. Chen, Ph. D. thesis, entitled "Long Wavelength Absorbing Photosensitizers Related to Bacteriochlorins," RCPI/SUNY, Buffalo, Sep. 1, 2002).

Example 2

General Method for the Preparation of N-substituted Purpurinimides

Purpurin-18 methyl ester was prepared by following the literature procedure (Zheng, G.; Potter, W. R.; Camacho, S. H., Missert, J. R., Wang, G., Bellnier, D. A., Henderson, B. W., Rodgers, M. A. J., Dougherty, T. J., and Pandey, R. K., J. Med. Chem. 44: 1540-1559 (2001). In a typical experiment, purpurin-18 methyl ester (500 mg) was dissolved in toluene (30 ml) at reflux. A large excess of 3,5-bis(trimethyl)- or 3,5-bis(trifluoromethyl)benzylamine was added and the reaction was continued until it was complete. The reaction was monitored spectrophotometrically, and the disappearance of the 699 nm band and the appearance of a new peak at 705 nm in the UV-Vis spectrum indicated the completion of the reaction. The reaction solvent and the excess of the amine were then evaporated under high vacuum to give the residue, which was purified by chromatography on a silica column eluting with 2% acetone in dichloromethane. Evaporation of the solvents from the appropriate fractions afforded the corresponding N-substituted purpurinimide in 70-75% yield. The purpurin-18-N-butylimide was prepared by following the method reported previously (Zheng, G.; Potter, W. R.; Camacho, S. H.; Missert, J. R.; Wang, G.; Bellnier, D. A.; Henderson, B. W.; Rodgers, M. A. J.; Dougherty, T. J.; and Pandey, R. K., J. Med. Chem. 44: 1540-1559 (2001)).

Example 3

General Method for the Preparation of O-alkyl or O-benzyl (Fluorinated or Non-fluorinated) N-alkyl or N-aryl-purpurinimides For the preparation of the desired ether analogs, purpurin-18-N-substitute imide (100 mg) was reacted with 30% HBr/AcOH (1.5 mL) in a closed flask using a rubber septum and the reaction mixture was stirred at room temperature for 2 hours. After evaporating the acid under high vacuum and low temperature (around 30° C.), the residue was allowed to react with an excess of the desired alcohol. Dry dichloromethane (10 mL) and anhydrous potassium carbonate (50 mg) were then added and the reaction mixture was stirred under the nitrogen atmosphere for 45 min. It was then diluted with dichloromethane (200 mL) and treated with etheral diazomethane for 5 min. Before evaporating the solvent, the excess diazomethane was removed by passing a stream of nitrogen through the solution. The residue so obtained was purified by chromatography on alumina (Gr III) and eluted with dichloromethane. The appropriate fractions were combined. Evaporation of the solvent gave the desired compounds in 70-75% yield.

The following compounds were prepared according to the methods of EXAMPLES 2 and 3 by routine modification using appropriate starting materials and reagents.

Compound 9

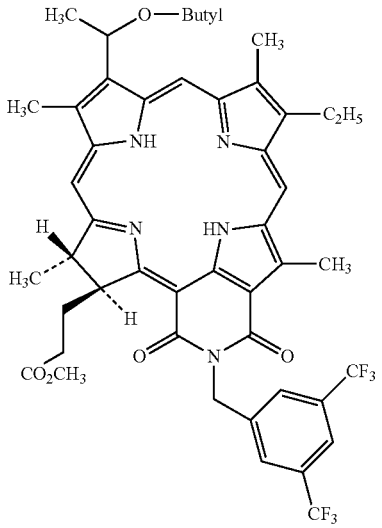

Melting point: sticky solid. UV-Vis (THF): 700.0 ($4.50\times10^4$), 644.1 ($6.71\times10^3$), 544.0 ($1.90\times10^4$), 508.0 ($6.02\times10^3$), 480.0 ($3.54\times10^3$), 415.0 ($1.11\times10^5$), 364.0 ($3.96\times10^4$). $^1$H NMR (400 MHz, $CDCl_3$) δ, ppm: 9.75 and 9.63 (each s, 1H, for 10H and 5H); 8.52 (s, 1H, for 20H); 8.25 (s, 2H, 2×ArH); 7.81 (s, 1H, ArH); 5.77 (s, 3H, N—$CH_2$ & $3^1CH$); 5.34 (d, J=7.6 Hz, 1H, 17H); 4.35 (q, J=7.2 Hz, 1H, 18H); 3.84 (s, 3H, $12CH_3$); 3.69 (d, J=6.8 Hz, 2H, $8^1CH_2$); 3.55 (s, 3H, $OCH_3$); 3.31 (s, 3H, $7CH_3$); 3.19 (s, 3H, $2CH_3$); 2.68 (t, J=10 Hz, 1H, $1\times17^1CH_2CH_2CO_2CH_3$); 2.37 (q, J=10 Hz, 2H, $17^2CH_2CH_2CO_2CH_3$); 2.06 (d, 3H, $18CH_3$); 1.96 (q, J=9.3 Hz, 1H, $1\times17^1CH_2CH_2CO_2CH_3$); 1.76 (d, J=6.8 Hz, 2H, $OCH_2$); 1.69 (t, J=7.4 Hz, 3H, $8^2CH_3$); 1.65 (m, 4H, O—$CH_2CH_2CH_2CH_3$), 0.89 (t, 3H, —$O(CH_2)_3CH_3$. 0.15 and 0.90 (each s, 1H 2NH). $^{19}$F NMR (400 MHz, $CDCl_3$) δ, ppm: 13.054 (referenced to TFA). Mass calculated for $C_{47}H_{49}N_5O_5F_6$: 877.36. Found: 878.3 (M+1).

Compound 12

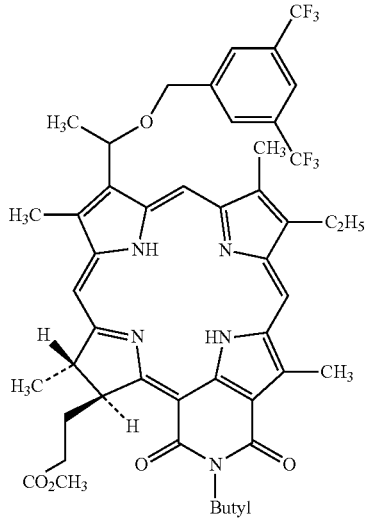

Melting point: sticky solid. UV-Vis (THF): 700.0 ($4.67\times10^4$), 642.0 ($5.97\times10^3$), 542.1 ($1.72\times10^4$), 507.0 ($6.29\times10^3$), 478.0 ($3.40\times10^3$), 415.0 ($1.25\times10^5$), 364.0 ($4.14\times10^4$). $^1$H NMR (400 MHz, $CDCl_3$) δ, ppm: 9.73 and 9.72 (each s, 1H, for 10H and 5H); 8.60 (s, 1H, for 20H); 7.85 (s, 2H, 2×ArH); 7.81 (s, 1H, ArH); 5.96 (q, J=6.8 Hz, 1H, $3^1CH$); 5.43 (d, J=8.0 Hz, 1H, 17H); 4.79 (s, 2H, O—$CH_2$); 4.48 (t, J=7.8 Hz, 2H, N—$CH_2$); 4.38 (q, J=7.2 Hz, 1H, 18H); 3.86 (s, 3H, $12CH_3$); 3.69 (q, J=7.6 Hz, 2H, $8^1CH_2$); 3.57 (s, 3H, $OCH_3$); 3.10 (s, 3H, $7CH_3$); 2.68 (s, 1H, $1\times17^1CH_2CH_2CO_2CH_3$); 2.44 (s, 1H, $1\times17^1CH_2CH_2CO_2CH_3$); 2.32 (s, $1\times17^2CH_2CH_2CO_2CH_3$); 2.21 (d, J=6.4 Hz, 3H, $3^2CH_3$); 1.99 (m, J=5.4 Hz, 2H, N—$CH_2CH_2CH_2CH_3$ & $17^2$H); 1.78 (d, J=6.8 Hz, 3H, $18CH_3$); 1.66 (m, J=7.9 Hz, 2H, N—$CH_2CH_2CH_2CH_3$ & 3H, $8^2CH_3$); 1.11 (t, J=7.4 Hz, 3H, N—$CH_2CH_2CH_2CH_3$); −0.172 an 0.17(each s, 1H, 2NH). $^{19}$F NMR (400 MHz, $CDCl_3$) δ, ppm: 12.598 (referenced to TFA). Mass calculated for $C_{47}H_{49}N_5O_5F_6$: 877.36. Found: 879 (M+2).

Compound 8

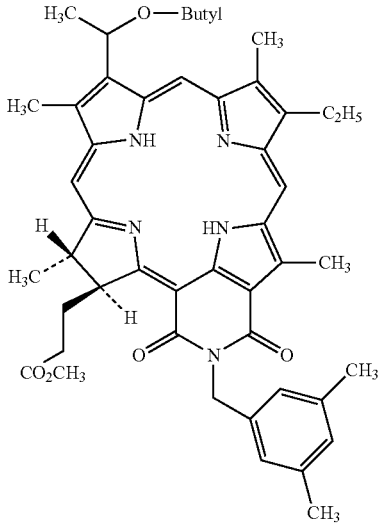

Melting point: sticky solid. UV-Vis (THF): 697.9 ($4.96\times10^4$), 640.9 ($9.15\times10^3$), 542.1 ($2.11\times10^4$), 506.0 ($1.01\times10^4$), 415.0 ($1.33\times10^5$), 363.0 ($4.59\times10^4$). $^1$H NMR (400 MHz, $CDCl_3$) δ, ppm: 9.75 and 9.64 (each s, 1H, for 10H and 5H); 8.53 (s, 1H, for 20H); 7.33 (s, 2H, 2×ArH); 6.89 (s, 1H, ArH); 5.78 (q, J=6.8 Hz, 1H, $3^1CH$); 5.62 (q, J=12.8, 2H, $OCH_2$); 5.42 (d, J=7.6 Hz, 1H, 17H); 4.33 (q, J=7.2 Hz, 1H, 18H); 3.83 (s, 3H, $12CH_3$); 3.53 (s, 3H, $17^2CH_2CH_2CO_2CH_3$); 3.30 (s, 3H, $7CH_3$); 3.18 (s, 3H, 2 $CH_3$); 2.31 (s, 6H, 2×ArH—$CH_3$); 2.05 (d, J=6.6 Hz, 2H, $8^2CH_3$); 1.75 (d, J=6.8 Hz, 3H, $18CH_3$); 1.52-1.67 (m, 4H, $CH_2CH_2CH_2CH_3$); 0.862 (t, 3H, O—$CH_2CH_2CH_2CH_3$); −0.046 (s, 1H, NH); −0.153 (s, 1H, NH). Mass calculated for $C_{47}H_{55}N_5O_5$: 769.42. Found: 792.4 (M+Na).

Compound 11

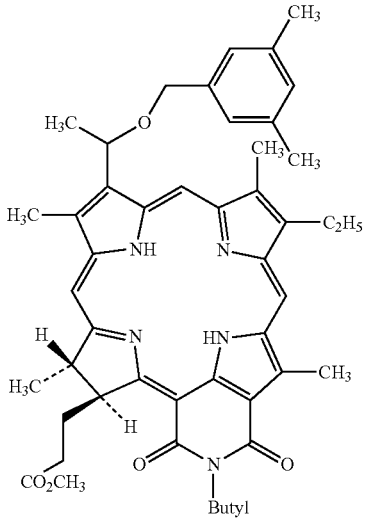

Melting point: sticky solid. UV-Vis (THF): 699.0 ($4.44\times10^4$), 642.0 ($6.32\times10^3$), 543.1 ($1.70\times10^4$), 508.1 ($6.54\times10^3$), 478.0 ($3.76\times10^3$), 415.0 ($1.23\times10^5$), 363.9 ($4.04\times10^4$). $^1$H NMR (400 MHz, $CDCl_3$) δ, ppm: 9.79 and 9.63 (each s, 1H, for 10H and 5H); 8.60 (s, 1H, for 20H); 7.79 (s, 1H, ArH); 6.96 (m, 2H, 2×ArH); 5.91 (q, 1H, $3^1$CH); 5.44 (m, 1H, 17H); 4.75 (2H, $OCH_2$); 4.49 (t, J=7.8 Hz, 2H, N—$CH_2$); 4.39 (m, 1H, 18H); 3.82 (s, 3H, $12CH_3$); 3.66 (q, J=7.6 Hz, 2H, $8^1CH_2$); 3.58 (s, 3H, $17^2CH_2CH_2CO_2CH_3$); 3.34 (m/s, 3H, $7CH_3$); 3.12 (s, 3H, $2CH_3$); 2.70 (m, 1H, $17^1CH_2CH_2CO_2CH_3$); 2.46 (m, 1H, $17^2CH_2CH_2CO_2CH_3$); 2.25 (s, 6H, 2×ArH—$CH_3$); 2.12 (d, J=6.4 Hz, 3H, $8^2CH_3$); 1.70 (d, 3H, $18CH_3$); 1.62-1.70 (m, 6H, N—$CH_2CH_2CH_2CH_3$); 1.12 (t, J=3.52 Hz, 3H, N—$CH_2CH_2CH_2CH_3$); −0.106 and −0.12 (each s, 1H, 2NH). Mass calculated for $C_{47}H_{55}N_5O_5$: 769.42. Found: 770 (M+1).

Compound 9b

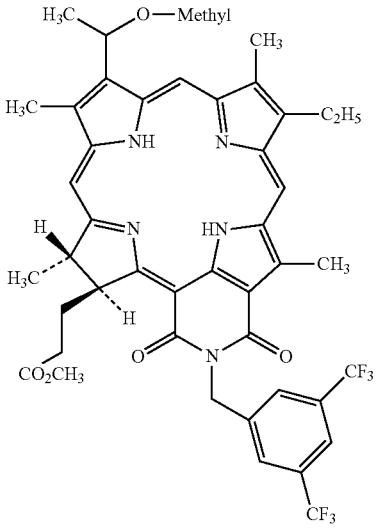

($R^1$ = methyl)

Melting point: sticky solid. UV-Vis (THF): 700.0 ($4.41\times10^4$), 646.1 ($6.05\times10^3$), 544.0 ($1.82\times10^4$), 506.9 ($5.42\times10^3$), 415.0 ($1.21\times10^5$), 364.0 ($3.93\times10^4$). $^1$H NMR (400 MHz, $CDCl_3$) δ, ppm: 9.65 and 9.46 (each s, 1H, for 10H and 5H); 8.56 (s, 1H, for 20H); 8.24 (s, 2H, 2×ArH); 7.82 (s, 1H, ArH); 5.74 (s, 3H, N—$CH_2$ & $3^1$CH); 5.36 (d, J=7.1 Hz, 1H, 17H); 4.37 (q, J=7.3 Hz, 1H, 18H); 3.68 (s, 3H, $12CH_3$); 3.69 (d, J=6.8 Hz, 2H, $8^1CH_2$); 3.55 (s, 6H, $OCH_3$ merged with a peripheral $CH_3$); 3.33 (s, 3H, $7CH_3$); 3.16 (s, 3H, $2CH_3$); 2.71 (t, J=9.9 Hz, 1H, $1\times17^1CH_2CH_2CO_2CH_3$); 2.39 (q, J=9.7 Hz, 2H, $17^2CH_2CH_2CO_2CH_3$); 2.07 (m, 3H, $8^2CH_3$); 1.97 (q, J=9.6 Hz, 1H, $1\times17^1CH_2CH_2CO_2CH_3$); 1.80 (d, J=7.6 Hz, 3H, $18CH_3$); 1.62 (t, J=7.8 Hz, 3H, $8^2CH_3$); 0.06 and 0.02 (each s, 1H, 2NH). $^{19}$F NMR (400 MHz, $CDCl_3$) δ, ppm: 13.284 (referenced to TFA). Mass calculated for $C_{44}H_{43}N_5O_5F_6$: 835.32. Found: 858.5 (M+Na).

Compound 9c

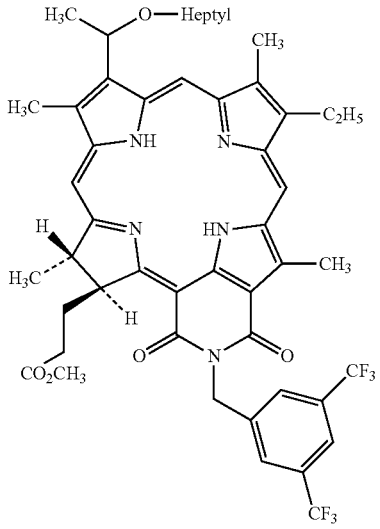

($R^1$ = heptyl)

Melting point: sticky solid. UV-Vis (THF): 700.0 ($4.56\times10^4$), 644.1 ($5.92\times10^3$), 544.9 ($1.83\times10^4$), 508.0 ($4.78\times10^3$), 416.0 ($1.22\times10^5$), 363.0 ($3.86\times10^4$). $^1$H NMR (400 MHz, $CDCl_3$) δ, ppm: 9.74 and 9.51 (each s, 1H, for 10H and 5H); 8.52 (s, 1H, for 20H); 8.23 (s, 2H, 2×ArH); 7.81 (s, 1H, ArH); 5.74 (s, 3H, N—$CH_2$ & $3^1$CH); 5.35 (d, J=8.4 Hz, 1H, 17H); 4.35 (q, J=7.3 Hz, 1H, 18H); 3.73 (s, 3H, $12CH_3$); 3.60 (d, J=4.0 Hz, 2H, $8^1CH_2$); 3.54 (s, 3H, $OCH_3$); 3.30 (s, 3H, $7CH_3$); 3.16 (s, 3H, $2CH_3$); 2.68 (t, J=9.7 Hz, 1H, $1\times17^1CH_2CH_2CO_2CH_3$); 2.42 (q, J=13 Hz, 2H, $17^2CH_2CH_2CO_2CH_3$); 2.11 (m, 3H, $8^2CH_3$); 2.01 (q, J=9.8 Hz, 1H, $1\times17^1CH_2CH_2CO_2CH_3$); 1.64 (d, 3H, $18CH_3$); 1.18-1.50 several peaks, $CH_2$'s of heptyl); 0.80 (t, 3H, $CH_3$ of the hexyl group); 0.20 and 0.15 (each s, 1H, NH). $^{19}$F NMR (400 MHz, $CDCl_3$) δ, ppm: 13.031 (referenced to TFA). Mass calculated for $C_{50}H_{55}N_5O_5F_6$: 919.41. Found: 942.4 (M+Na).

Compound 9d

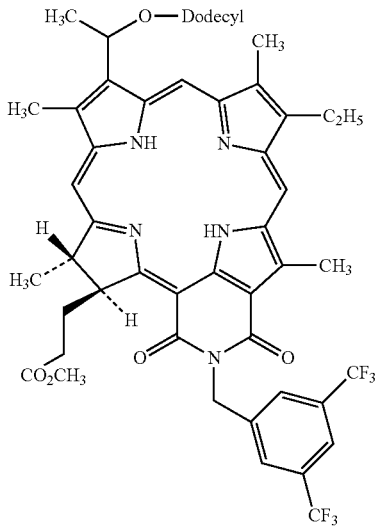

($R^1$ = dodecyl)

Melting point: sticky solid. UV-Vis (THF): 700.0 ($4.51\times10^4$), 645.1 ($6.79\times10^3$), 543.9 ($1.93\times10^4$), 507.0 ($6.21\times10^3$), 480 ($3.78\times10^3$), 415.0 ($1.23\times10^5$), 364.0 ($4.11\times10^4$). $^1$H NMR (400 MHz, $CDCl_3$) δ, ppm: 9.74 and 9.59 (each s, 1H, for 10H and 5H); 8.52 (s, 1H, for 20H); 8.23 (s, 2H, 2×ArH); 7.80 (s, 1H, ArH); 5.76 (s, 3H, N—$CH_2$ & $3^1$CH); 5.33 (d, J=8.5 Hz, 1H, 17H); 4.34 (q, J=7.2 Hz, 1H, 18H); 3.80 (s, 3H, $12CH_3$); 3.64 (d, J=6.4 Hz, 2H, $8^1CH_2$); 3.55 (s, 3H, $OCH_3$); 3.30 (s, 3H, $7CH_3$); 3.18 (s, 3H, $2CH_3$); 2.68 (t, J=9.9 Hz, 1H, $1\times17^1CH_2CH_2CO_2CH_3$); 2.37 (q, J=11 Hz, 2H, $17^2CH_2CH_2CO_2CH_3$); 2.05 (m, 3H, $3^1$CH3); 1.94 (q, J=9.7 Hz, 1H, $1\times17^1CH_2CH_2CO_2CH_3$); 1.76 (d, 2H, $OCH_2$); 1.67 (t, J=7.8 Hz, 3H, $8^2CH_3$); 1.55-1.10 (m, 20H, $CH_2$'s of dodecyl); 0.80 (t, 3H, $CH_3$ of dodecyl); 0.20 and 0.10 (each s, 1H, 2NH). $^{19}$F NMR (400 MHz, $CDCl_3$) δ, ppm: 13.171 (referenced to TFA). Mass calculated for $C_{55}H_{65}N_5O_5F_6$: 989.49. Found: 1012.6 (M+Na).

Compound 16

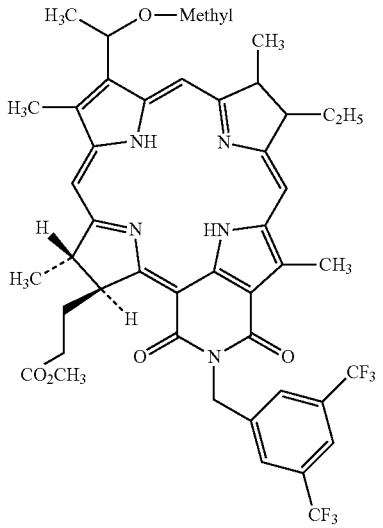

(R = methyl)

Melting point: sticky solid. UV-Vis ($CH_2Cl_2$): 784.0 ($4.00\times10^4$), 719.1 ($1.30\times10^4$), 538.0 ($3.86\times10^4$), 503.0 ($5.55\times10^3$), 417.1 ($5.41\times10^4$), 367.0 ($9.99\times10^4$), 346.0 ($4.86\times10^4$). $^1$H NMR (400 MHz, $CDCl_3$) δ, ppm: 8.75 (splitting, 1H, 5-Meso H); 8.55, 8.30 (each s, 1H, 10,20-meso H); 8.12 (s, 2H, 2-ArH); 7.75 (s, 1H, Ar—H); 5.65 (s, N—$CH_2$); 5.20 (m, 1H, 17H); 4.25 (m, 2H, 7H and 18H); 4.00 (m,1H, 8H); 3.65, 3.55 and 3.50 (each s, 3H, —$CO_2CH_3$ and $2\times CH_3$); 3.02 (s, 3H, —$COCH_3$); 2.70-1.80 (several m, $17^1$H, $17^2$H, $8^{1-}CH_2$, total 4H); 1.98 (two doublets merged, 6H, 18-$CH_3$ and 7-$CH_3$); 1.60 (d, 3H, $3^1CH_3$); 1.10 (t, 3H, $7^2$-$CH_3$); 0.35 and −0.10 (each s, 1H, 2NH). $^{19}$F NMR (400 MHz, $CDCl_3$) δ, ppm: 13.136 (referenced to TFA). Mass calculated for $C_{50}H_{57}N_5O_5F_6$: 837.33. Found: 860.4 (M+Na).

Compound 16

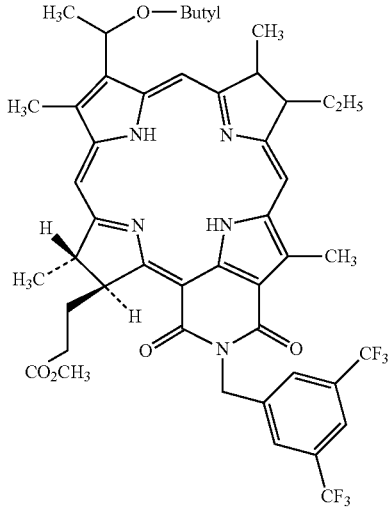

(R = butyl)

Melting point: sticky solid. UV-Vis ($CH_2Cl_2$): 783.1 ($4.21\times10^4$), 725.0($1.24\times10^4$), 537.0 ($4.01\times10^4$), 504.0 ($5.09\times10^3$), 470.1 ($4.42\times10^3$), 417.0 ($4.49\times10^4$), 367.0 ($9.97\times10^4$), 346.0 ($4.63\times10^4$). $^1$H NMR (400 MHz, $CDCl_3$) δ, ppm: 8.81 and 8.77 (splitting, 1H, 5-Meso H); 8.56, 8.27 (each s, 1H, 10, 20-meso H); 8.12 (s, 2H, 2-ArH); 7.75 (s, 1H, Ar—H); 5.65 (s, merged with q, 3H, N—$CH_2$ and $3^1$ CH); 5.20 (m,1H, 17-H); 4.25 (m, 2H, 7H and 18H); 4.00 (m, 1H, 8-H); 3.65, 3.55 and 3.20 (each s, 3H, 17-$CH_2CH_2CO_2CH_3$, 2-$CH_3$, 12-$CH_3$); 2.70-1.80 (several m, $17^1$H, $17^2$H, $8^{1-}CH_2$, total 4H); 2.00 and 1.75 (each d, 3H, 18-$CH_3$ and 7-$CH_3$); 1.75 (merged d 3H, $3^1CH_3$); 1.00-1.60 (several m, 6H, $CH_2$'s of butyl); 0.35 and −0.10 (each s, 1H, 2NH). Mass calculated for $C_{47}H_{51}N_5O_5F_6$: 879.38. Found: 902.3 (M+Na).

Compound 9c

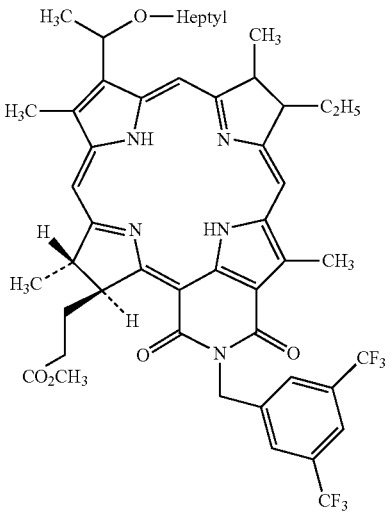

(R = heptyl)

Melting point: sticky solid. UV-Vis ($CH_2Cl_2$): 784.0 (4.06×$10^4$), 730.0 (1.26×$10^4$), 537.0 (3.90×$10^4$), 505.0 (5.50×$10^3$), 472.0 (5.24×$10^3$), 417.1 (4.60×$10^4$), 367.0 (9.80×$10^4$), 346.9 (4.68×$10^4$). $^1$H NMR (400 MHz, $CDCl_3$) δ, ppm: 8.80 and 8.78 (splitting, 1H, 5-Meso H); 8.56, 8.27 (each s, 1H, 10, 20-meso H); 8.16 (s, 2H, 2-ArH); 7.82 (s, 1H, Ar—H); 5.65 (s, 2H, N—$CH_2$); 5.70 (q, 1H, $3^1$ CH); 5.20 (m,1H, 17-H); 4.25 (m, 2H, 7H and 18H); 4.00 (m, 1H, 8-H); 3.65, 3.55 and 3.20 (each s, 3H, 17-$CH_2CH_2CO_2CH_3$, 2-$CH_3$, 12-$CH_3$); 2.70-1.80 (several m, $17^1$H, $17^2$H, $8^1CH_2$, total 4H); 2.00 and 1.75 (each d, 3H, 18-$CH_3$ and 7-$CH_3$); 1.75 (merged d 3H, $3^1CH_3$); 1.20-1.80 (several m, 12H, $CH_2$'s of heptyl); 1.10 (t, 3H, $CH_3$ of O-heptyl); 0.45 and −0.0.5 (each s, 1H, 2NH). $^{19}$F NMR (400 MHz, $CDCl_3$) δ, ppm: 13.137 (referenced to TFA). Mass calculated for $C_{44}H_{45}N_5O_5F_6$: 921.43. Found: 944.5 (M+Na).

Compound 15

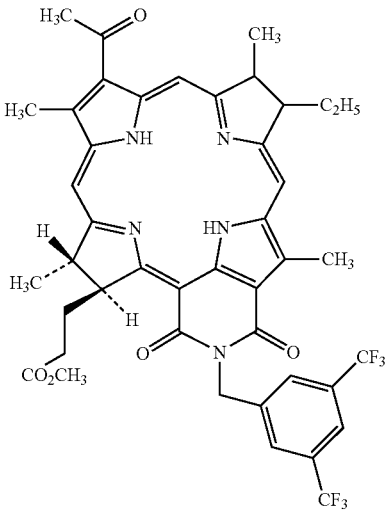

Melting point: sticky solid. UV-Vis (THF): 822.0 (6.01×$10^4$), 547.0 (3.63×$10^4$), 416.0 (4.38×$10^4$), 365.0 (8.38×$10^4$). NMR (400 MHz, $CDCl_3$) δ, ppm: 9.20, 8.75 and 8.60 (each s, 1H, meso H); 8.12 (s, 2H, 2-ArH); 7.75 (s, 1H, ArH); 5.75 (s, 2H, N—$CH_2$); 5.20 (m, 1H, 17H); 4.25 (m, 2H, 7H and 18H); 4.05 (m, 1H, 8H); 3.65 (s, 3H, $CH_3$); 3.50 (S, 6H, 2$CH_3$); 3.02 (s, 3H, $COCH_3$); 2.70-1.80 (several m, $17^1$H, $17^2$H, $8^{1-}CH_2$, total 4H); 1.80, 1.65 (each d, 3H, 18-CH, and 7-$CH_3$); 1.10 (t, 3H, $7^2$-$CH_3$); −0.80 and −0.70 (each s, 1H, 2NH). Mass calculated for $C_{43}H_{41}N_5O_5F_6$: 821.30. Found: 844.4 (M+Na).

Compound 18

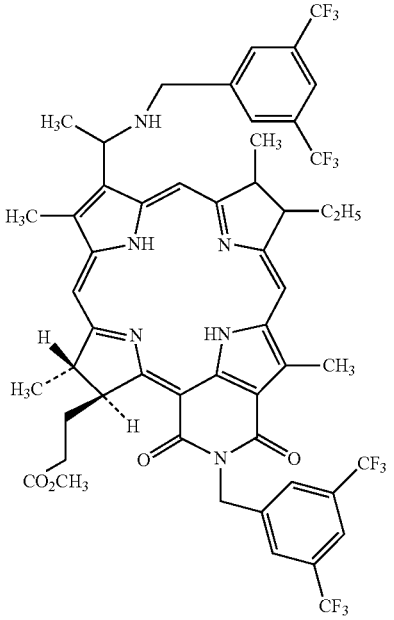

Melting point: sticky solid. UV-Vis ($CH_2Cl_2$): THF 784.1 (3.83×$10^4$), 538.0 (3.86×$10^4$), 470.1 (4.87×$10^3$), 417.1 (4.61×$10^4$), 367.9 (9.60×$10^4$). NMR (400 MHz, $CDCl_3$) δ, ppm: 9.02 and 9.05 [each s, 0.5H (splitting of 5H meso proton)]; 8.50 and 8.25 (each s, 1H, meso H); 8.18 (s, 2H, 2×Ar H); 7.75 (s, 1H, ArH); 7-65-7.80 (several S, 3H, ArH); 5.12 (m, 2H, $3^1$CH and 18H); 4.18 (m, 2H, 17H and 7H); 4.14 (m, 1H, 8H); 4.00 (m, 1H, —NH—$CH_2$); 3.55, 3.52 and 3.10 (each s, 3H, —$CO_2CH_3$, 12-$CH_3$ and 2-$CH_3$); 2.70-1.80 (several m, $17^1$H, $17^2$H, $8^{1-}CH_2$, total 4H); 1.80, 1.65 (each d, 3H, $3^1CH_3$, 18-$CH_3$ and 7-$CH_3$); 1.10 (t, 3H, $7^2$-$CH_3$); 0.40 and −0.20 (each s, 1H, 2NH). Mass calculated for $C_{52}H_{48}N_6O_4F_{12}$: 1048.35. Found: 1049.3 (M+1).

All ether analogs were isolated as diastereomeric mixtures. In the case of the purpurinimide analogs, no significant separation in the resonances of various protons was observed. However, in the bacteriochlorin series, the meso-proton (position-5) adjacent to the ether side chain (chiral center at position-3) showed two clear singlets for the resonances of both the isomers.

Example 4

In Vitro Photosensitizing Efficacy of Chlorin-related Compounds

Figure 2:
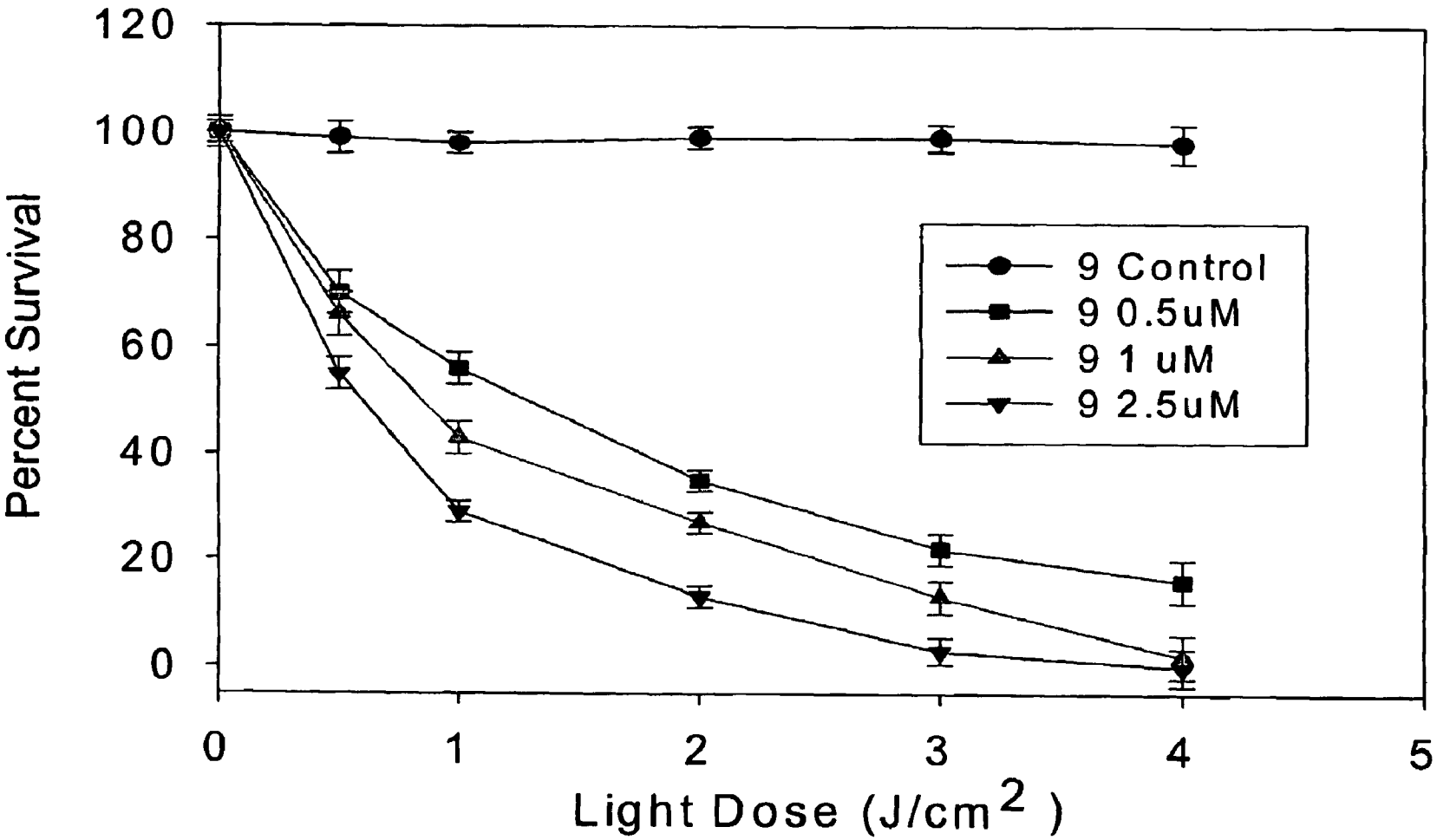
FIG. 2 illustrates in vitro photosensitizing efficacy of the purpurinimide (chlorin) photosensitizer 9 in RIF tumor cells.

RIF tumor cells were grown in alpha-DMEM with 10% fetal calf serum, penicillin and streptomycin. Cells were maintained in 5% $CO_2$, 95% air and 100% humidity. For determining PDT efficacy, these cells were plated in 96-well plates at a density of $1\times10^4$ cells well in complete media. After overnight incubation, in initial experiments in order to select the optimal dose, the substantially pure fluorinated photosensitizer 9 was initially added at variable concentrations. After a 3 hour incubation in the dark at 37° C., the cells were washed with PBS, then irradiated with a 1000 W Quartz Halogen Lamp with IR and bandpass dichroic filters to allow light between 400 nm-700 nm, at a dose rate of 16 mW/cm$^2$ at 700 nm. As can be seen from FIG. 2, compound 9 at 2.5 μM concentration produced 100% cell kill on exposing to light at a dose of 4J/cm$^2$. The other fluorinated and non-fluorinated purpurinimide analogs were then evaluated under similar conditions. Among the compounds evaluated, the fluorinated analogs produced better photosensitizing activity and the results are summarized in FIG. 3, which shows the in vitro photosensitizing efficacy of fluorinated (9, 12) and non-fluorinated (8, 11) purpurinimide-based photosensitizers at a concentration of 2.5 μM in RIF tumor cells, where the control is photosensitizer only with no light.

Example 5

In Vivo Photosensitizing Activity of Chlorin Related Compounds

The fluorinated and non-fluorinated photosensitizers 8, 9, 11 and 12 were also evaluated for their in vivo tumor response in C3H mice transplanted with RIF tumors (Henderson, B. W.; Bellnier, D. A.; Graco, W. R.; Sharma, A.; Pandey, R. K.; Vaughan, L.; Weishaupt, K. R.; and Dougherty, T. J., Cancer Res. 57: 4000 (1997)). In brief, C3H/HEJ mice were subjected to intradermal injection with $2\times10^5$ RIF cells in 30 mL HBSS w/o $Ca^{+2}$ and magnesium, into the flank and allowed to grow until they were 4-5 mm in diameter. The day before tumors were treatment size, the mice were injected with variable doses of substantially pure photosensitizers (1.0 mg/kg, 0.4 mg/kg). At 24 hours post injection the mice were anesthetized with ketamine and xylazine, and restrained in plastic holders, then treated with laser light from an argon pumped dye laser at 700 nm for a total fluence of 135 J/cm$^2$ at a fluence rate of 75 mW/cm$^2$. The mice (6 mice/group in two groups) were checked daily, the tumors were measured using two orthogonal measurements L and W (perpendicular to L) and the volumes were calculated using the formula $V=L\times W^2/2$ and recorded. Mice were considered cured if there was no palpable tumor at 90 days post-PDT treatment.

Figure 3:
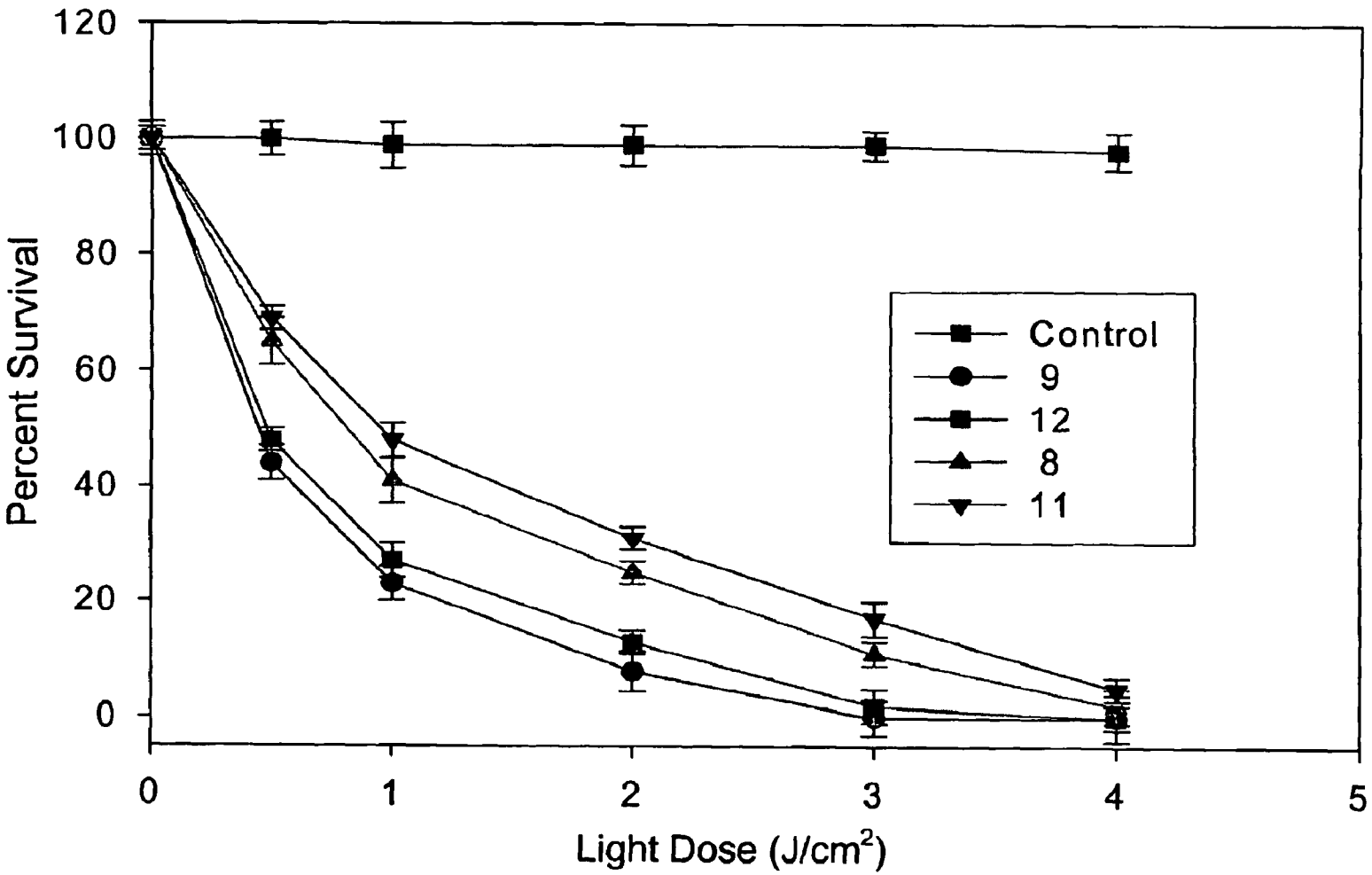
FIG. 3 illustrates comparative in vitro photosensitizing efficacy of four chlorin-based photosensitizers, consisting of a pair of fluorinated compounds (9, 12) and a pair of corresponding non-fluorinated compounds (8, 11).
Figure 4:
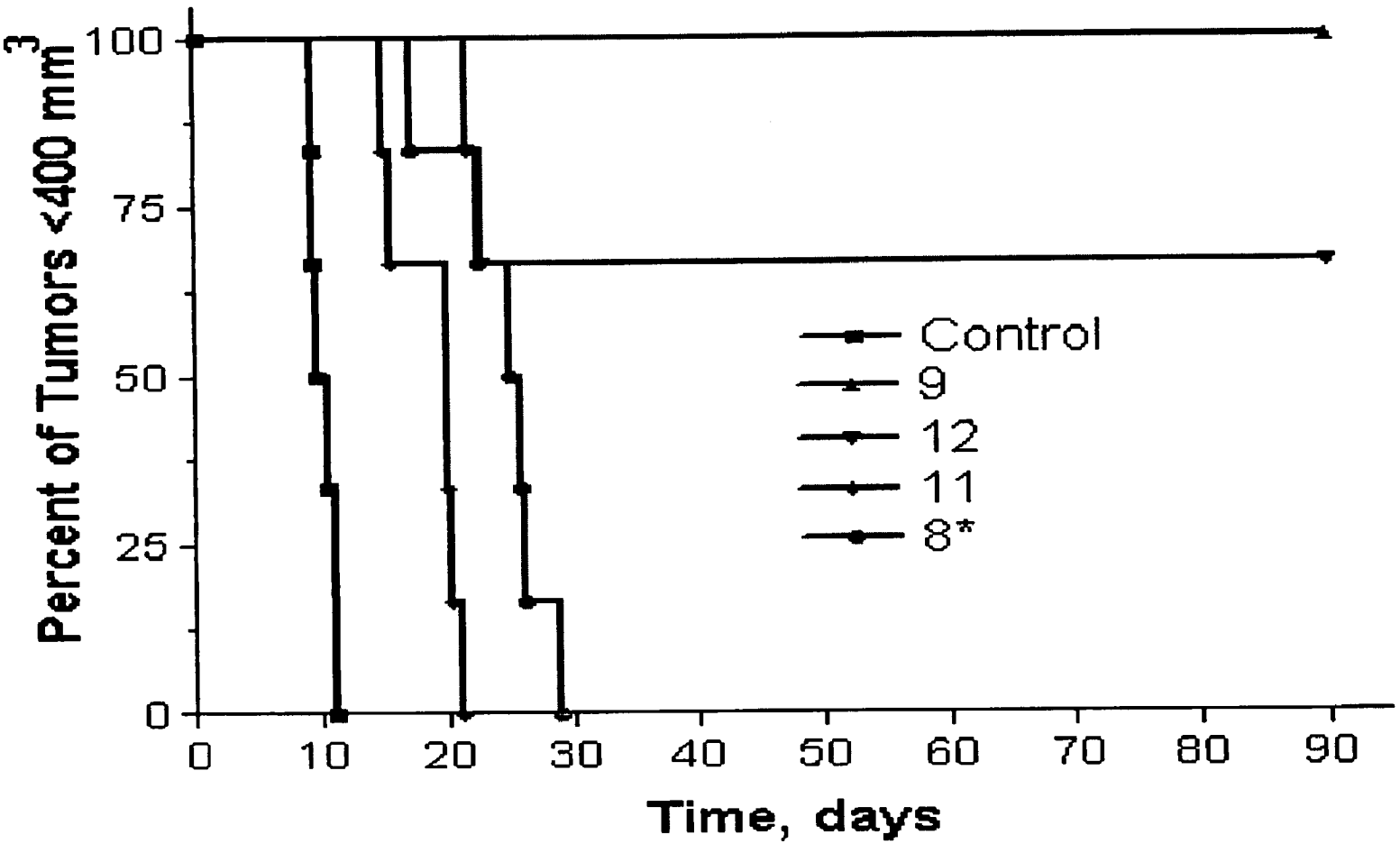
FIG. 4 illustrates the in vivo photosensitizing efficacy of the fluorinated (9, 12) and corresponding non-fluorinated (8, 11) chlorin photosensitizers of FIG. 3.

The in vitro results obtained from the fluorinated and non-fluorinated photosensitizers at a dose of 0.25 μmL/kg are summarized in FIG. 3, which shows comparative in vitro photosensitizing efficacy of fluorinated (9, 12) and non-fluorinated (8, 11) purpurinimide-based photosensitizers in RIF tumor cells, where the control shows photosensitizers only and no light. The in vitro results showed similar PDT efficacy of all purpurinimides. Compared to the in vitro results that showed similar PDT efficacy of all purpurinimides, the in vivo results were quite different. The in vivo results obtained from the fluorinated and non-fluorinated photosensitizers at a dose of 0.4 μmL/kg are summarized in FIG. 4. FIG. 4 compares the in vivo photosensitizing efficacy of fluorinated (9,12) and the corresponding non-fluorinated (8,11) purpurinimide-based photosensitizers in C3H/HeJ mice (6 mice/group). The mice were treated with light (706 nm, 135 J/cm2) at 24 hours post-injection. In the control group, six mice were exposed to light without injecting any photosensitizer. Among the fluorinated derivatives, purpurinimide 9 containing 3-O-(1'-butyloxy)ethyl and N-[3,5-bis-(trifluoromethyl) benzyl] substituents showed enhanced PDT efficacy (100% tumor response at day 90, i.e., in each group 6/6 mice were tumor free) than the related isomer 12 [purpurin-18-N-butyl-3-O-{1'-3",5"-bis(trifluoromethyl)-benzyl ether}imide] producing 66% tumor response on day 90. Under similar treatment conditions, the non-fluorinated analogs 8 and 11 were found to be significantly less effective.

Example 6

Determination of Tumor vs. Skin Uptake of Chlorin-related Compounds

For a compound to be biologically active under the PDT treatment conditions with reduced skin phototoxicity (a major drawback associated with most of the porphyrin-based compounds), it is necessary that it show a significantly higher accumulation in tumor than skin. Therefore, the uptake of the newly synthesized purpurinimide analogs 8, 9, 11 and 12 in tumor vs. skin was determined by in vivo reflectance spectroscopy (Zheng, G.; Potter, W. R.; Camacho, S. H., Missert, J. R., Wang, G., Bellnier, D. A., Henderson, B. W., Rodgers, M. A. J., Dougherty, T. J., and Pandey, R. K., J. Med. Chem. 44: 1540-1559 (2001)). For these experiments, mice were first anesthetized using intraperitoneal administration of ketamine xylazine. The optical power as a function of wavelength was recorded before the i.v. injection of the photosensitizer. The drug was then injected and the spectrum was again recorded. The in vivo drug absorption spectrum is best displayed by determining the log of the ratio of the post-injection spectrum to the pre-injection spectrum. In a typical experiment, for measuring tumor uptake, the photosensitizers were injected into mice implanted with RIF tumors at a dose of 5.0 μmol/kg. All photosensitizers produced high tumor uptake and showed a considerable difference between tumor and skin levels 24 hour after injection, indicating enhanced tissue selectivity. The results for reflectance spectroscopy are shown for purpurinimide analogs 8, 9, 11 and 12 in FIGS. 5A, 6A, 7A and 8A, respectively, and the results showing the concentration of the compounds in RIF tumor versus C3H skin as a function of time are shown for purpurinimide analogs 8, 9, 11 and 12 in FIGS. 5B, 6B, 7B and 8B, respectively.

Example 7

In Vivo Photosensitizing Activity of Bacteriochlorin-related Compounds

Figure 9:
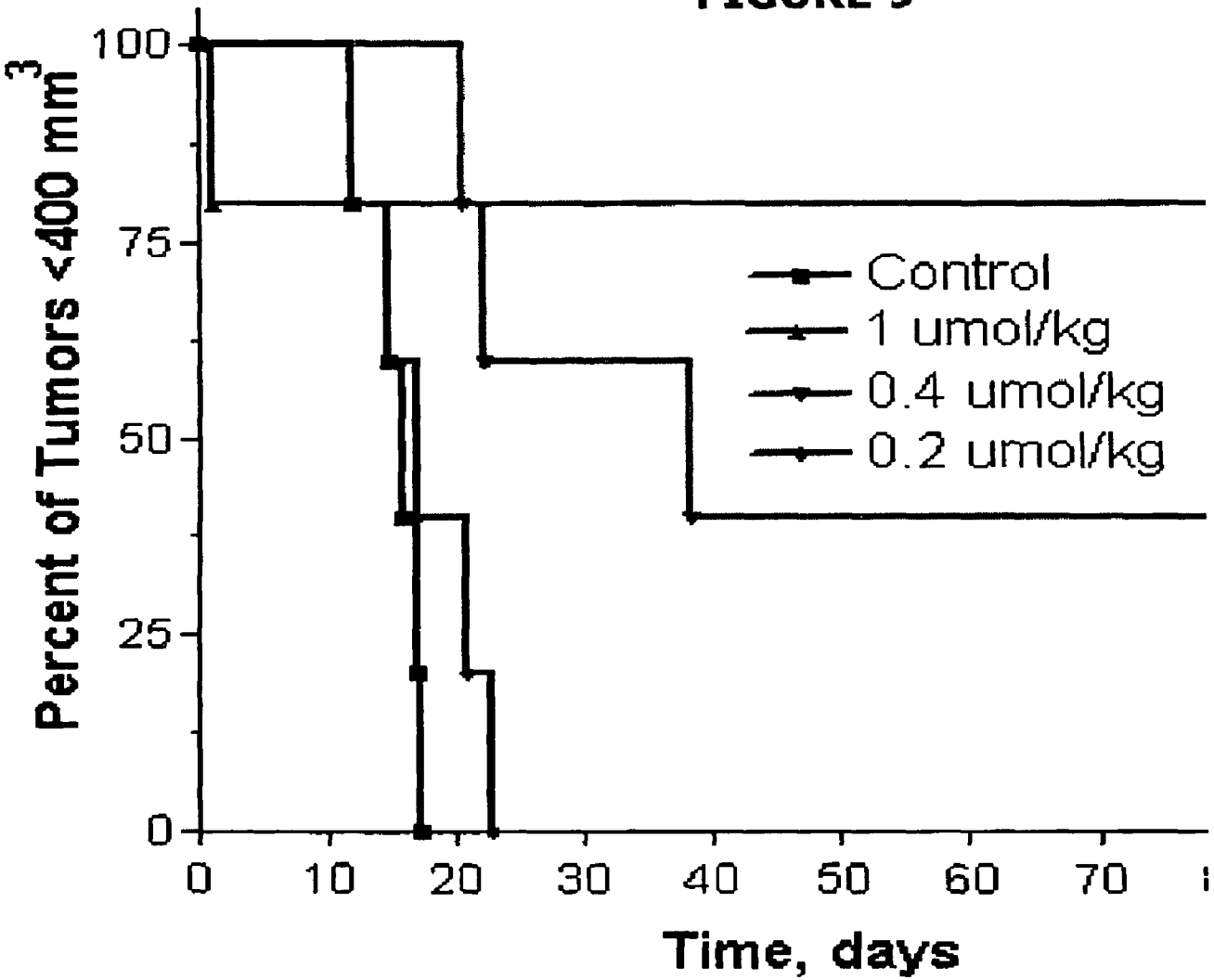
FIG. 9 and FIG. 10 illustrate the in vivo photosensitizing efficacy of bacteriochlorins 16 and 18, respectively, at varying concentrations.
Figure 10:
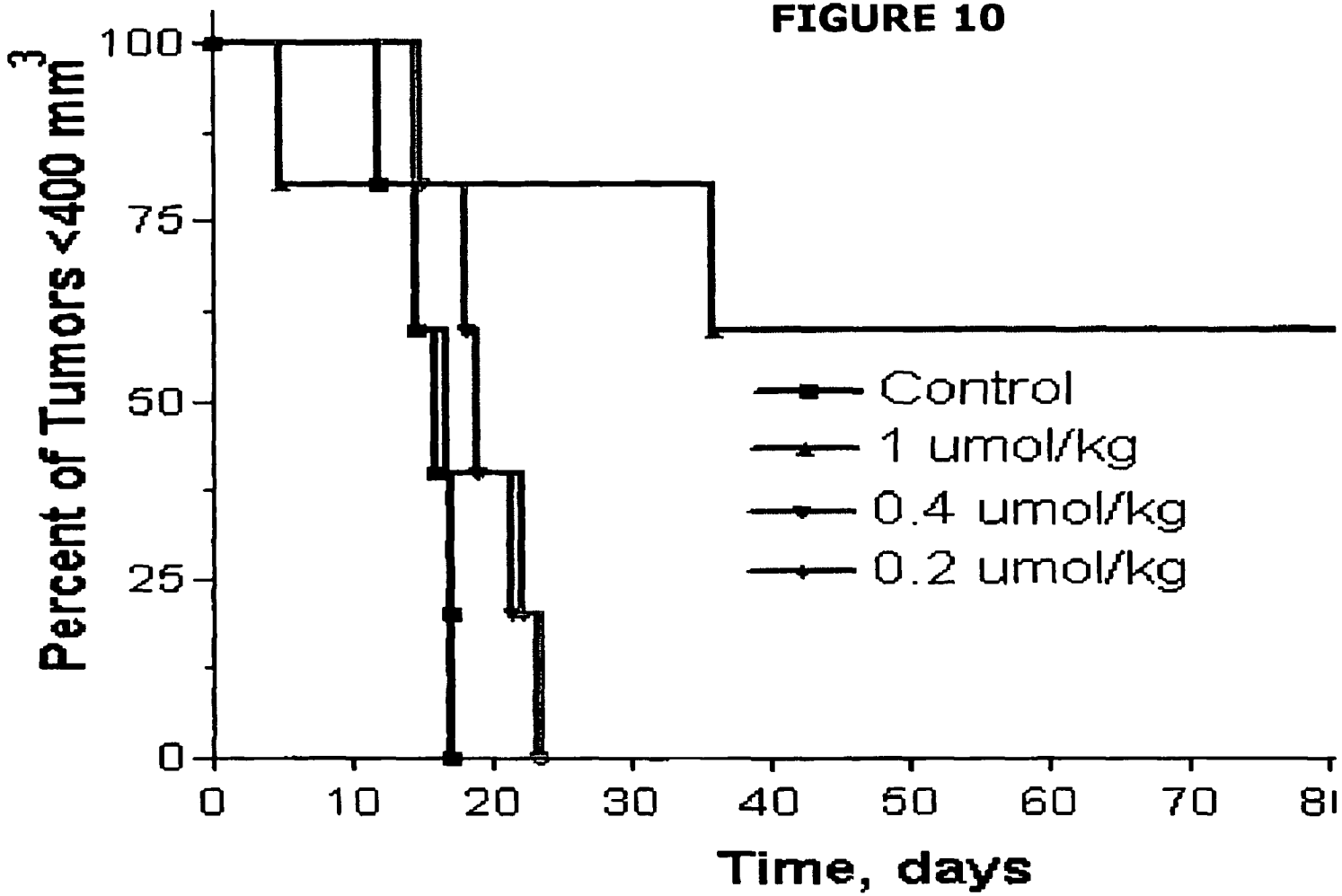

The in vivo photosensitizing efficacy of bacteriochlorins 16 and 18 was determined in C3H mice (5 mice/group) at variable concentration up to 1.0 μmol/Kg. The experimental conditions used are those as described above in EXAMPLE 5 for the purpurinimide analogs. The results obtained for bacteriochlorins 16 and 18 are shown in FIG. 9 and FIG. 10, respectively. Compared to compound 18, bacteriochlorin 16 showed improved PDT efficacy. For example, bacteriochlorin 16 at a dose of 1.0 μmol/Kg produced 80% tumor response (4/5 mice were tumor free at day 90), whereas at a same dose bacteriochlorin 18 produced 60% tumor response (3/5 tumor free at day 90). At a lower dose (0.4 μmol/Kg) bacteriochlorin 16 certainly showed improved photosensitizing efficacy (75% tumor cure at day 25 and 40% tumor cure on day 90) compared to 16 (day 15, 100% tumor cure and at day 25, no tumor response).

Example 8

Tumor vs. Muscle Uptake of Bacteriochlorin-related Compounds

The tumor vs. muscle uptake of bacteriochlorins 16 and 18 was determined in C3H mice by following the experimental conditions described for purpurinimide analogs. Both bacteriochlorins produced a considerably higher tumor uptake than the surrounding muscle. The results for reflectance spectroscopy are shown for of bacteriochlorins 16 and 18 in FIGS. 11A and 12A, respectively, and the results showing the concentration of the compounds in RIF tumor versus C3H skin as a function of time are shown for bacteriochlorins 16 and 18 in FIGS. 11B and 12B, respectively.

Example 9

PDT Targeted at Helicobacter Pylori

This EXAMPLE describes the clinical application of targeted photosensitizers to the treatment of an infection using PDT.

Helicobacter pylori is reportedly associated with tumors of the stomach in mice and as a putative agent of ulcerative pathology in humans. In this EXAMPLE, a capsular or pill-shaped and sized light source is administered orally to a patient, so that it passes into the stomach of the patient, where it administers light. Alternatively, an optical fiber may be passed into the stomach via the nasopharynx to administer light to the treatment site. In order to implement targeted PDT for treating ulcers in humans, an antibody that is targeted against a suitable Helicobacter pylori antigen is conjugated to a compound provided herein and formulated into a pharmaceutical preparation that releases the conjugated compound to a gastric mucus/epithelial layer where the bacterium is found. The compound is ingested at a time when the stomach and duodenum is substantially empty in order to promote binding of the compound to bacterium. Any unbound compound is diluted by gastric juice and carried distally by peristalsis to be eliminated from the body in fecal matter. Light sources suitable for intraluminal passage are disclosed in any one of U.S. Pat. Nos. 5,766,234; 5,782,896; 5,800,478; and 5,827,186, and pill or capsule shaped light sources are disclosed in U.S. Pat. No. 6,273,904, the disclosure of each being specifically hereby incorporated herein in its entirety. The light source is preferably energized just prior to its ingestion or remotely after ingestion, when in the stomach or in a desired intraluminal passage. If necessary, multiple light sources are ingested to insure that adequate photoactivation of the localized compound occurs sufficient to kill the bacterium. The light source(s) may be deactivated after passage beyond the duodenum to avoid unwanted distal photoactivation. In this manner, a photosensitizing agent comprising the conjugated compound is activated topically without the need for a procedure such as endoscopy with fiberoptic gastric illumination in order to provide the activating light. Since the compound is targeted, nonspecific uptake by normal tissue and other normal compositions of the body is minimized in order to prevent injury to normal gastric tissue and problems with the gastric system.

In this exemplary treatment, the following protocol may be utilized:

Step 1 Patient is NPO for six hours to insure that the stomach is empty.

Step 2 The targeted compound is ingested.

Step 3 One hour elapses to allow for bacterial binding and distal passage of unbound compound. The optimal period can be longer or shorter and is readily determined by measuring the clinical response; for example, response can be determined endoscopically by observation and biopsy.

Step 4 One or more light sources are ingested sequentially and activated in the stomach. The length of time that light is administered by these sources and the number of sources that are ingested will be determined clinically in a light dose escalation study. The churning action of the stomach serves to translocate the light source(s) so that the light is distributed more evenly prior to passage of the source(s) into the duodenum. Since each light source is small (the size of a pill or tablet), it passes easily out through the GI system via peristalsis.

Step 5 The light sources are deactivated after distal passage beyond the gastroduodenal area and excreted in fecal matter.

Note that it is also contemplated that an external light source located over the gastric area can be used to transcutaneously administer light to the treatment site. The use of an external light source requires that the targeted compound and the light source absorb and emit in the near infrared to infrared range, respectively, so that the light will efficiently penetrate the patient's skin and reach the treatment site.

Example 10

PDT for Targeting Pulmonary Tuberculosis

An target compound provided herein is formulated to bind with great affinity to Mycobacterium tuberculosis in a selective and specific manner. Preferably, the targeted compound is formulated as an aerosol, which can be easily inhaled, enabling distribution into all lung segments. Steam is then inhaled to solubilize any unbound targeted compound and facilitate its removal from the lung by exhalation. Alternatively, the targeted compound is formulated as an injectable compound and administered intravenously. Either way, the bound targeted compound is photoactivated by an external light source disposed on the chest and/or back.

Step 1 The targeted compound is inhaled or injected.

Step 2 Time is allowed to elapse to allow binding of the targeted compound with the Mycobacterium tuberculosis, followed by steam inhalation to remove any unbound compound (if inhaled). The time required to ensure a therapeutically effective dose of bound targeted compound may be routinely determined clinically using standard clinical practices and procedures.

Step 3 The light source is disposed adjacent to the thorax and activated for a sufficient time to ensure that therapeutic irradiation has occurred, which may be routinely determined clinically using conventional clinical practices and procedures. The fluence rate and total fluence dose may be determined as noted above.

Note that alternatively, an internal light source disposed within the thoracic area can be used to administer the light. The use of an external light source requires that the targeted compound and the light source respectively absorb and emit light in the near infrared to infrared range to ensure efficient skin penetration of the light.

Example 11

PDT for Targeting Otitis Media

A photosensitizer conjugate is formulated which binds with great affinity to Streptococcus pneumoniae and Hemophilus influenzae in a selective manner. The targeted conjugate is formulated into an injectable, which can be administered intravenously or instilled topically into the middle ear via a previously placed tympanostomy tube. The drug is activated using light emitted by a small light source about the size, shape, and weight of a hearing aid, which is disposed behind the ear and aimed at the middle ear, so that the light passes into the middle ear transcutaneously.

Step 1 The targeted compound fluid formulation is instilled into the middle ear.

Step 2 Sufficient time is allowed to elapse to allow binding of the targeted compound with the disease organisms, and then, any excess fluid is drained away by gravity or actively aspirated using a needle and syringe.

Step 3 The light source is positioned behind the ear and activated. The light source need not be very intense since the middle ear cavity is small.

Since modifications will be apparent to those of skill in this art, it is intended that this invention be limited only by the scope of the appended claims.

What is claimed is:

[1. A compound of the formula:

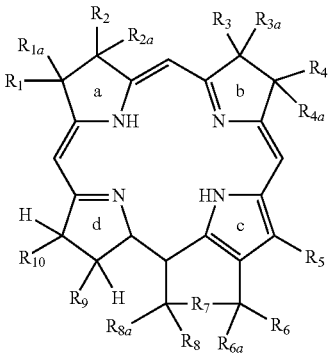

or a pharmaceutically acceptable derivative thereof, wherein:

$R_1$ and $R_2$ are each independently substituted or unsubstituted alkyl, substituted or unsubstituted alkenyl, —C(O)$R_a$ or —COOR$_a$, or —CH(CH$_3$)(OR$_a$) or —CH(CH$_3$)(O(CH$_2$)$_n$XR$_a$) where $R_a$ is hydrogen, substituted or unsubstituted alkyl, substituted or unsubstituted alkenyl, substituted or unsubstituted alkynyl, or substituted or unsubstituted cycloalkyl; where $R_2$ may be —CH═CH$_2$, —CH(OR$_{20}$) CH$_3$, —C(O)Me, —(═NR$_{21}$)CH$_3$ or —CH(NHR$_{21}$)CH$_3$ where X is an aryl or heteroaryl group;

n is an integer of 0 to 6;

where $R_{20}$ is methyl, butyl, heptyl, docecyl or 3,5-bis(trifluoromethyl)-benzyl; and $R_{21}$ is 3,5,-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form ═O;

$R_7$ is a covalent bond, alkylene, azaalkyl, or azaaraalkyl or ═NR$_{20}$ where $R_{20}$ is 3,5-bis(tri-fluoromethyl)benzyl or —CH$_2$X—R$^1$ or YR$^1$ where Y is an aryl or heteroaryl group;

$R_8$ and $R_{8a}$are each independently hydrogen or substituted or unsubstituted alkyl or together form ═O;

$R_9$ and $R_{10}$ are each independently hydrogen, or substituted or unsubstituted alkyl and $R_9$ may be —CH$^2$CH$_2$COOR$^2$ where R$^2$ is an alkyl group that may optionally substituted with one or more fluorine atoms;

each of $R_1$-$R_{10}$, when substituted, is substituted with one or more substituents each independently selected from Q, where Q is alkyl, haloalkyl, halo, pseudohalo, —COOR$_b$ where $R_b$ is hydrogen, alkyl, alkenyl, alkynyl, cycloalkyl aryl, heteroaryl, araalkyl, or OR$_c$ where $R_c$ is hydrogen, alkyl, alkenyl, alkynyl, cycloalkyl, or aryl, or CONR$_d$R$_e$ where $R_d$ and $R_e$ are each independently hydrogen, alkyl, alkenyl, alkynyl, cycloalkyl or aryl, or NR$_f$R$_g$ where $R_f$ and $R_g$ are each independently hydrogen, alkyl, alkenyl, alkynyl, cycloalkyl, or aryl, or ═NR$_h$ where $R_h$ is hydrogen, alkyl, alkenyl, alkynyl, cycloalkyl, or is an amino acid residue;

each Q is independently unsubstituted or is substituted with one or more substituents each independently selected from $Q_1$, where $Q_1$ is alkyl, haloalkyl, halo, pseudohalo, or —COOR$_b$ where $R_b$ is hydrogen, alkyl, alkenyl, alkynyl, cycloalkyl aryl, heteroaryl, araalkyl, or OR$_c$ where $R_c$ is hydrogen, alkyl, alkenyl, alkynyl, cycloalkyl or aryl, or CONR$_d$ R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or ═NR$_h$ where $R_h$ is hydrogen, alkyl, alkenyl, alkynyl, cycloalkyl, or aryl, or is an amino acid residue;

with the proviso that the compound contains at least one fluorine atom in at least one 3,5,-bis(trifluoromethyl) benzyl group or in at least one R, R$^1$, or R$^2$ group.]

[2. The compound of claim 1, wherein:

$R_1$ is methyl;

$R_{1a}$ and $R_{2a}$ together form a covalent bond;

$R_3$ is methyl;

$R_4$ is ethyl;

$R_{3a}$ and $R_{4a}$ are each independently hydrogen, or together form a covalent bond;

$R_5$ is methyl;

$R_9$ is CH$_2$CH$_2$COOH or CH$_2$CH$_2$COOMe;

$R_{10}$ is methyl.]

[3. The compound of claim 1, wherein:

$R_2$ is CH═CH$_2$, CH(OR$_{20}$)CH$_3$, C(O)Me, C(═NR$_{21}$)CH$_3$ or CH(NHR$_{21}$)CH$_3$;

where $R_{20}$ is methyl, butyl, heptyl, dodecyl or 3,5-bis(trifluoromethyl)benzyl; and $R_{21}$ is 3,5-bis(trifluoromethyl)benzyl.]

[4. The compound of claim 1 having the formula:

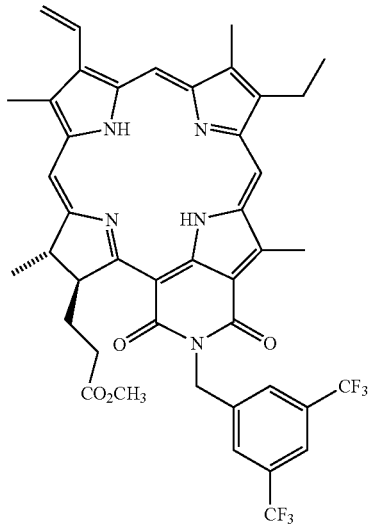

or a pharmaceutically acceptable derivative thereof.]

[5. The compound of claim 1 having the formula:

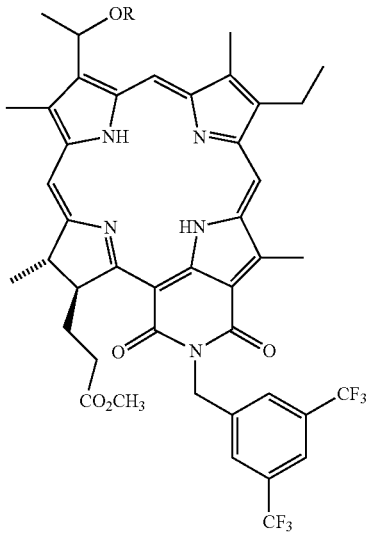

or a pharmaceutically acceptable derivative thereof, wherein: R is methyl, butyl, heptyl or dodecyl.]

[6. The compound of claim 1 having the formula:

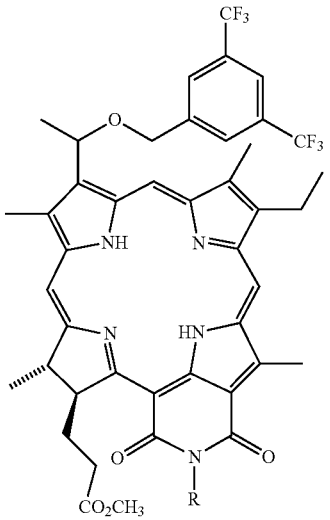

or a pharmaceutically acceptable derivative thereof, wherein: R is methyl, butyl, heptyl or dodecyl.]

[7. The compound of claim 1 having the formula:

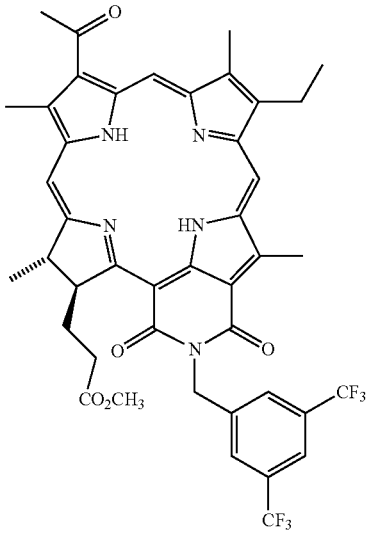

or a pharmaceutically acceptable derivative thereof.]

[8. The compound of claim 1 having the formula:

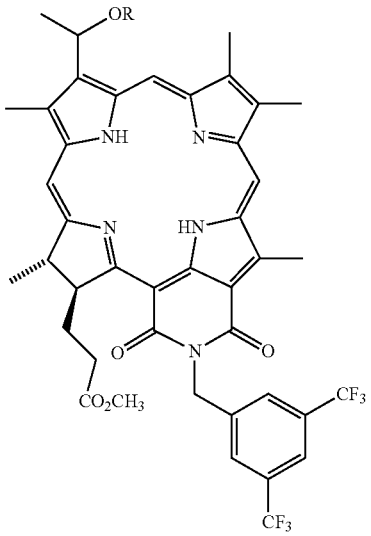

or a pharmaceutically acceptable derivative thereof, wherein: R is methyl, butyl, heptyl or dodecyl.]

[9. The compound of claim 1 having the formula:

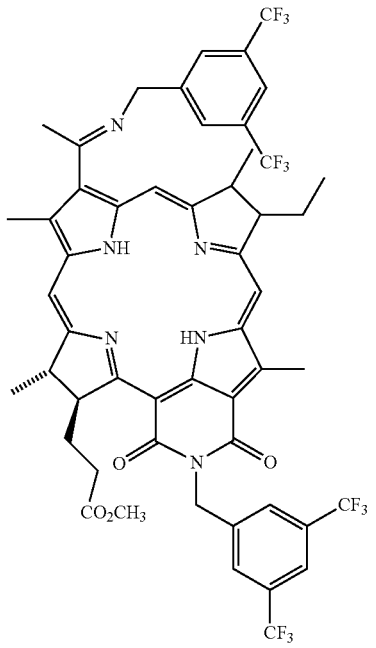

or a pharmaceutically acceptable derivative thereof.]

[10. The compound of claim 1 having the formula:

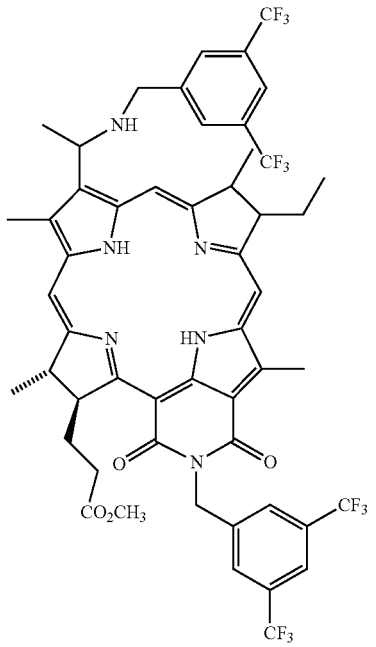

or a pharmaceutically acceptable derivative thereof.]

[11. The compound of claim 1 having the formula

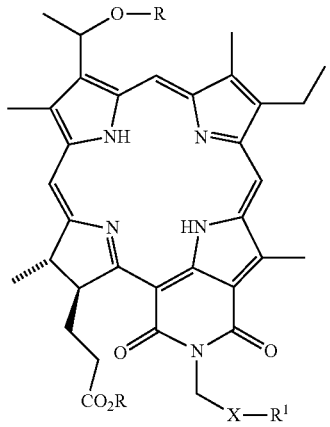

or a pharmaceutically acceptable derivative thereof, wherein:

X is an aryl or heteroaryl group;

R and $R^1$ are each independently alkyl, aryl, or heteroaryl groups having 1-20 carbon atoms, wherein at least one of R and $R^1$ is substituted with at least one fluorine atom; and $R^2$is an alkyl group, optionally substituted with one or more fluorine atoms.]

[12. The compound of claim 1 having the formula:

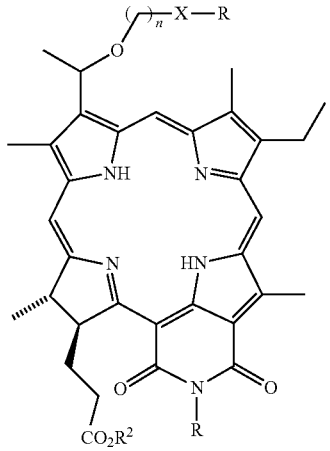

or a pharmaceutically acceptable derivative thereof, wherein:

X is an aryl or heteroaryl group;

n is an integer from 0 to 6;

R and $R^1$ are each independently alkyl, aryl, or heteroaryl groups having 1-20 carbon atoms, wherein at least one of R and $R^1$ is substituted with at least one fluorine atom; and $R^2$ is an alkyl group, optionally substituted with one or more fluorine atoms.]

[13. The compound of claim 1 having the formula

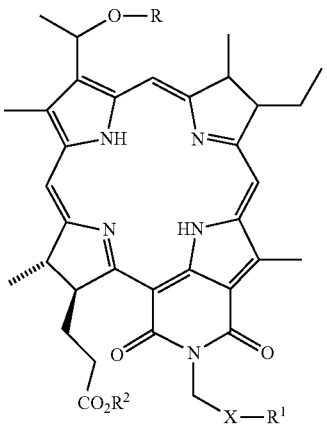

or a pharmaceutically acceptable derivative thereof, wherein:

X is an aryl or heteroaryl group;

R and $R^1$ are each independently alkyl, aryl, or heteroaryl groups having 1-20 carbon atoms, wherein at least one of R and $R^1$ is substituted with at least one fluorine atom; and $R^2$ is an alkyl group, optionally substituted with one or more fluorine atoms.]

[14. The compound of claim 1 having the formula:

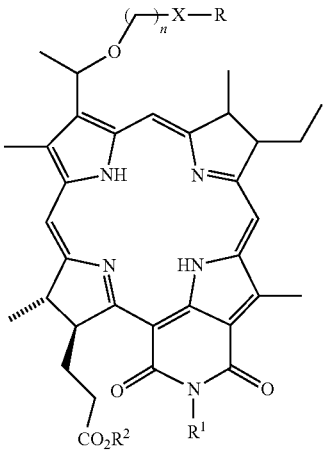

or a pharmaceutically acceptable derivative thereof, wherein:

X is an aryl or heteroaryl group;

n is an integer from 0 to 6;

R and $R^1$ are each independently alkyl, aryl, or heteroaryl groups having 1-20 carbon atoms, wherein at least one of R and $R^1$ is substituted with at least one fluorine atom; and $R^2$ is an alkyl group, optionally substituted with one or more fluorine atoms.]

[15. The compound of claim 1 having the formula

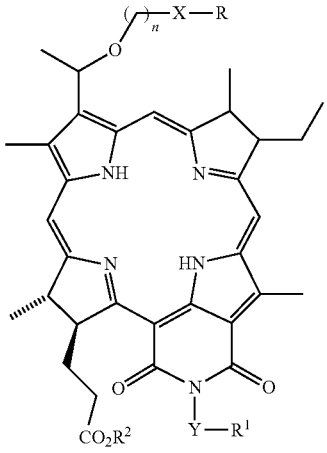

or a pharmaceutically acceptable derivative thereof, wherein:

X and Y are each independently an aryl or heteroaryl group;

n is an integer from 0 to 6;

R and $R^1$ are each independently alkyl, aryl, or heteroaryl groups having 1-20 carbon atoms, wherein at least one of R and $R^1$ is substituted with at least one fluorine atom; and $R^2$ is an alkyl group, optionally substituted with one or more fluorine atoms.]

[16. A pharmaceutical composition, comprising a compound of claim 1 or a pharmaceutically acceptable derivative thereof in a pharmaceutically acceptable carrier.]

[17. The compound of claim 10 or a pharmaceutically acceptable derivative thereof when used for the detection or treatment or both of hyperproliferative tissue.]

[18. The compound of claim 11 or a pharmaceutically acceptable derivative thereof when used for the detection or treatment or both of hyperproliferative tissue.]

[19. The compound of claim 12 or a pharmaceutically acceptable derivative thereof when used for the detection or treatment or both of hyperproliferative tissue.]

*20. A compound of the formula:*

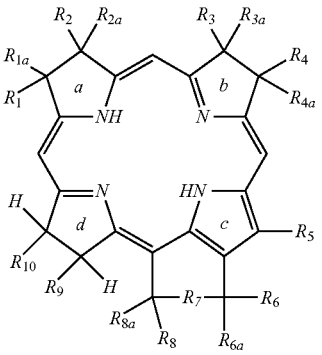

*wherein:*

*said compound is pharmaceutically acceptable;*

*$R_1$ and $R_2$ are each independently alkyl, alkenyl, —C(O)$R_a$ or —COO$R_a$ or —CH($CH_3$)(O$R_a$) or —CH($CH_3$)(O($CH_2$)$_n$X$R_a$) where $R_a$ is hydrogen, alkyl, alkenyl, alk-* enyl, or cycloalkyl; where $R_2$ may also be, —C(═$NR_{21}$)$CH_3$, or —CH($NHR_{21}$)$CH_3$;

where X is an aryl or heteroaryl group;

n is an integer of 0 to 6;

$R_{21}$ is 3,5-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form ═O;

$R_7$ is a covalent bond, alkylene, azaalkyl, or azaaraalkyl or

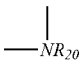

where $R_{20}$ is 3,5-bis(trifluoromethyl)benzyl;

$R_8$ and $R_{8a}$ are each independently hydrogen or substituted or unsubstituted alkyl or together form ═O;

$R_9$ and $R_{10}$ are each independently hydrogen, or substituted or unsubstituted alkyl and $R_9$ may be —$CH_2CH_2COOR^2$ where $R^2$ is an alkyl group that may be optionally substituted with one or more fluorine atoms;

each of each of $R_3$-$R_6$, $R_8$-$R_{10}$, $R_{1a}$-$R_{4a}$, $R_{6a}$, and $R_{8a}$, when substituted, is substituted with one or more substituents each independently selected from Q, where Q is alkyl, haloalkyl, halo or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, or aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl;

each Q is independently unsubstituted or is substituted with one or more substituents each independently selected from $Q_1$, where $Q_1$ is alkyl, haloalkyl, halo, pseudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl;

with the proviso that the compound contains at least one 3,5-bis(trifluoromethyl)benzyl group.

21. The compound of claim 20 wherein:

$R_1$ is methyl;

$R_{1a}$ and $R_{2a}$ together form a covalent bond;

$R_3$ is methyl;

$R_4$ is ethyl;

$R_{3a}$ and $R_{4a}$ are each independently hydrogen, or together form a covalent bond;

$R_5$ is methyl;

$R_9$ is $CH_2CH_2COOMe$;

$R_{10}$ is methyl.

22. The compound of claim 20, wherein:

$R_2$ is CH═$CH_2$, C(O)Me, C(═$NR_{21}$)$CH_3$, CH($NHR_{21}$)$CH_3$, and $R_{21}$ is 3,5-bis(trifluoromethyl)benzyl.

23. A compound having the formula:

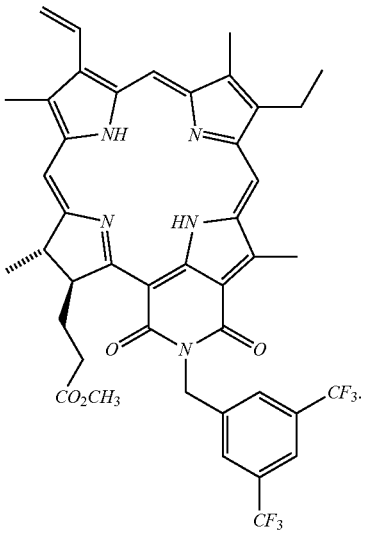

24. A compound having the formula:

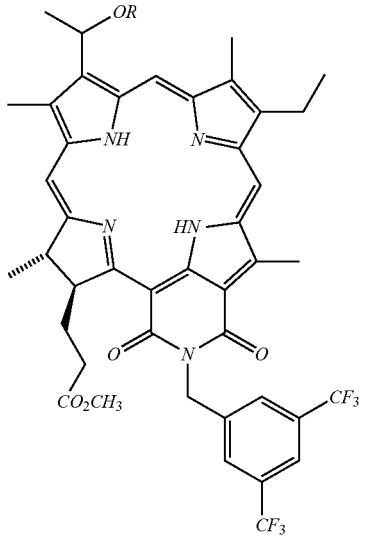

wherein R is methyl, butyl, heptyl or dodecyl.

25. A compound having the formula:
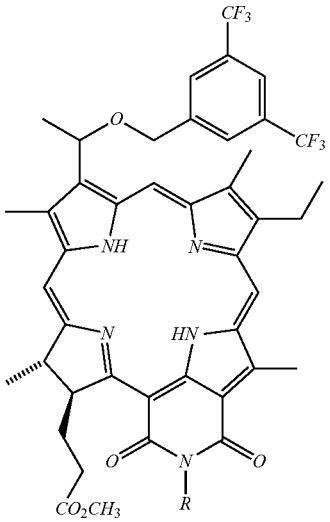
wherein R is methyl, butyl, heptyl or dodecyl.
26. A compound having the formula:
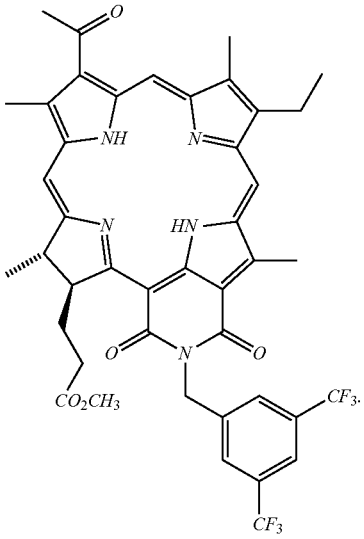
27. A compound having the formula:
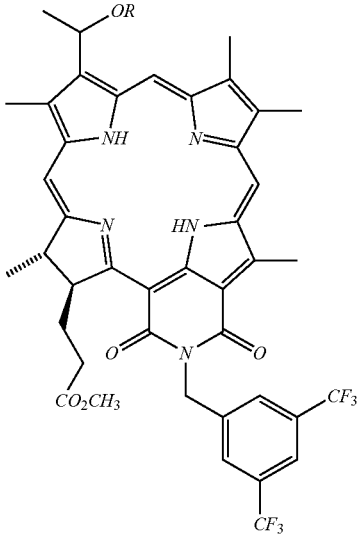
wherein R is methyl, butyl, heptyl or dodecyl.
28. A compound having the formula:
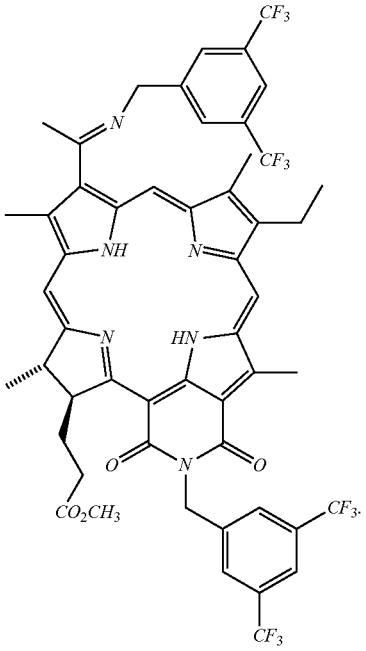

29. A compound having the formula:

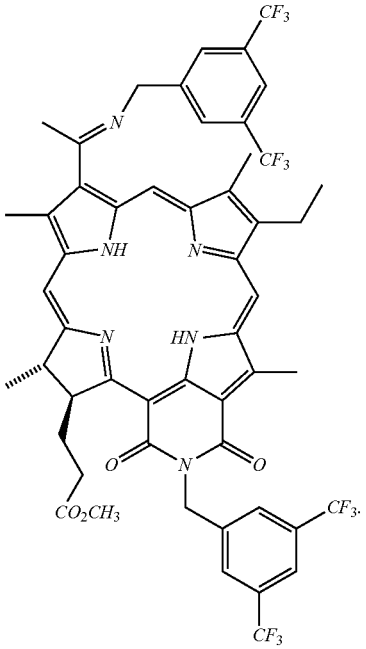

30. A compound having the formula:

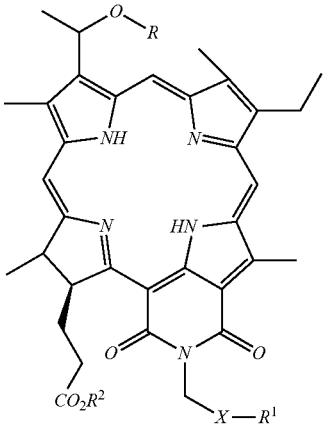

wherein:

X is an aryl or heteroaryl group;

R and $R^1$ are each independently alkyl groups having 1-20 carbon atoms, wherein at least one of R and $R^1$ is substituted with at least one fluorine atom; and $R^2$ is an alkyl group, optionally substituted with one or more fluorine atoms.

31. A compound having the formula:

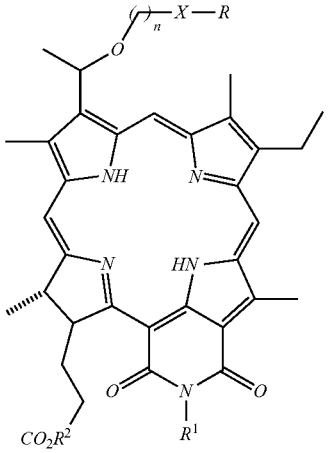

wherein:

X is an aryl or heteroaryl group;

n is an integer from 0 to 6;

R and $R^1$ are each independently alkyl groups having 1-20 carbon atoms, wherein at least one of R and $R^1$ is substituted with at least one fluorine atom; and $R^2$ is an alkyl group, optionally substituted with one or more fluorine atoms.

32. A compound having the formula:

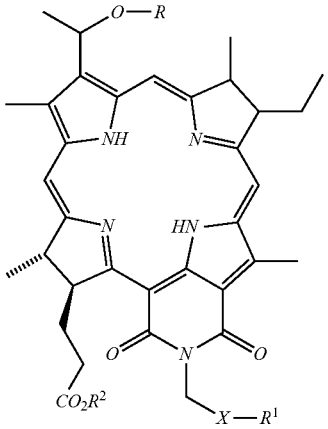

wherein:

X is an aryl or heteroaryl group;

R and $R^1$ are each independently alkyl groups having 1-20 carbon atoms, wherein at least one of R and $R^1$ is substituted with at least one fluorine atom; and $R^2$ is an alkyl group, optionally substituted with one or more fluorine atoms.

*33. A compound having the formula:*

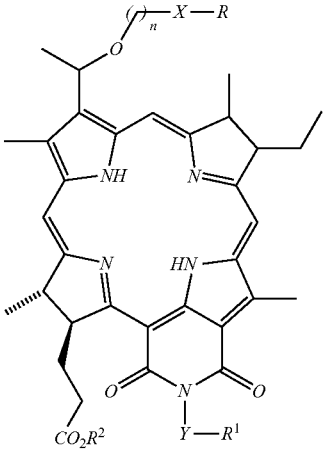

*wherein:*

*X and Y are each independently an aryl or heteroaryl group;*

*n is an integer from 0 to 6;*

*R and $R^1$ are each independently alkyl groups having 1-20 carbon atoms, wherein at least one of R and $R^1$ is substituted with at least one fluorine atom; and*

*$R^2$ is an alkyl group, optionally substituted with one or more fluorine atoms.*

*34. A pharmaceutical composition, comprising a compound of claim 20 in a pharmaceutically acceptable carrier.*

* * * * *